(12) United States Patent
Watzlawik et al.

(10) Patent No.: US 11,180,543 B2
(45) Date of Patent: Nov. 23, 2021

(54) TREATMENT OF NEONATAL HYPOXIA INCLUDING IMPAIRMENTS OR EFFECTS THEREOF

(71) Applicant: MAYO FOUNDATION FOR MEDICAL EDUCATION AND RESEARCH, Rochester, MN (US)

(72) Inventors: Jens O. Watzlawik, Ponte Vedra Beach, FL (US); Arthur E. Warrington, Rochester, MN (US); Moses Rodriguez, Rochester, MN (US); William A. Carey, Rochester, MN (US)

(73) Assignee: Mayo Foundation For Medical Education and Research, Rochester, MN (US)

( * ) Notice: Subject to any disclaimer, the term of this patent is extended or adjusted under 35 U.S.C. 154(b) by 161 days.

(21) Appl. No.: 15/524,058

(22) PCT Filed: Nov. 6, 2015

(86) PCT No.: PCT/US2015/059630
§ 371 (c)(1),
(2) Date: May 3, 2017

(87) PCT Pub. No.: WO2016/073963
PCT Pub. Date: May 12, 2016

(65) Prior Publication Data
US 2017/0355754 A1 Dec. 14, 2017

Related U.S. Application Data

(60) Provisional application No. 62/076,669, filed on Nov. 7, 2014.

(51) Int. Cl.
| | | |
|---|---|---|
| *A61P 25/02* | (2006.01) | |
| *A61K 39/395* | (2006.01) | |
| *C07K 16/18* | (2006.01) | |
| *C07K 16/28* | (2006.01) | |
| *A61K 45/06* | (2006.01) | |
| *A61K 39/00* | (2006.01) | |

(52) U.S. Cl.
CPC ........ *C07K 16/18* (2013.01); *A61K 39/39533* (2013.01); *A61K 45/06* (2013.01); *A61P 25/02* (2018.01); *C07K 16/28* (2013.01); *A61K 2039/505* (2013.01); *C07K 2317/24* (2013.01); *C07K 2317/56* (2013.01)

(58) Field of Classification Search
CPC .... C07K 16/18; C07K 16/28; C07K 2317/24; C07K 2317/56; A61P 25/02; A61K 39/39533; A61K 45/06; A61K 2039/505; A61K 39/395
See application file for complete search history.

(56) References Cited

U.S. PATENT DOCUMENTS

| | | | |
|---|---|---|---|
| 7,473,423 B2 | 1/2009 | Rodriguez et al. | |
| 7,807,166 B2 | 10/2010 | Rodriguez et al. | |
| 2005/0147605 A1 | 7/2005 | Rosen | |
| 2013/0280167 A1* | 10/2013 | Rodriguez | C07K 16/18 424/9.1 |
| 2014/0065167 A1 | 3/2014 | Rodriguez et al. | |

FOREIGN PATENT DOCUMENTS

| | | |
|---|---|---|
| WO | 01/85797 A1 | 11/2001 |
| WO | 2004/110355 A2 | 12/2004 |
| WO | 2006/004988 A2 | 12/2006 |
| WO | 2012/054077 A2 | 4/2012 |
| WO | 2013158748 A1 | 10/2013 |

OTHER PUBLICATIONS

Warrington et al (J Neurosc Res 85: 967-976, 2007).*
Manning et al (J Neurosc 28: 6670-6678, 2008).*
Hatzidaki et al (Acta Obstet Gynec Scand 88: 110-5, 2009—abstract only).*
Watzlawik et al, PLOS ONE 10: 1-24, May 28, 2015.*
Schiffmann and van der Knaap, Neurology, Feb. 24, 2009;72(8):750-9 (Year: 2009).*
Steenweg et al., Brain, Sep. 27, 2010; 133(10): 2971-2982 (Year: 2010).*
Volpe, J. J., 2001. Neurobiology of periventricular leukomalacia in the premature infant. Pediatric research. 50, 553-62.
Volpe, J.J., 2003. White matter injury of the premature infant—More common than you think. Pediatrics. 112, 176-180.
Folkerth, R.D., 2005. Neuropathologic Substrate of Cerebral Palsy. J Child Neurol 20, 940-49.
Barkovich, A.J. et al. 1999. Proton MR spectroscopy for the evaluation of brain injury in asphyxiated, term neonates. Am J Neuroradiol. 20, 1399-1405.
Barkovich, A.J., et al., 2006. MR imaging, MR spectroscopy, and diffusion tensor imaging of sequential studies in neonates with encephalopathy. Am J Neuroradiol. 27, 533-47.
Miller, S.P. et al., 2005. Patterns of brain injury in term neonatal encephalopathy. J Pediatrics. 146, 453-60.
Steinman, K.J., et al., 2009. Neonatal watershed brain injury on MRI correlates with verbal IQ at four years. Pediatrics. 123(3), 1025-30.

(Continued)

*Primary Examiner* — Kimberly Ballard
*Assistant Examiner* — Stacey N MacFarlane
(74) *Attorney, Agent, or Firm* — Hoffmann & Baron, LLP

(57) ABSTRACT

The invention provides methods for the treatment of neonatal hypoxia and associated white matter disease or injury, particularly in infant, including neonatal, animals, particularly Periventricular Leukomalacia (PVL) comprising administering one or more CNS reactive antibody, particularly selected from IgM12, IgM22, IgM42 and IgM46. Compositions for use in treatment of white matter disease or injury in infants, particularly PVL are provided. The invention provides methods for alleviation of neuromotor or neurodevelopmental deficits associated with neonatal hypoxia and associated with white matter injury, including PVL, in an infant.

15 Claims, 16 Drawing Sheets
Specification includes a Sequence Listing.

(56) References Cited

OTHER PUBLICATIONS

Skoff, R.P., et al., 2001. Hypoxic-ischemic injury results in acute disruption of myelin gene expression and death of oligodendroglial precursors in neonatal mice. Int J Devi Neuroscience. 19, 197-208.

Back, S. A., et al., 2002. Selective vulnerability of late oligodendrocyte progenitors to hypoxia-ischemia. The Journal of Neuroscience 22, 455-63.

Liu, Y, et al., 2002. Hypoxic-ischemic oligodendroglial injury in neonatal rat brain. Pediatric Res. 51, 25-33.

Shankaran, S., et al., 2005. Whole-body hypothermia for neonates with hypoxic-ischemic encephalopathy. N Eng J Med. 353, 1574-84.

Miller, S.P., et al., 2007. Abnormal brain development in newborns with congenital heart disease. N Eng J Med. 357:1928-38.

Kinney, H.C., et al., 2005. Hypoxic-ischemic brain injury in infants with congenital heart disease dying after cardiac surgery. Acta Neuropathol 1 10, 563-78.

Warrington AE, et al. (2004) Neuron-binding human monoclonal antibodies support central nervous system neurite extension. J Neuropathol Exp Neurol 63(5):461-473.

Warrington AE, et al. (2000) Human monoclonal antibodies reactive to oligodendrocytes promote remyelination in a model of multiple sclerosis. Proceedings of the National Academy of Sciences of the United States of America 97 (12):6820-6825.

Mitsunaga YB et al. (2002) Faseb J 16:1325-1327.

Bieber AJ et al. (2002) Glia 37:241-249. Human antibodies accelerate the rate of remyelination following lysolecithin-induced demyelination in mice.

Warrington AE, et al. (2007) A recombinant human IgM promotes myelin repair after a single, very low dose. J Neurosci Res 85(5):967-976 (in eng).

Pirko I, et al. (2004) A human antibody that promotes remyelination enters the CNS and decreases lesion load as detected by T2-weighted spinal cord MRI in a virus-induced murine model of MSFaseb J 18(13): 1577-1579.

Rice JE, 3rd, Vannucci RC, & Brierley JB (1981) The influence of immaturity on hypoxic-ischemic brain damage in the rat. Ann Neurol 9(2): 131-141.

Vanucci and Vanucci (2005) Dev Neurosci 27:81-86. Perinatal hypoxia-ischem: a brain damage: evolution of an animal model.

Back et al. (2006) Ann Neurol 60:696-705. Protective effects of caffeine on chronic hypoxia-induced perinatal white matter injury.

Fagel et al. (2006) Exp Neurol 199:77-91. Cortical neurogenesis enhanced by chronic perinatal hypoxia.

Chahboune et al. (2009) Cereb Cortex 19:2891-2901.

Scafidi et al. (2009) Int J Dev Neurosci 27:863-871.

Cai et al. (1998) Brain Res Dev Brain Res 109:265-269.

Miller, S.P et al., 2002. Predictors of 30-month outcome after perinatal depression: Role of proton MRS and socioeconomic factors Pediatr Res 52, 71-77.

Drobyshevsky et al. (2005) J Neurosci 25:5988-5997.

McClure et al. (2008) J Cereb Blood Flow Metab 5:995-1008.

Silbereis et al. (2 010) Dis Models & Meeh 3 :678-688.

Fagel, D. M., et al., 2009. Fgfrl is required for cortical regeneration and repair after perinatal hypoxia. The Journal of neuroscience: the official journal of the Society for Neuroscience 29, 1202-11.

Jablonska, B., et al., 2012. Oligodendrocyte regeneration after neonatal hypoxia requires FoxOI-mediated p27Kipl expression. The Journal of neuroscience: the official Journal of the Society for Neuroscience. 32, 14775-93.

Turner, C. P., et al., 2003. AI adenosine receptors mediate hypoxia-induced ventriculomegaly. Proceedings of the National Academy of Sciences of the United States of America. 100, 11718-22.

Weiss, J., et al., 2004. Neonatal hypoxia suppresses oligodendrocyte Nogo-A and increases axonal sprouting in a rodent model for human prematurity. Experimental Neurology 189, 141-9.

Scafidi J, et al. (2014) Intranasal epidermal growth factor treatment rescues neonatal brain injury. Nature 506 (7487):230-234.

Li, Q., et al, 2009. Strain differences in behavioral and cellular responses to perinatal hypoxia and relationships to neural stem cell survival and self-renewal: Modeling the neurovascular niche. The American journal of pathology. 175, 2133-46.

Miller DJ, Sanborn KS, Katzmann JA, & Rodriguez M (1994) Monoclonal autoantibodies promote central nervous system repair in an animal model of multiple sclerosis. J Neurosci 14(10):6230-6238.

Back, S. A., et al., 2001. Late oligodendrocyte progenitors coincide with the developmental window of vulnerability for human perinatal white matter injury. The Journal of Neuroscience 21, 1302-12.

Back, S. A., et al., 2005. Selective vulnerability of preterm white matter to oxidative damage defined by F2-isoprostanes. Annals of Neurology 58, 108-20.

Gluckman, P.D., et al., 2005. Selective head cooling with mild systemic hypothermia after neonatal encephalopathy: multicentre randomized trial. The Lancet. 365,663-70.

\* cited by examiner

FIGURE 1
A
B
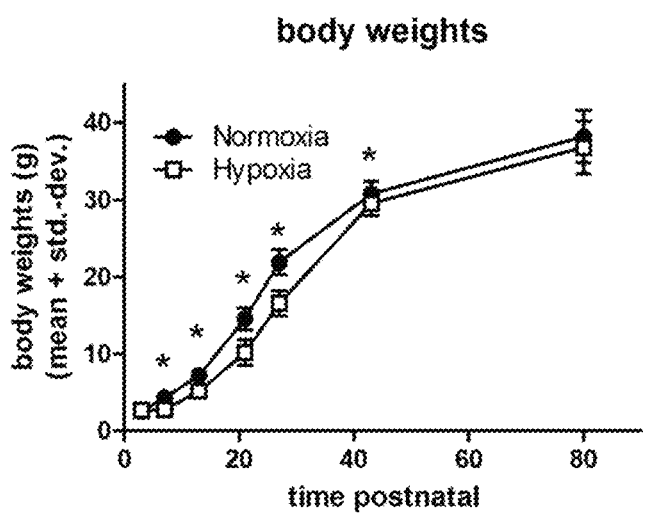
C
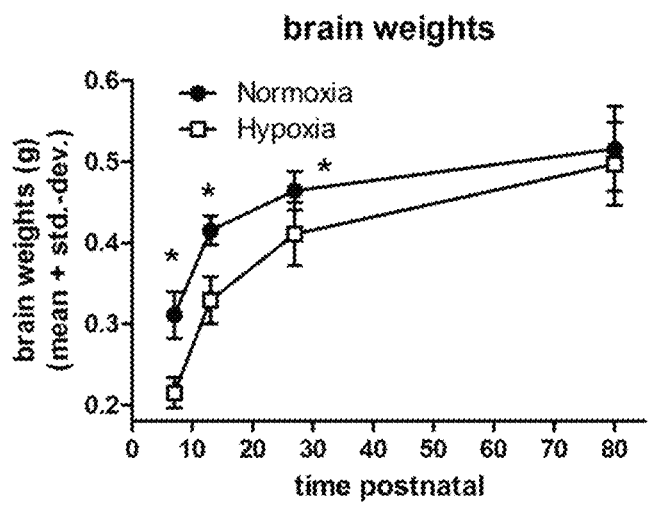

FIGURE 3 (cont)
B
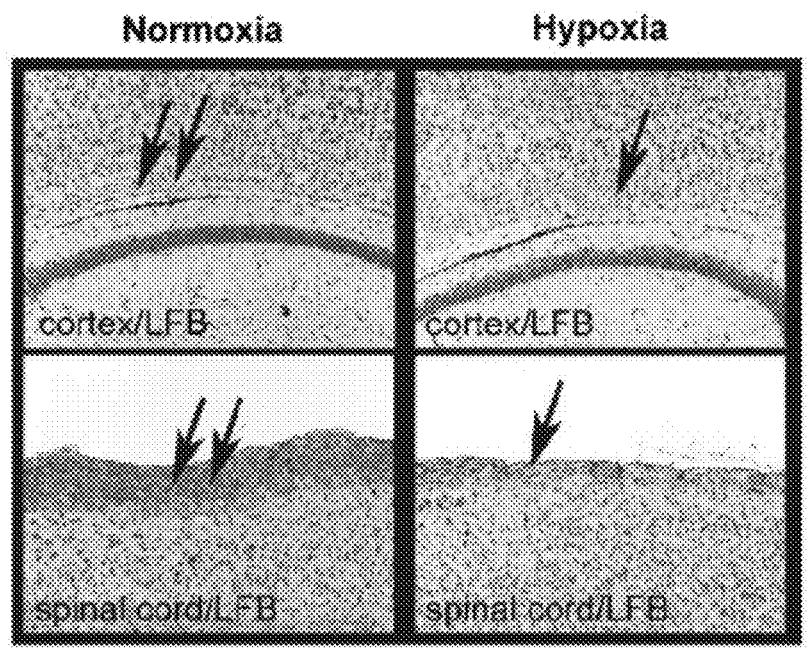
C
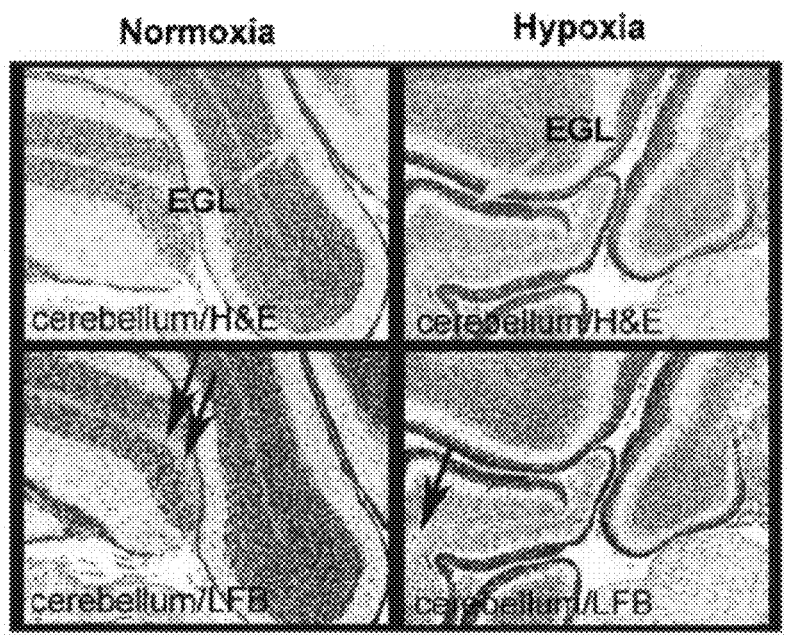

FIGURE 10

IgM12

V$_H$ heavy chain variable region

```
caggtgcagctgcaggagtcgggcccaggactgctgaagccttcggagaccctgtcctc
 Q  V  Q  L  Q  E  S  G  P  G  L  L  K  P  S  E  T  L  S  L
acatgcactgtctctggtggttccgtcagtctttactactggagctggatccggcagtcc
 T  C  T  V  S  G  G  S  V  S  L  Y  Y  W  S  W  I  R  Q  S
ccagggaaggaaccggagtggattggatatatctattccagtggaagcaccgattacaac
 P  G  K  E  P  E  W  I  G  Y  I  Y  S  S  G  S  T  D  Y  N
Ccttccctcaggagtcgagtcaccatatcactggacacgtcaaacaaccggttttcccta
 P  S  L  R  S  R  V  T  I  S  L  D  T  S  N  N  R  F  S  L
aacctgaggtctgtgaccgccgcagatacagcggtctattggtgtgcgagaagtgcgtca
 N  L  R  S  V  T  A  A  D  T  A  V  Y  W  C  A  R  S  A  S
attaggggctggttcgaccctggggccagggaaccctggtcaccgtctcctca
 I  R  G  W  F  D  P  W  G  Q  G  T  L  V  T  V  S  S
```

V$_L$ light chain variable region

```
gacatccagatgacccagtctccatcctccttgtctgcgtctgtaggagacaga
 D  I  Q  M  T  Q  S  P  S  S  L  S  A  S  V  G  D  R
Gtcaccatcacttgccgggcaagtcagagtattagtagttatctaaattggtatcagcag
 V  T  I  T  C  R  A  S  Q  S  I  S  S  Y  L  N  W  Y  Q  Q
aaaccagggaaagcccctaaggtcctgatctatgctgcatccactttgcgaagtggggtc
 K  P  G  K  A  P  K  V  L  I  Y  A  A  S  T  L  R  S  G  V
ccgtcaaggttcagtggcagtggatctgggacagatttcactctcagcgtcagcagtctg
 P  S  R  F  S  G  S  G  S  G  T  D  F  T  L  S  V  S  S  L
caacctgaagattttgcaacttactactgtcaacagagttaccatacccgtggacgttc
 Q  P  E  D  F  A  T  Y  Y  C  Q  Q  S  Y  H  T  P  W  T  F
ggtcaggggaccaaggtggaa
 G  Q  G  T  K  V  E
```

FIGURE 11

IGM22

V$_H$ heavy chain variable region

```
caggtgcagctggtggagtctggggggggcgtggtccagcctggg aggtccctgagactc
Q   V   Q   L   V   E   S   G   G   G   V   V   Q   P   G   R   S   L   R   L tcctgtgcagcctctggattcaccttcagtagctctggcatgcactgggtccgccaagct
S   C   A   A   S   G   F   T   F   S   S   S   G   M   H   W   V   R   Q   A ccaggcaaggggctggagtgggtggca^(g/a)t^(t/c)atttcatatgatggaagtaggaaatactat
P   G   K   G   L   E   W   V   A   V/I   I   S   Y   D   G   S   R   K   Y   Y gcagactccgtgaagggccgattcaccatctccagagacaactccaagaacactctctat
A   D   S   V   K   G   R   F   T   I   S   R   D   N   S   K   N   T   L   Y ctgcaaatgaacagcctgacggctga^(g/c)gacacggctgtgtattattgtgcgaaggagtg
L   Q   M   N   S   L   T   A   D/E   D   T   A   V   Y   Y   C   A   K   G   V actggtagtccgacgcttgactactggggccagggaaccctggtcaccgtctcctcg
T   G   S   P   T   L   D   Y   W   G   Q   G   T   L   V   T   V   S   S
```

V$_L$ light chain variable region

```
cagtctgtgttgacggagccgccttcagtgtctgctgccccaggacagaaggtcaccatc
Q   S   V   L   T   Q   P   P   S   V   S   A   A   P   G   Q   K   V   T   I tcctgctctggaagcagctccaacattggcaataattttgtatcctggtaccagcaactc
S   C   S   G   S   S   S   N   I   G   N   N   F   V   S   W   Y   Q   Q   L ccaggaacagccccca^(a/g)actcctcatttatgacattactaagcgaccctcagggattcct
P   G   T   A   P   R/K   L   L   I   Y   D   I   T   K   R   P   S   G   I   P gaccgattctctggctccaagtctggcacgtcagccaccctgggcatcaccggactccag
D   R   F   S   G   S   K   S   G   T   S   A   T   L   G   I   T   G   L   Q actggggacgaggccgattattactgcg^(g/a)aacatgggatagcagcctgagtgctgtggta
T   G   D   E   A   D   Y   Y   C   G/E   T   W   D   S   S   L   S   A   V   V ttcggcggggggaccaagctgaccgtcctaggtcagcccaag
F   G   G   G   T   K   L   T   V   L   G   Q   P   K
```

FIGURE 12

IgM42

V$_H$ heavy chain variable region

```
gaggtgcagctgttggagtctgggggaggcttggtacagcctggggggtccctgagactctcc
 E   V   Q   L   L   E   S   G   G   G   L   V   Q   P   G   G   S   L   R   L   S tgtgcagcctctggattcacctttagcacctatgccatgagctgggtccgccaggctcca
 C   A   A   S   G   F   T   F   S   T   Y   A   M   S   W   V   R   Q   A   P ggggaggggctggagtgggtctcagatattaatgttggtggtgttaccacatactacgca
 G   E   G   L   E   W   V   S   D   I   N   V   G   G   V   T   T   Y   Y   A gactccgtgaagggccggttcaccatctccagagacaattccaagaacacgctgtatcta
 D   S   V   K   G   R   F   T   I   S   R   D   N   S   K   N   T   L   Y   L caaatgaacagcctgagagtagaggacacggccatgtattactgtgtgaggcggtccggg
 Q   M   N   S   L   R   V   E   D   T   A   M   Y   Y   C   V   R   R   S   G cccgatcgcaactcgtcgcccgctgacttctggggccagggatccctggtcatcgtctcc
 P   D   R   N   S   S   P   A   D   F   W   G   Q   G   S   L   V   I   V   S tcagggagtgcatccgccccaacccttttccccctcgtc
 S   G   S   A   S   A   P   T   L   F   P   L   V
```

V$_L$ light chain variable region

```
gacatccagatgacccagtctccatcctccctg
 D   I   Q   M   T   Q   S   P   S   S   L tctgcatctgtaggagacagagtcaccatcacttgccgggcgagtcagggcattggcaat
 S   A   S   V   G   D   R   V   T   I   T   C   R   A   S   Q   G   I   G   N tatttagcctggtatcagcagaaaccagggaaagttcctaaactcctgatctatactaca
 Y   L   A   W   Y   Q   Q   K   P   G   K   V   P   K   L   L   I   Y   T   T tccattttgcaatcaggggtcccatctcgattcagtggcagtggatctgggacagatttc
 S   I   L   Q   S   G   V   P   S   R   F   S   G   S   G   S   G   T   D   F actctcaccatcagcagcctgcagcctgaagatttttgcaacttattactgtcaaaaatat
 T   L   T   I   S   S   L   Q   P   E   D   F   A   T   Y   Y   C   Q   K   Y aacagtgccccgcggacgttcggccaagggaccagggtggac
 N   S   A   P   R   T   F   G   Q   G   T   R   V   D
```

FIGURE 13

IgM46

V$_H$ heavy chain variable region

```
gaggtgcagctggtggagtctgggggaggcttggtccagcctggggggtccctgagactc
E   V   Q   L   V   E   S   G   G   G   L   V   Q   P   G   G   S   L   R   L tcctgtgcagcctctggattcacctttagtagctattggatgacctgggtccgccaggct
S   C   A   A   S   G   F   T   F   S   S   Y   W   M   T   W   V   R   Q   A ccagggaaggggctggagtgggtggccaacataaagaaagatggaagtgagaaatcctat
P   G   K   G   L   E   M   V   A   N   I   K   K   D   G   S   E   K   S   Y gtggactctgtgaagggccgattcaccacctccagagacaacgccaagaactcactgtat
V   D   S   V   K   G   R   F   T   T   S   R   D   N   A   K   N   S   L   Y ctgcaaatgaacagcctgagagccgaggacacggctgtgtattactgtgcgagacccaat
L   Q   M   N   S   L   R   A   E   D   T   A   V   Y   Y   C   A   R   P   N tgtggtggtgactgctatttaccatggtacttcgatctctggggccgtggcaccctggtc
C   G   G   D   C   Y   L   P   W   Y   F   D   L   W   G   R   G   T   L   V actgtctcctca
T   V   S   S
```

V$_L$ light chain variable region

```
gacatcgtgatgacccagtctccagactccctggctgtgtctctgggcgagagggccacc
D   I   V   M   T   Q   S   P   D   S   L   A   V   S   L   G   E   R   A   T atcaactgcaagtccagccagagtgttttatacagctccaacaataagaactacttagct
I   N   C   K   S   S   Q   S   V   L   Y   S   S   N   N   K   N   Y   L   A tggtaccagcagaaaccaggacagcctcctaaactactcatttactgggcatctacccgg
W   Y   Q   Q   K   P   G   Q   P   P   K   L   L   I   Y   W   A   S   T   R gaatccggggtccctgaccgattcagtggcagcgggtctgggacagatttcactctcacc
E   S   G   V   P   D   R   F   S   G   S   G   S   G   T   D   F   T   L   T atcagcagcctgcaggctgaagatgtggcagtttattactgtcagcaatattataatact
I   S   S   L   Q   A   E   D   V   A   V   Y   Y   C   Q   Q   Y   Y   N   T cctcaggcgttcggccaagggaccaaggtggaaatcaaacgaactgtggctgcaccatct
P   Q   A   F   G   Q   G   T   K   V   E   I   K   R   T   V   A   A   P   S gtcttc
V   F
```

TREATMENT OF NEONATAL HYPOXIA INCLUDING IMPAIRMENTS OR EFFECTS THEREOF

CROSS REFERENCE TO RELATED APPLICATIONS

The present application is a National Stage Application claiming the priority of PCT Application No. PCT/US2015/059630 filed Nov. 6, 2015, which in turn, claims priority from U.S. Provisional Application Ser. No. 62/076,669 filed Nov. 7, 2014. Applicants claim the benefits of 35 U.S.C. § 120 as to the PCT Application and priority under 35 U.S.C. § 119 as to the said U.S. Provisional application, and the entire disclosures of both applications are incorporated herein by reference in their entireties.

This application claims priority to U.S. provisional Application 62/076,669 filed Nov. 7, 2014, the subject matter of which is hereby incorporated by reference in its entirety.

FIELD OF THE INVENTION

The present invention relates to methods for the treatment of neonatal hypoxia and associated white matter disease or injury, particularly Periventricular Leukomalacia (PVL), particularly in infants, including neonates, using antibodies that bind to the CNS.

BACKGROUND OF THE INVENTION

The rate of cerebral palsy (CP) has increased steadily over the past few decades to its current incidence of more than 3 per 1000 live births, with 800,000 Americans affected as of 2009 (Titomanlio L et al., 2011). Much of this increase is due to the improving rate of survival among two distinct populations of critically ill neonates: those born prematurely and at very low birth weight (Silbereis et al., 2010), and those born at term who are affected by intrapartum hypoxia-ischemia (birth asphyxia). Over the course of infancy and childhood, many of these infants display motor deficits and cognitive-behavioral disturbances that correlate closely with the neuropathological changes in the cerebral white matter (Ferreiro, 2004; Folkerth, 2005; Hack et al., 2005; Volpe, 2001; Volpe, 2001a; Volpe, 2003; Volpe, 2008; Woodward et al., 2006).

Periventricular Leukomalacia (PVL) is characterized by the death of the white matter of the brain. It can affect fetuses or newborns, and premature babies are at the greatest risk of the disorder. PVL often leads to nervous system and developmental problems in growing babies, particularly during the first or second year of life and may result in cerebral palsy. Researchers have identified a period of selective vulnerability in the developing fetal human brain, between 26 and 34 weeks of gestation, particularly before 32 weeks gestation, in which Periventricular white matter is particularly sensitive to insults and injury. PVL is caused by a lack of oxygen or blood flow to the Periventricular area of the brain, which results in the death or loss of brain tissue. PVL is diagnosed by ultrasound or MRI.

White matter disease or injury in the form of PVL seen in premature infants manifests as diffuse hypomyelination and reduced white matter volume in the cerebral cortex (Volpe, 2001). These abnormalities appear to result from the selective death or disordered development of the preoligodendrocyte (pre-OL) during episodes of hypoxia-ischemia (H-I) (Silbereis et al., 2010). PVL manifests an overabundance of Olig-2-positive OL progenitor cells (OPCs) or immature OLs and depletion of mature MBP-positive OLs (Back et al., 2001; Back et al., 2005; Billiards et al., 2008; Buser et al., 2012). Given the sensitivity of the OL lineage to hypoxic stress (Weiss et al., 2004), the episodic recurrence of hypoxia-ischemia in extremely low birth weight (ELBW) neonates is a leading contributor to alterations in the OL lineage progression and PVL (Rezaie and Dean, 2002; Riddle et al., 2006; Volpe, 2001; Welin et al., 2005). White matter injury is also a prominent feature of PVL in term infants affected by intrapartum hypoxia-ischemia, wherein the intervascular zone of the deep periventricular region (the so-called "watershed") is primarily affected (Volpe, 2001a; Folkerth, 2005). In this population, white matter injury has been well characterized by various magnetic resonance imaging modalities, with abnormal findings correlating with long-term neurodevelopmental disability (Barkovich, 1999; Miller SP, 2005; Barkovich 2006; Miller, 2002; Steinman, 2009). At a cellular level, the injury and death of OL precursor cells underlies the decreased expression of mature myelin proteins and the resulting abnormalities of the cerebral white matter (Skoff, 2001; Back, 2002; Liu, 2002). Even utilizing therapeutic hypothermia, a large percentage of affected infants manifest clinical signs of this neuropathology over the long term (Shankaran, 2005; Gluckman, 2005). Similarly, there are no therapies on the horizon for neonates undergoing complex congenital heart surgery, a population known to be at high risk for hypoxic-ischemic white matter disease both pre- and post-operatively (Miller, 2007; Kinney, 2005).

At present there are no therapies available to treat white matter disease or injury in infants, including neonates, particularly PVL, particularly in low birth weight or premature infants.

The citation of references herein shall not be construed as an admission that such is prior art to the present invention.

SUMMARY OF THE INVENTION

The invention provides methods for treating white matter disease or injury in infants, including neonates, particularly Periventricular Leukomalacia (PVL), by administering one or more CNS binding antibody. In aspects of the methods of the invention, the antibody or antibodies serve to treat myelin alteration associated with white matter disease or injury; serve to maintain myelin quantity and quality in instances of white matter disease or injury; serve to alleviate neonatal encephalopathy, in particular neonatal encephalopathy associated with white mater disease or injury; and/or serve to alleviate neuromotor deficits associated with neonatal hypoxia, particularly including PVL.

In accordance with the present invention, it has been discovered that antibodies, particularly monoclonal antibodies, particularly recombinant antibodies, with particular effectiveness and binding capability in the CNS, are useful in methods of treating white matter injury in infants, including neonates, particularly PVL. In particular, methods and uses are provided whereby specific recombinant antibodies, including recombinant fully human antibodies, are capable of treating deficits and alterations associated with or the result of white matter disease or injury, particularly PVL, in infants. In particular, methods and uses are provided whereby specific recombinant antibodies, including recombinant fully human antibodies, are capable of treating deficits and alterations associated with or the result of white matter disease or injury, particularly PVL, in neonates. In an aspect of the invention, methods are provided to treat or reduce neuromotor and/or neurodevelopmental deficits associated with white matter injury in infants, including neuromotor and/or neurodevelopmental deficits associated with PVL. In an aspect of the invention the antibody(ies) are relevant and effective particularly in methods in premature or low birth weight neonates; neonates who have suffered oxygen loss or deprivation during or immediately/shortly after birth; and infants undergoing complex congenital heart surgery, particularly when cardioplegia and cardiopulmonary bypass is required.

The present studies demonstrate that when CNS-binding monoclonal antibodies, particularly HIgM12 and , HIgM22, alone or in combination, are administered to mammals, particularly infants who have suffered hypoxia, particularly infants, including neonates, demonstrating white matter injury, particularly PVL, a significant improvement of neuromotor function of the mammals results. In a particular aspect, administration of one or more antibody selected from HIgM12, HIgM22, HIgM42, or HIgM46 protects myelin integrity in infant mammals who have suffered hypoxia. In a particular aspect, administration of one or more antibody selected from HIgM12, HIgM22, HIgM42, or HIgM46 alleviates neuromotor deficits in infant mammals who have suffered hypoxia, particularly neonates or infants demonstrating white matter injury, particularly PVL. By way of example, CNS binding monoclonal antibodies, such as HIgM12, may bind neurons. By way of example, CNS binding antibodies such as HIgM22, may bind oligodendrocytes.

In an aspect of the invention a recombinant or synthetic antibody applicable in the methods comprises the variable region CDR sequences set out in FIG. 10 and/or 11. Antibody IgM12 comprises heavy chain CDR sequences CDR1 GGSVSLYY (SEQ ID NO:1), CDR2 GYIYSSGST (SEQ ID NO:2) and CDR3 ARSASIRGWFD (SEQ ID NO:3). Antibody IgM12 comprises light chain CDR sequences CDR1 QSISSY (SEQ IDNO: 4), CDR2 AAS (SEQ ID NO:5) and CDR3 QQSYHTPW (SEQ ID NO:6), as set out in FIG. 10. Antibody IgM22 comprises heavy chain CDR sequences CDR1 SSGMH (SEQ ID NO: 11), CDR2 V(I)ISYDGSRKYYADSVKG (SEQ ID NO:12) and CDR3 GVTGSPTLDY (SEQ ID NO:13), and light chain CDR sequences CDR1 SGSSSNIGNNFVS (SEQ ID NO: 14), CDR2 DITKRPS (SEQ ID NO:15) and CDR3 G(E)TWDSSLSAVV (SEQ ID NO: 16), as set out in FIG. 11. In another embodiment of the invention antibody IgM22 comprises heavy chain CDR sequences CDR1 SSGMH (SEQ ID NO: 11), CDR2 VAIISYDGSRKYYADSVKG (SEQ ID NO:55) and CDR3 GVTGSPTLDY (SEQ ID NO:13), and light chain CDR sequences CDR1 SGSSSNIGNNFVS (SEQ ID NO: 14), CDR2 DITKRPS (SEQ ID NO:15) and CDR3 CETWDSSLSAVV (SEQ ID NO: 56). Accordingly, recombinant antibodies which are based on the CDRs of the antibody(ies) identified herein will be useful in the methods of the invention.

In one embodiment, a recombinant IgM12 antibody comprises heavy chain CDR sequences SEQ ID NO: 1-3 and light chain CDR sequences SEQ ID NO: 4-6. In one embodiment, a recombinant IgM22 antibody comprises heavy chain CDR sequences SEQ ID NO: 11-13 and light chain CDR sequences SEQ ID NO: 14-16. In another embodiment, a recombinant IgM22 antibody comprises heavy chain CDR sequences SEQ ID NO: 11, 55 and 13, and light chain CDR sequences SEQ ID NO: 14, 15 and 56. The recombinant antibody is preferably an IgM antibody. In some embodiments the J chain of the recombinant IgM antibody is a human J chain (e.g., SEQ ID NO: 54). In some embodiments, the J chain of the recombinant antibody is a non-human J chain, for example a murine e J chain (e.g., SEQ ID NO: 53). In an aspect of the invention a recombinant or synthetic antibody applicable in the methods comprises the variable region CDR sequences set out in FIG. 12 and/or 13. Antibody IgM42 comprises heavy chain CDR sequences CDR1 GFTFSTYA (SEQ ID NO:21), CDR2 INVGGVTT (SEQ ID NO:22) and CDR3 VRRSGPDRNSSPADF (SEQ ID NO:23). Antibody IgM42 comprises light chain CDR sequences CDR1 QGIG (SEQ ID NO: 24), CDR2 TTS (SEQ ID NO:25) and CDR3 QKYNSAPRT (SEQ ID NO:26), as set out in FIG. 12. Antibody IgM46 comprises heavy chain CDR sequences CDR1 SGFTFSSYW (SEQ ID NO:31), CDR2 IKKDGSEK (SEQ ID NO:32) and CDR3 ARPNCGGDCYLPWYFD (SEQ ID NO:33), and light chain CDR sequences CDR1 QSVLYSSNNKNY (SEQ ID NO:34), CDR2 YWAS (SEQ ID NO:35) and CDR3 QQYYNTPQA (SEQ ID NO:36), as set out in FIG. 13. Accordingly, recombinant antibodies which are based on the CDRs of the antibody(ies) identified herein will be useful in the methods of the invention. In one embodiment, a recombinant IgM42 antibody comprises heavy chain CDR sequences SEQ ID NO: 21-23 and light chain CDR sequences SEQ ID NO: 24-26. In one embodiment a recombinant IgM46 antibody comprises heavy chain CDR sequences SEQ ID NO: 31-33 and light chain CDR sequences SEQ ID NO: 34-36. The recombinant antibody is preferably an IgM antibody. In some embodiments the J chain of the recombinant IgM antibody is a human J chain (e.g., SEQ ID NO: 54). In some embodiments, the J chain of the recombinant antibody is a non-human J chain, for example a murine J chain (e.g., SEQ ID NO: 53).

The invention thus provides methods for treating the impairments and effects of neonatal hypoxia in infants, particularly white matter disease or injury, particularly PVL, wherein exemplary neuromotor deficits and/or and myelin alterations associated with PVL in infants are reduced, wherein one or more antibody or fragment comprising one or more of the following sequences is administered: (a) the variable heavy chain amino acid CDR domain sequences CDR1 GGSVSLYY (SEQ ID NO:1), CDR2 GYIYSSGST (SEQ ID NO:2) and CDR3 ARSASIRGWFD (SEQ ID NO:3), and light chain CDR sequences CDR1 QSISSY (SEQ IDNO: 4), CDR2 AAS (SEQ ID NO:5) and CDR3 QQSYHTPW (SEQ ID NO:6), as set out in FIG. 10; or (b) the variable heavy chain amino acid CDR domain sequences CDR1 SSGMH (SEQ ID NO: 11), CDR2 V(I)ISYDGSRKYYADSVKG (SEQ ID NO:12) and CDR3 GVTGSPTLDY (SEQ ID NO:13), and light chain CDR sequences CDR1 SGSSSNIGNNFVS (SEQ ID NO:14), CDR2 DITKRPS (SEQ ID NO:15) and CDR3 G(E)TWDSSLSAVV (SEQ ID NO: 16), as set out in FIG. 11; (c) the variable heavy chain amino acid CDR sequences CDR1 GFTFSTYA (SEQ ID NO:21), CDR2 INVGGVTT (SEQ ID NO:22) and CDR3 VRRSGPDRNSSPADF (SEQ ID NO:23), and light chain CDR sequences CDR1 QGIG (SEQ ID NO:24), CDR2 TTS (SEQ ID NO:25) and CDR3 QKYNSAPRT (SEQ ID NO:26); and (d) the variable heavy chain amino acid CDR sequences CDR1 SGFTFSSYW (SEQ ID NO:31), CDR2 IKKDGSEK (SEQ ID NO:32) and CDR3 ARPNCGGDCYLPWYFD (SEQ ID NO:33), and light chain CDR sequences CDR1 QSVLYSSNNKNY (SEQ ID NO:34), CDR2 YWAS (SEQ ID NO:35) and CDR3 QQYYNTPQA (SEQ ID NO:36). By way of example a recombinant IgM12 antibody, may specifically comprise heavy chain CDR sequences SEQ ID NO: 1-3 and light chain CDR sequences SEQ ID NO: 4-6. A recombinant IgM22 antibody may specifically comprise heavy chain CDR sequences SEQ ID NO: 11-13 and light chain CDR sequences SEQ ID NO: 14-16. A recombinant IgM22 antibody, may also specifically comprise heavy chain CDR sequences SEQ ID NO: 11, 55 and 13 and light chain CDR sequences SEQ ID NO: 14, 15 and 56. A recombinant IgM42 antibody, including denoted HIgM42, may specifically comprise heavy chain CDR sequences SEQ ID NO: 21-23 and light chain CDR sequences SEQ ID NO: 24-26. A recombinant IgM46 antibody, including denoted HIgM46, may specifically comprise heavy chain CDR sequences SEQ ID NO: 31-33 and light chain CDR sequences SEQ ID NO: 34-36. The recombinant antibody is preferably an IgM antibody. In some embodiments the J chain of the recombinant IgM antibody is a human J chain (e.g., SEQ ID NO:54). In some embodiments, the J chain of the recombinant antibody is a non-human J chain, for example a murine J chain (e.g., SEQ ID NO:53).

Methods of the invention may comprise administration of at least one of the antibodies selected from the group of IgM12, IgM22, IgM42 and IgM46. In one embodiment IgM12 is administered. In another embodiment IgM22 is administered. In another embodiment IgM42 is administered. In another embodiment IgM46 is administered. Methods of the invention may comprise administration of more than one antibody or fragment, including combinations of any of antibody IgM12, IgM22, IgM42 and IgM46, in a particular aspect including combinations of IgM12 and IgM22. In a further such method, one or more of antibody IgM12 and/or of antibody IgM22 may be combined with another CNS reactive antibody, particularly including one or more of antibodies rHIgM42 and/or rHIgM46. Combinations of antibodies may be administered collectively or in series, and at various times and various amounts or concentrations. Bi-or multi-specific antibodies may be utilized. In a particular such aspect, antibody IgM12 and/or IgM22, and/or an antibody having the CDR region CDR1, CDR2 and CDR3 sequences of IgM12 and/or IgM22, is administered in combination with antibody IgM42 and/or IgM46 and/or an antibody having the CDR region CDR1, CDR2 and CDR3 sequences of IgM42 and/or IgM46, by combined administration or in series, separated by a short length of time or longer length of time, including by minutes, hours, days or weeks. In one such particular aspect of the method, one or more antibody 12 and/or 22 is administered in combination with antibody 42 and/or 46, by combined administration or in series for the treatment of a disease or condition involving infant PVL, and particularly including white matter injury during birth of an infant. In a preferred aspect, the antibody is an IgM antibody. In some embodiments the J chain of the IgM antibody is a human J chain (e.g., SEQ ID NO:54). In some embodiments, the J chain of the recombinant antibody is a non-human J chain, for example a murine J chain (e.g., SEQ ID NO:53).

In an aspect of the method of the invention, infants, including neonates, at risk of PVL-associated or correlated neuromotor or neurodevelopmental defects are administered one or more of said antibodies or fragments whereby the frequency or development of neuromotor or neurodevelopmental defects is reduced. The antibodies, fragments thereof and recombinant antibodies comprising the variable region sequences or CDR domain sequences according to the invention, may be utilized in methods or administered in compositions for protecting myelin integrity and preventing neuromotor deficits in the infants diagnosed with PVL or at risk of white matter disease or injury, particularly including at risk of PVL. Risk factors for white matter disease or injury, particularly including PVL, include but are not limited to low Apgar score, relatively long periods of ventilation and oxygen inhalation, a more persistent presence of apneic spells, prolonged or repetitive variable decelerations (irregular abrupt decreases in fetal heart rate) during labor, respiratory distress syndrome type I, infants born to mothers who suffered from preterm premature rupture of membranes, preeclampsia or clinical chorioamnionitis, very low birth weight premature infants (VLBWI), particularly those with chorioamnionitis or neonatal sepsis. A neonate or infant at risk of white matter disease or injury, particularly including PVL, by virtue of one or more risk factor may be administered the antibodies and compositions in accordance with an aspect of the method of the invention. In accordance with the methods, the antibody(ies) ameliorate one or more functional or assessable neurological or motor parameter, including an evaluable or scalable parameter, and/or an assayable myelin or brain protein which is associated with deficits of PVL. Administration of the antibody(ies) is effective to improve or ameliorate one or more of a symptom or parameter associated with PVL.

In accordance with the methods, recombinant antibody IgM12 may comprise the variable heavy chain sequence (SEQ ID NO: 7) and light chain sequence (SEQ ID NO: 8) as set out in FIG. 10. Recombinant antibody IgM22 may comprise the variable heavy chain sequence (SEQ ID NO: 17) and light chain sequence (SEQ ID NO: 18) as set out in FIG. 11. Recombinant IgM42 may comprise the heavy chain variable region sequence (SEQ ID NO: 27) and light chain variable region sequence (SEQ ID NO: 28) as set out in FIG. 12. Recombinant IgM46 may comprise the heavy chain variable region sequence (SEQ ID NO: 37) and light chain variable region sequence (SEQ ID NO: 38) as set out in FIG. 13.

In a particular embodiment, the methods of the invention utilize fully human recombinant antibodies, comprising human heavy chain variable region, constant region and human J chain. Fully human recombinant IgM12 antibodies may be utilized in the methods herein comprising human immunoglobulin heavy chain comprising variable region (SEQ ID NO: 1), or the CDRs thereof, a human constant region, and human J chain.

In further aspects, the invention provides methods utilizing an isolated nucleic acid which comprises a sequence encoding one or more antibody as defined above and of use in the methods of the invention, or which comprise expressing said nucleic acids under conditions to bring about expression of said antibody, and recovering the antibody. In one such aspect, a nucleic acid encoding antibody heavy and light chain variable region sequence having the amino acid sequences as set out in FIG. 10, 11, 12 or 13 or an antibody having CDR domain sequences as set out in FIG. 10, 11, 12 or 13 is utilized. In preferred aspects the invention methods may utilize nucleic acid encoding heavy chain (SEQ ID NO: 9) and light chain variable region sequence (SEQ ID NO: 10) of IgM12, and/or nucleic acid encoding heavy chain (SEQ ID NO:19) and light chain variable region sequence (SEQ ID NO: 20) of IgM22, and/or nucleic acid encoding heavy chain (SEQ ID NO: 29) and light chain variable region sequence (SEQ ID NO: 30) of IgM42, and/or nucleic acid encoding heavy chain (SEQ ID NO: 39) and light chain variable region sequence (SEQ ID NO: 40) of IgM46.

The invention includes diagnostic uses of CNS-binding recombinant antibodies in white matter injury, particularly under hypoxic conditions, in infants, including neonates, particularly in PVL. The diagnostic utility thus extends to the use of the antibodies of the present invention in assays and methods to characterize CNS white matter injury or damage in infants, including particularly infants diagnosed with or at risk of PVL. Thus, the antibodies may be utilized in assays and methods to assess myelin and/or to evaluate injury following neonatal hypoxia, or predicted or suspected white matter disease or injury, or PVL or in infants at risk of PVL. Thus radiolabelled antibodies and fragments thereof of the invention methods, are useful in in vitro diagnostics techniques and in in vivo radioimaging techniques in white matter injury in infants, including PVL. In a further aspect of the invention, radiolabelled antibodies and fragments thereof, particularly radioimmunoconjugates, are useful in radioimmunotherapy. In an in vivo aspect, the antibody or neuron binding fragment thereof is labeled and administered to the mammal after birth or after a period of hypoxia or after diagnosis of white matter disease or injury, or of PVL, for the purpose of locating injury or for assessing remaining damaged or injured white matter.

Other objects and advantages will become apparent to those skilled in the art from a review of the following description which proceeds with reference to the following illustrative drawings.

BRIEF DESCRIPTION OF THE DRAWINGS

FIG. 1A-1C. (A) is a diagram depicting the hypoxia-induced PVL model. Animals are reared in hypoxic conditions (10% oxygen) from postnatal day 3 (P3) through postnatal day 7 (P7) and then switched to normoxic conditions. P3 to P7 in mice corresponds to pre-term to term infancy gestational weeks 32-36 in humans. (B) and (C) depict body weight and brain weight measures (g) respectively of normoxia and hypoxia reared mice. Significant weight differences between hypoxic and normoxic animals are indicated by an asterisk (*).

FIG. 10 provides the amino acid and encoding nucleic acid sequences of the heavy chain variable region and the light chain variable region of human antibody HIgM12. The CDRs are underlined. Heavy chain CDRs1-3 are provided in SEQ ID NOs: 1-3 and light chain CDRs1-3 are provide in SEQ ID NOs: 4-6. Heavy chain variable region amino acid and encoding nucleic acid sequences are set out in SEQ ID NOs: 7 and 9, respectively. Light chain variable region amino acid and encoding nucleic acid sequences are set out in SEQ ID NOs: 8 and 10, respectively.

FIG. 11 provides the amino acid and encoding nucleic acid sequences of the heavy chain variable region and the light chain variable region of human antibody HIgM22. The CDRs are underlined. Heavy chain CDRs1-3 are provided in SEQ ID NOs: 11-13 and light chain CDRs1-3 are provide in SEQ ID NOs: 14-16. Heavy chain variable region amino acid and encoding nucleic acid sequences are set out in SEQ ID NOs: 17 and 19, respectively. Light chain variable region amino acid and encoding nucleic acid sequences are set out in SEQ ID NOs: 18 and 20, respectively.

FIG. 12 provides the amino acid and encoding nucleic acid sequences of the heavy chain variable region and the light chain variable region of human antibody HIgM42. The CDRs are underlined. Heavy chain CDRs1-3 are provided in SEQ ID NOs: 21-23 and light chain CDRs1-3 are provide in SEQ ID NOs: 24-26. Heavy chain variable region amino acid and encoding nucleic acid sequences are set out in SEQ ID NOs: 27 and 29, respectively. Light chain variable region amino acid and encoding nucleic acid sequences are set out in SEQ ID NOs: 28 and 30, respectively.

FIG. 13 provides the amino acid and encoding nucleic acid sequences of the heavy chain variable region and the light chain variable region of human antibody HIgM46. The CDRs are underlined. Heavy chain CDRs1-3 are provided in SEQ ID NOs: 31-33 and light chain CDRs1-3 are provide in SEQ ID NOs: 34-36. Heavy chain variable region amino acid and encoding nucleic acid sequences are set out in SEQ ID NOs: 37 and 39, respectively. Light chain variable region amino acid and encoding nucleic acid sequences are set out in SEQ ID NOs: 38 and 40, respectively.

DETAILED DESCRIPTION

Figure 2:
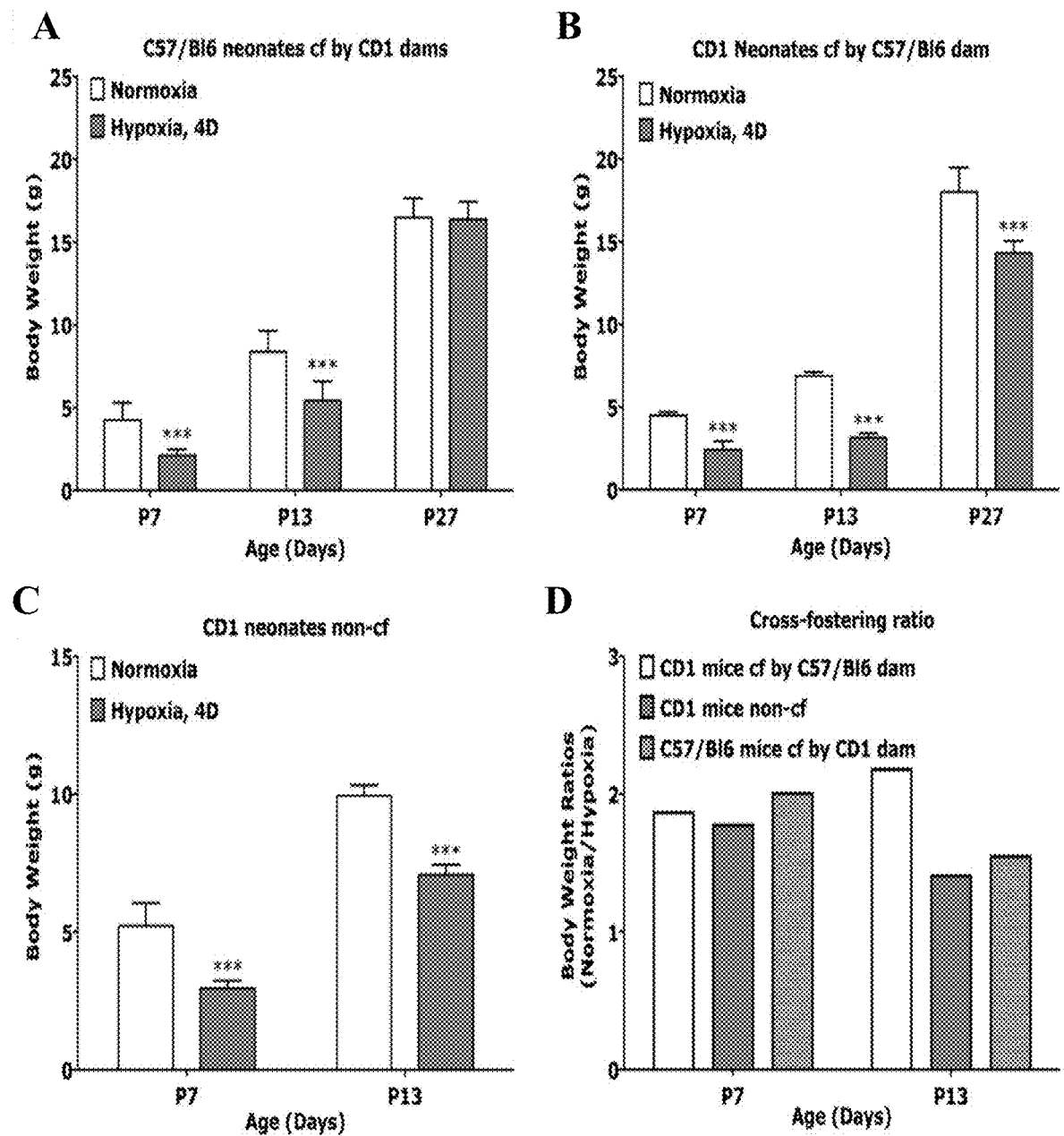
FIG. 2A-2D depicts Body weight (A-C) and body weight ratios (D) in cross-fostered (A, B) and non-cross-fostered (C) normoxic and hypoxic (P3→P7) CD1 and C57/B16 mice. Litter sizes in F were 6 neonatal mice per dam (non-cross-fostered CD1 mice: P7, n=23 normoxic, 18 hypoxic; P13, n=18 normoxic, 12 hypoxic mice; cross-fostered CD1 mice by C57/b16 dam: n=12 normoxic and 12 hypoxic mice for P7, P13 and P27; cross-fostered C57/B16 mice by CD1 dam: n=12 normoxic and 12 hypoxic mice for P7, P13 and P27). Data are shown as mean±std.-dev. * $p<0.001$;  $p<0.01$; *$p<0.05$.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The terms "IgM12 antibody", "antibody 12", "HIgM12", "sHIgM12", "rHIgM12", and any variants not specifically listed, may be used herein, and as used throughout the present application and claims refer to proteinaceous material including single or multiple proteins, and extends to those proteins having the amino acid sequence data described herein and presented in FIG. 10 and the profile of activities set forth herein and in the Claims. In particular IgM12 antibody, antibody 12, HIgM12, rHIgM12 particularly refer to polypeptides or antibodies or fragments, particularly recombinant antibodies or fragments, comprising sequence presented in FIG. 10, and particularly recombinant antibodies or fragments, comprising heavy chain variable region CDR sequences set out in SEQ ID NOS: 1-3 and light chain variable region CDR sequences set out in SEQ ID NOS: 4-6. IgM12 antibody, antibody 12, HIgM12, rHIgM12 includes antibody having the heavy chain variable region sequence of SEQ ID NO: 7 and the light chain variable region sequence of SEQ ID NO: 8. IgM12 includes an antibody, preferably an IgM antibody, having the heavy chain CDRs SEQ ID NO: 1-3 and the light chain CDRs SEQ ID NO: 4-6. IgM12 antibody includes an antibody having the heavy and light chain CDR sequences CDRs1-3 associated with the recombinant IgM12 antibody deposited with ATCC, particularly PTA-8932. IgM12 antibody includes an antibody having the heavy and light chain variable regions associated with the recombinant IgM12 antibody deposited with ATCC, particularly PTA-8932. IgM12 antibody includes an antibody having the heavy and light chains associated with the recombinant IgM12 antibody deposited with ATCC, particularly PTA-8932. In some embodiments the J chain of the recombinant IgM antibody is a human J chain (e.g., SEQ ID NO: 54). In some embodiments, the J chain of the recombinant antibody is a non-human J chain, for example a murine J chain (e.g., SEQ ID NO: 53).

The terms "IgM22 antibody", "antibody 22", "HIgM22", "sHIgM22", "rHIgM22", and any variants not specifically listed, may be used herein, and as used throughout the present application and claims refer to proteinaceous material including single or multiple proteins, and extends to those proteins having the amino acid sequence data described herein and presented in FIG. 11 and the profile of activities set forth herein and in the Claims. In particular IgM22 antibody, antibody 22, HIgM22, rHIgM22 particularly refer to polypeptides or antibodies or fragments, particularly recombinant antibodies or fragments, comprising sequence presented in FIG. 11, and particularly recombinant antibodies or fragments, comprising heavy chain variable region CDR sequences set out in SEQ ID NOS: 11-13 and light chain variable region CDR sequences set out in SEQ ID NOS: 14-16. IgM22 antibody, antibody 22, HIGM22, rHIgM22 includes antibody having the heavy chain variable region sequence of SEQ ID NO: 17 and the light chain variable region sequence of SEQ ID NO: 18. IgM22 includes an antibody, preferably an IgM antibody, having the heavy chain CDRs SEQ ID NO: 11-13 and the light chain CDRs SEQ ID NO: 14-16. CDR locations can be determined by systems known in the art (e.g., Kabat Numbering, Clothia Numbering). In another embodiment the IgM22 antibody includes antibodies, preferably IgM antibodies, comprising heavy chain CDRs SEQ ID NOs: 11, 55 and 13 and light chains CDRs SEQ ID NOs: 14, 15 and 56. IgM22 antibody includes an antibody having the heavy and light chain CDR sequences CDRs1-3 associated with the recombinant IgM22 antibody deposited with ATCC, particularly PTA-8671. IgM22 antibody includes an antibody having the heavy and light chain variable regions associated with the recombinant IgM22 antibody deposited with ATCC, particularly PTA-8671. IgM22 antibody includes an antibody having the heavy and light chains associated with the recombinant IgM22 antibody deposited with ATCC, particularly PTA-8671. In some embodiments the J chain of the recombinant IgM antibody is a human J chain (e.g., SEQ ID NO: 54). In some embodiments, the J chain of the recombinant antibody is a non-human J chain, for example a murine J chain (e.g., SEQ ID NO: 53).

The terms "IgM42 antibody", "antibody42", "HIgM42", "sHIgM42", "rHIgM42", and any variants not specifically listed, may be used herein, and as used throughout the present application and claims refer to proteinaceous material including single or multiple proteins, and extends to those proteins having the amino acid sequence data described herein and presented in FIG. 12 and the profile of activities set forth herein and in the Claims. In particular IgM42 antibody, antibody 42, HIgM42, rHIgM42 particularly refer to polypeptides or antibodies or fragments, particularly recombinant antibodies or fragments, comprising sequence presented in FIG. 12, and particularly refer to polypeptides or antibodies or fragments, particularly recombinant antibodies or fragments, comprising heavy chain variable region CDR sequences set out in SEQ ID NOS: 21-23 and light chain variable region CDR sequences set out in SEQ ID NOS: 24-26. IgM42 antibody, antibody 42, HIGM42, rHIgM42 includes antibody having the heavy chain variable region sequence of SEQ ID NO: 27 and the light chain variable region sequence of SEQ ID NO: 28. IgM42 includes an antibody, preferably an IgM antibody, having the heavy chain CDRs SEQ ID NO: 21-23 and the light chain CDRs SEQ ID NO: 24-26. In some embodiments the J chain of the recombinant IgM antibody is a human J chain (e.g., SEQ ID NO: 54). In some embodiments, the J chain of the recombinant antibody is a non-human J chain, for example a murine J chain (e.g., SEQ ID NO: 53).

The terms "IgM46 antibody", "antibody 46", "HIgM46", "sHIgM46", "rHIgM46", and any variants not specifically listed, may be used herein, and as used throughout the present application and claims refer to proteinaceous material including single or multiple proteins, and extends to those proteins having the amino acid sequence data described herein and presented in FIG. 13 and the profile of activities set forth herein and in the Claims. In particular IgM46 antibody, antibody 46, HIgM46, rHIgM46 particularly refer to polypeptides or antibodies or fragments, particularly recombinant antibodies or fragments, comprising sequence presented in FIG. 13. IgM46 antibody, antibody 46, HIgM46, rHIgM46 particularly refer to polypeptides or antibodies or fragments, particularly recombinant antibodies or fragments, comprising heavy chain variable region CDR sequences set out in SEQ ID NOS: 31-33 and light chain variable region CDR sequences set out in SEQ ID NOS: 34-36. IgM46 antibody, antibody 46, rHIgM46 includes antibody having the heavy chain variable region sequence of SEQ ID NO: 37 and the light chain variable region sequence of SEQ ID NO: 38. IgM46 includes an antibody, preferably an IgM antibody, having the heavy chain CDRs SEQ ID NO: 31-33 and the light chain CDRs SEQ ID NO: 34-36. In some embodiments the J chain of the recombinant IgM antibody is a human J chain (e.g., SEQ ID NO: 54). In some embodiments, the J chain of the recombinant antibody is a non-human J chain, for example a murine J chain (e.g., SEQ ID NO: 53).

The particular antibodies of use in the invention, including IgM12, IgM22, IgM42 and IgM46, and antibodies having the heavy and light chain variable region sequences provided herein, may preferably be IgM antibodies. The antibodies may preferably contain IgM constant regions. In some embodiments, the J chain of the antibody is a human J chain (e.g., SEQ ID NO: 54). In some embodiments, the J chain is a non-human J chain, particularly murine J chain (e.g., SEQ ID NO: 53).

Accordingly, proteins displaying substantially equivalent or altered activity to antibodies IgM12, IgM22, IgM42 and/or IgM46 are likewise contemplated. These modifications may be deliberate, for example, such as modifications obtained through site-directed mutagenesis, or may be accidental, such as those obtained through mutations in hosts that are producers of the complex or its named subunits. Also, the terms IgM12, IgM22, IgM42 and IgM46, etc., are intended to include within their scope proteins specifically recited herein as well as all substantially homologous analogs and allelic variations.

The amino acid residues described herein are preferred to be in the "L" isomeric form. However, residues in the "D" isomeric form can be substituted for any L-amino acid residue, as long as the desired fuctional property of immunoglobulin-binding is retained by the polypeptide. NH$_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552-59 (1969), abbreviations for amino acid residues are shown in the following Table of Correspondence:

TABLE OF CORRESPONDENCE

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "neonate" means and/or refers to a newborn child or mammal, particularly a newborn human. The term neonate is typically used in reference to a newborn or infant during approximately the first month or 4 weeks after birth, and may include any period beginning at birth up to approximately a month after birth.

An "infant" refers to a very young mammal, particularly a human, or a baby. The term infant is typically used in reference to a very young mammal during approximately the first year of age, and may include the period beginning at birth to approximately 1 year in age. The term infant(s) thus includes neonate(s).

The term "postnatal" relates to or refers to the period after childbirth, particularly including an infant immediately after or right after birth.

The term "prenatal" relates to or refers to before birth or during or relating to pregnancy. Pregnancy in a human lasts typically 38 weeks after conception or 40 weeks after the woman's/mother's last period.

A "premature" human infant refers to an infant born less than 37 weeks gestational age or an infant born before the developing organs are mature enough to allow normal human postnatal survival.

A "full term" human infant refers to an infant born at gestational age between 37 and 42 weeks.

A "postmature" human infant refers to an infant born after 42 weeks gestation.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 10-15, 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

It should be appreciated that also within the scope of the present invention are DNA sequences encoding antibodies of use and application in the present invention, particularly encoding antibody heavy chain and light chain CDRs of antibodies of the invention, which code for an antibody having the same amino acid sequence as set out in the SEQ IDs provided and designated herein, but which are degenerate to one or more of such SEQ ID or IDs. By "degenerate to" is meant that a different three-letter codon is used to specify a particular amino acid. It is well known in the art that the following codons can be used interchangeably to code for each specific amino acid:

| Amino Acid | Codons |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |
| Alanine (Ala or A) | GCU or GCG or GCA or GCG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |

```
Glutamic Acid (Glu or E)  GAA or GAG

Cysteine (Cys or C)       UGU or UGC

Arginine (Arg or R)       CGU or CGC or CGA or CGG or AGA or AGG

Glycine (Gly or G)        GGU or GGC or GGA or GGG

Tryptophan (Trp or W)     UGG

Termination codon         UAA (ochre) or UAG (amber) or UGA (opal)
```

It should be understood that the codons specified above are for RNA sequences. The corresponding codons for DNA have a T substituted for U.

Mutations can be made in sequences encoding one or more antibody, CDR sequences thereof, or SEQ ID of use or applicable in the invention such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

The following are examples of various groupings of amino acids: (i) Amino acids with nonpolar R groups: Alanine, Valine, Leucine, Isoleucine, Proline, Phenylalanine, Tryptophan, Methionine; (ii) Amino acids with uncharged polar R groups: Glycine, Serine, Threonine, Cysteine, Tyrosine, Asparagine, Glutamine; (iii) Amino acids with charged polar R groups (negatively charged at Ph 6.0): Aspartic acid, Glutamic acid; (iv) Basic amino acids (positively charged at pH 6.0): Lysine, Arginine, Histidine (at pH 6.0). Another grouping may be those amino acids with phenyl groups: Phenylalanine, Tryptophan, Tyrosine.

Another grouping may be according to molecular weight (i.e., size of R groups):

| | |
|---|---|
| Glycine | 75 |
| Alanine | 89 |
| Serine | 105 |
| Proline | 115 |
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

Two amino acid sequences are "substantially homologous" when at least about 70% of the amino acid residues, particularly at least about 80%, particularly at least about 90%, particularly at least about 95% are identical, or represent conservative substitutions. Amino acid sequences contemplated herein may be at least 70%, at least 75%, at least 80%, at least 85%, at least 90%, at least 95% identical to the sequences specifically provided herein.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

An "antibody" is any immunoglobulin, including antibodies and fragments thereof, that binds a specific epitope. The term encompasses polyclonal, monoclonal, and chimeric antibodies.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The phrase "pharmaceutically acceptable" refers to molecular entities and compositions that are physiologically tolerable and do not typically produce an allergic or similar untoward reaction, such as gastric upset, dizziness and the like, when administered to a human.

The term "treating" or "treatment" of any disease or disorder refers, in one embodiment, to ameliorating or alleviating the disease or disorder (i.e., arresting the disease or reducing the manifestation, extent or severity of at least one of the clinical symptoms thereof). In another embodiment "treating" or "treatment" refers to ameliorating or alleviating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In a further embodiment, "treating" or "treatment" relates to slowing the progression of the disease.

In one embodiment, the "treatment" in accordance with the methods provided herein is to improve, ameliorate, reduce the severity of, alleviate, decrease the duration of, maintain an improvement of, achieve a sustained improvement of, eliminate, or prevent an impairment associated with white matter disease or disorder, for example in a patient diagnosed with or suspected of having the disease, e.g., an impairment in neuromotor function in a patient. Such improvement, amelioration, reduction in the severity of, or alleviation in the impairment, e.g., in the impairment in neuromotor function, can be assessed by one or more (e.g., one, two, three, four or more than four) methods, such as one or more functional or assessable neurological or motor parameter, including an evaluable or scalable parameter, an assayable myelin or brain protein which is associated with white matter injury or with deficits of PVL, neuropathological changes in the cerebral white matter including as evident by ultrasound or MRI.

The phrase "therapeutically effective amount" is used herein to mean an amount sufficient to alter, and preferably reduce by at least about 30 percent, more preferably by at least 40 percent, more preferably by at least 50 percent, more preferably by at least 60 percent, more preferably by at least 70 percent, more preferably by at least 80 percent, most preferably by at least 90 percent, a clinically or developmentally significant change, particularly which relates to an alteration or impairment associated with white matter injury, or associated with diagnostic PVL, particularly in an infant, such as in an assessable neurological, neuromotor, or neurodevelopmental parameter or achievement, or other feature of pathology such as for example, neuropathological changes in the cerebral white matter, myelin quantity and quality, etc. By way of example, a therapeutically effective amount is an amount effective for treatment of neonatal hypoxia, particularly PVL.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20° C. below the predicted or determined $T_m$ with washes of higher stringency, if desired.

As used herein, "pg" means picogram, "ng" means nanogram, "ug" or "µg" mean microgram, "mg" means milligram, "ul" or "µl" mean microliter, "ml" means milliliter, "l" means liter.

DETAILED DESCRIPTION

The invention is directed to treatment of white matter disease or injury, including microscopic necrosis, particularly PVL, including due to infant hypoxia or neonatal hypoxia. The present invention is directed to methods to treat PVL, particularly to alleviate the impairments associated with PVL, particularly the myelin alterations and/or neuromotor deficits and/or neurodevelopmental deficits or alterations that result from or are correlated with PVL. In accordance with the invention methods, administration of compositions and active antibodies, particularly CNS binding antibodies, reverse, block or alleviate neural and motor alterations and deficits in white matter disease or injury, particularly PVL. In particular, neonates at risk of PVL or subjected to a PVL initiating hypoxic injury are suitable for intervention and treatment in accordance with the methods of the invention. In a particular embodiment, neonates at risk of white matter injury, particularly PVL, can be treated with the IgM antibodies as described herein.

Periventricular Leukomalacia (PVL) is characterized by the death of the white matter of the brain and can affect fetuses or newborns, with premature babies at the greatest risk of the disorder. PVL is an important recognized risk factor in neurological impairment of the premature infant. PVL is initially diagnosed by ultrasound or MRI and manifests ultimately in neural and motor defects in childhood. Persistent diffuse Periventricular hyperechogenecity for more than 7 days or periventricular cysts evident on ultrasound are diagnostics of PVL.

Premature infants and low birth weight infants are at high risk for encephalopathy of prematurity and neonatal hypoxia and can manifest white matter disease or injury, particularly PVL. The present invention is directed to methods and therapies, particularly therapeutic administration of antibodies to treat white matter disease or injury in infants, particularly PVL, including to alleviate impairments, including neuromotor or neurodevelopmental deficits associated with PVL. The methods of the present invention are particularly applicable in premature or low birth weight neonates; neonates who have suffered oxygen loss or deprivation during or immediately/shortly after birth; and infants undergoing complex congenital heart surgery, particularly when cardioplegia and cardiopulmonary bypass is required.

The invention is directed to treatment of white matter injury or disease, including alleviating microscopic necrosis particularly associated with PVL, including due to neonatal hypoxia. The present invention is directed to methods to treat PVL or alleviate the impairments associated with PVL, particularly myelin alterations and neuromotor deficits or alterations that result from PVL. In accordance with the invention, compositions and active antibodies are provided for use in the methods of the invention which reverse, block or alleviate neural and motor alterations and deficits in white matter disease or injury, particularly PVL. In particular, neonates at risk of PVL or subjected to a PVL initiating hypoxic injury are suitable for intervention and treatment in accordance with the methods of the invention.

The studies provided herein are the first known to evaluate and demonstrate that doses, including intraperitoneal (ip) doses, particularly a single dose, of antibody, particularly including HIgM12 and/or HIgM22 antibody(ies), HIgM42 or HIgM46 antiody(ies), rescue PVL-like or PVL-associated neuromotor deficits and phenotype in an animal. Studies demonstrating remarkable efficacy and therapeutically-relevant effects of these recombinant antibodies in animals and animal models of PVL and infant white matter disease are now provided. It is remarkable that administration, including particularly intraperitoneal (i.p.) treatment with a short lived molecule (15 hr half life estimated in mice), particularly monoclonal antibody, such as HIgM12 or HIgM22, has been found to rescue an animal from neuromotor defects and restore myelin quantity and quality in a neonatal hypoxia and PVL model. To date, no successful treatment for PVL, or for reversing or minimizing the effects of neonatal hypoxia, has been demonstrated or is available.

One challenge for neuroactive agents is specificity and targeting so that an agent's effects are directed against damaged/compromised neurons or cells in the CNS without significant activity against normal cells and thereby untoward, even potentially harmful side effects. The present invention now provides methods wherein specific and tolerable agent(s) capable of crossing the blood brain barrier and targeting areas of compromise or damage, are administered in instances of white matter injury, such as in PVL, in infants, particularly in hypoxia-induced PVL, particularly in infants, including neonates, which have been oxygen deprived or are at risk of PVL, to effect treatment, with minimal untoward effects on normal neurons.

The application provides evidence of the capability and therapeutically relevant activity of antibodies of the present invention, including HIgM12 and HIgM22, either alone or in combination, or HIgM42 or HIgM46, alone or in combination, in animal models of PVL and in animals demonstrating altered myelination and neuromotor deficits associated with PVL. In particular, studies provided herein demonstrate capability and activity in a model of neonatal hypoxia, particularly an exemplary PVL model. The model serves to mimic a white matter injury, particularly PVL condition, in a human between pre-term and term infancy, or gestational age of 28-36 or 32-36 weeks, or premature, or before 36 or 37 weeks. Compositions for use in the amelioration or treatment of any of neonatal hypoxia, encephalopathy of prematurity, or PVL in a pre-term or term infant, particularly in a low birth weight premature infant or a premature infant are provided. In an aspect, methods for the treatment of myelin alteration, maintenance of myelin quality, and treatment neuromotor deficits or alterations associated with white matter disease or injury in neonates or infants, particularly associated with PVL, are provided.

Monoclonal antibodies applicable in accordance with the methods of the invention, particularly recombinant antibodies, have been demonstrated to cross the blood brain barrier effectively and without any modification. The HIgM12, HIgM22, HIgM42 and HIgM46 antibodies improve nerve function and maintain axons in animal models of chronic axonal injury and demyelination. The antibodies have minimal toxicity in animals and do not exacerbate autoimmune conditions, as assessed in animal models.

Prior studies with HIgM12 have shown that the antibody binds to CNS neurons, supports neurite extension on antibody-coated substrate, and overrides the neurite extension inhibition of CNS myelin in in vitro studies (Warrington A et al (2004) J Neuropath Exp Neurol 63(5):461-473). The HIgM12 antibody and its sequence are described in WO 2006/004988 and WO 2012/054077. It has been demonstrated that certain human IgMs can promote remyelination (Warrington A E et al (2000) Proc Natl Acad Sci USA 97:6820-6825). For example, one such IgM is recombinant human monoclonal rHIgM22 (Mitsunaga Y B et al (2002) Faseb J 16:1325-1327). Antibody rHIgM22 binds to oligodendrocytes and myelin and promotes CNS remyelination in virus and toxin induced models of MS (Warrington A E et al (2000) Proc Natl Acad Sci USA 97:6820-6825; Bieber A J et al (2002) Glia 37:241-249). Spinal cord remyelination is induced after a single low dose of rHIgM22 (Warrington A E et al (2007) J Neurosci Res 85:967-976). After peripheral injection, rHIgM22 crosses the blood brain barrier (BBB) and accumulates within brain and spinal cord lesions of mice with demyelination. It has also been shown that rHIgM22 gets into the CSF in humans following systemic administration. Ferritin bead labeled rHIgM22 has been detected in lesions in vivo by MRI (Pirko I et al (2004) Faseb J 18:1577-1579). An additional human IgM antibody with remyelinating capability, sHIgM46, and its recombinant counterpart rHIgM46, has been also been described. The antibodies sHIgM22 and sHIgM46, and recombinant versions thereof, and methods for remyelination are described, e.g., in WO 2001/085797,US Pat. Nos. 7,473,423 and 7,807, 166.

Therapeutic Methods and PVL

The Examples and studies provided herein demonstrate treatment of white matter injury in infants (e.g., neonatal encephalopathy), particularly of PVL, particularly amelioration of neuromotor deficit(s) and myelin pathology associated with white matter injury including PVL, by administration of CNS reactive monoclonal antibodies. Thus, in a particular aspect, the present invention relates to methods and uses of CNS reactive antibodies in intervention relating to white matter disease or injury in a term or pre-term infant, in PVL, or in infants at high risk of PVL, or infants who have suffered hypoxia or reduced oxygen during delivery, or demonstrate PVL lesions on MRI or ultrasound.

PVL is an important factor in neurological impairment of infants, particularly premature infants. Risk factors for white matter disease or injury, including particularly PVL, include low Apgar score, relatively long periods of ventilation and oxygen inhalation, a more persistant presence of apneic spells, prolonged or repetitive variable decelerations (irregular abrupt decreases in fetal heart rate) during labor, respiratory distress syndrome type I (Ibari S et al (1995) Nihon Sanka Fujinka Gakkai Zasshi 47(11):1243-7). Also, infants born to mothers who suffered from preterm premature rupture of membranes, preeclampsia, and clinical chorioamnionitis are at greater risk for white matter disease or injury or PVL (Hatzidaki E et al (2009) Acta Obstet Hynecol Scand 88(1):110-5). Very low birth weight premature infants (VLBWI) are at risk for white matter disease or injury or PVL, particularly those with chorioamnionitis or neonatal sepsis (Silveira R et al (2008) J Pediatria 84(3):211-216).

Infants with any one or more of the above noted risk factors are suitable to benefit from and candidate subjects for the methods of the present invention. Thus, in an aspect of the invention, an infant, including a neonate, at risk of PVL, including having one or more risk factor, particularly including one or more of low Apgar score, relatively long periods of ventilation and oxygen inhalation, a more persistant presence of apneic spells, prolonged or repetitive variable decelerations (irregular abrupt decreases in fetal heart rate) during labor, respiratory distress syndrome type I, infants born to mothers who suffered from preterm premature rupture of membranes, preeclampsia or clinical chorioamnionitis, very low birth weight premature infants (VLBWI), particularly those with chorioamnionitis or neonatal sepsis, is a subject of the methods of the invention and a subject for administration of the compositions of the invention in accordance with the method(s). In accordance with the method, the antibody(ies) and/or compositions may be administered at birth, as quickly as possible upon birth, within a minute of birth, within minutes of birth, within a day after birth, or one or more times as quickly as possible after birth, or seconds, hours or days after birth.

In the event of diagnosed PVL, predicted PVL or risk of PVL, included documented hypoxia or loss of oxygen for a sustained period, fast and effective treatment is important, particularly to minimize effects that become evident after a delay or will manifest later in the infant's life. Faster treatment may result in less permanent or long-term damage and reduced myelin damage that cannot be corrected, less neuromotor damage. Ultrasounds and MRIs are utilized to assess or diagnose the type or extent of PVL or white matter injury in the infant.

Thus, in accordance with the method of the invention, a pregnant woman at risk of neonatal hypoxia or premature delivery, including a woman who has had a previous child with hypoxia or white matter injury or who is at risk of premature delivery, may be administered an antibody of use herein, particularly a CNS reactive antibody including one or more of IgM12, IgM22, IgM42 and/or IgM46, including active fragments thereof prior to, during, or at the outset of labor. The route of administration may be selected to provide rapid and effective delivery of the antibody directly or indirectly to the fetus, including delivery to the fetus in utero. Alternatively an infant delivered by such a pregnant woman may be administered an antibody of use in the invention at the time of birth or immediately or shortly thereafter, including at birth, seconds after birth, within minutes of birth, in less than an hour after birth, etc and monitored thereafter for oxygenation, hypoxia, or effects of hypoxia.

The antibodies, fragments thereof and recombinant antibodies comprising the variable region sequences as provided herein may be used in methods of treatment or diagnosis of the human or animal body, such as a method of treating white matter disease or injury, particularly PVL, and of alleviating, blocking or reducing myelin damage, OL damage, and/or neuromotor deficits, including those associated with neonatal hypoxia, which comprises administering to said mammal, particularly an infant, including a neonate, particularly an infant that is not born full term or full gestational age, an effective amount of the antibodies, fragments thereof and recombinant antibodies of use in the invention, particularly one or more or both of antibody HIgM12 and/or HIgM22, or one or more of HIgM12, HIgM22, HIgM42 and/or HIgM46, including recombinant antibodies or fragments thereof comprising the CDR domain region sequences of HIgM12, HIgM22, HIgM42 and/or HIgM46. In an aspect of the methods, the agents of the invention, particularly recombinant antibodies or fragments thereof may be used in instances of established, suspected or possible white matter damage or injury, including PVL, in an infant or pre-term baby, including as agents in methods for prevention, treatment or amelioration of nerve injury, damage or compromise and complications that can, may or do result from PVL and/or infant white matter injury like PVL.

The present invention provides methods of treating white matter disease or injury, particularly PVL in an infant, including a neonate, particularly a pre-term infant born before gestational week 32 or 36 or 37, comprising administering a CNS binding antibody, particularly recombinant antibody, particularly one or more antibody of IgM12, IgM22, IgM42 and/or IgM46, including one or more of: (a) an antibody or fragment thereof comprising heavy chain CDR sequences CDR1 GGSVSLYY (SEQ ID NO: 1), CDR2 GYIYSSGST (SEQ ID NO: 2) and CDR3 ARSA-SIRGWFD (SEQ ID NO: 3), and light chain CDR sequences CDR1 QSISSY (SEQ IDNO: 4), CDR2 AAS (SEQ ID NO: 5) and CDR3 QQSYHTPW (SEQ ID NO: 6); (b) an antibody or fragment thereof comprising heavy chain CDR sequences CDR1 SSGMH (SEQ ID NO: 11), CDR2 V(I)ISYDGSRKYYADSVKG (SEQ ID NO:12) and CDR3 GVTGSPTLDY (SEQ ID NO:13), and light chain CDR sequences CDR1 SGSSSNIGNNFVS (SEQ ID NO: 14), CDR2 DITKRPS (SEQ ID NO:15) and CDR3 G(E)TWDSSLSAVV (SEQ ID NO: 16), or an antibody or fragment thereof comprising heavy chain CDR sequences CDR1 SSGMH (SEQ ID NO: 11), CDR2 VAIISYDGSRKYYADSVKG (SEQ ID NO:55) and CDR3 GVTGSPTLDY (SEQ ID NO:13), and light chain CDR sequences CDR1 SGSSSNIGNNFVS (SEQ ID NO: 14), CDR2 DITKRPS (SEQ ID NO:15) and CDR3 CETWDSSLSAVV (SEQ ID NO: 56); (c) an antibody or fragment comprising the variable heavy chain amino acid CDR sequences CDR1 GFTFSTYA (SEQ ID NO:21), CDR2 INVGGVTT (SEQ ID NO:22) and CDR3 VRRSGPDRNSSPADF (SEQ ID NO:23), and light chain CDR sequences CDR1 QGIG (SEQ ID NO: 24), CDR2 TTS (SEQ ID NO:25) and CDR3 QKYNSAPRT (SEQ ID NO:26); or (d) an antibody or fragment comprising the variable heavy chain amino acid CDR sequences CDR1 SGFTFSSYW (SEQ ID NO: 31), CDR2 IKKDGSEK (SEQ ID NO:32) and CDR3 ARPNCGGDCYLPWYFD (SEQ ID NO:33), and light chain CDR sequences CDR1 QSVLYSSNNKNY (SEQ ID NO: 34), CDR2 YWAS (SEQ ID NO:35) and CDR3 QQYYNTPQA (SEQ ID NO: 36).

The present invention provides methods of treating PVL or reducing the risk of PVL or the risk of neuromotor deficits in an infant diagnosed with PVL comprising administering a recombinant antibody or fully human antibody or fragment thereof selected from IgM12 and IgM22, or a combination of IgM12 and IgM22. The invention also provides methods of treating PVL or reducing the risk of PVL or the risk of neuromotor deficits in an infant diagnosed with PVL comprising administering a recombinant antibody or fully human antibody or fragment thereof selected from IgM42 and IgM46, or a combination of IgM42 and IgM46. Methods of the invention may comprise administration of more than one antibody or fragment, including combinations of one or more of antibodies IgM12, IgM22, IgM42 and IgM46, including combinations of antibody IgM12 and IgM22, combinations of IgM42 and IgM46, combinations of IgM12 and IgM46, combinations of IgM42 and IgM22, combinations of IgM12 and IgM42, etc. In a further such method, one or more of antibody IgM12 and/or of antibody IgM22 may be combined with another CNS active antibody, particularly including one or more of antibodies rHIgM42 and/or rHIgM46.

Combinations of antibodies may be administered collectively or in series, and at various times and various amounts or concentrations. Thus, antibody 12 and/or 22 may be administered in combination with antibody 42 and/or 46, by combined administration or in series, separated by a short length of time or longer length of time, including by hours days or weeks. Antibody 12 and/or 22 may particularly be administered in combination with antibody 42 and/or 46 (sHIgM42, rHIgM42, sHIgM46 or rHIgM46), by combined administration or in series for the treatment of PVL or alleviating the risk of PVL or the risk of neuromotor deficits in an infant diagnosed with PVL. Methods of the invention may include administration of the antibodies of the invention alone or in combination with, in series with, or subsequent to administration of other or alternative neuroactive agents, anti-inflammatory agents, neuromodulatory agents, steroids, neuroprotective agents, immunomodulatory agents, nitric oxide mediators, free radical scavengers, etc.

Administered with may include at about the same time, shortly after, minutes after, up to an hour after, hours after, a day after. Administration of the antibody(ies), either alone particularly as antibodies IgM12 or IgM22 or IgM42 or IgM46, or in combination, or with other agents, may be at birth, as soon after birth as possible, within seconds after birth, within a minute after birth, within minutes after birth, within 5 minutes after birth, within 10 minutes after birth, within 20 minutes after birth, within an hour after bith, or several hours, less than a day after, 3 hours, 4 hours, 5 hours, 6 hours, up to 9 or 12 hours after birth, one day, two days, three days, 7 days, a week, 10 days, 12 days after birth. Antibody(ies) may be administered in a single dose or multiple doses. By way of example and not limitation, antibody(ies) may be administered within minutes, within 10 minutes, within 20 minutes, within 30 minutes, within an hour, within 2 hours, 3 hours, after 3 hours, up to 4 hours, up to 5 hours, up to 6 hours, up to 8 hours, up to 12 hours, up to 24 hours, up to a day, up to 2 days, up to 3 days, up to several days, up to a week, or longer after birth or after white matter injury, particularly including PVL, diagnosis or following a documented or suspected PVL initiating or causing event, such as short term or prolonged loss of oxygen during or after birth. Dosing may be modulated based on the response or function of the patient, and PVL lesions may be monitored by MRI or ultrasound. For example, the patient may be evaluated, for example using ultrasound, MRI or neuromotor response before or after, before and after, or following initial administration of antibody, and antibody administration may be modified or continued or altered based on such a diagnostic or other neurological or motor evaluation of the patient. In a particular aspect of the invention and the method, the antibody (ies) are effective in improving myelination, OL markers, or other neurological or functional scales, particularly when compared to no antibody administration, administration of other agent alone, or versus an alternative agent, including an alternative antibody or neuroprotective agent.

Thus, as demonstrated herein in animal models of PVL, animals administered the antibody(ies) of the invention demonstrate improved myelination, myelin protein markers, OL markers, and neuromotor and functional activity. In an aspect of the invention and its methods, the antibody(ies) of the invention are effective to prevent or reverse infant brain white matter injury-related, particularly PVL-related, neurologic or motor deficits. Thus, the methods of the invention can ameliorate one or more neurological symptom or deficit in instances of PVL or diagnosed PVL lesions or suspected PVL, particularly in an infant, including a neonate. The methods of the invention are effective in mitigating the neurological effects or damage, particularly in the CNS, in the event or instance of PVL in an infant or baby or child.

The methods may ameliorate white matter injury or encephalopathy in neonatal hypoxia, including microscopic necrosis, which may or may not be evident by MRI or mass spectrometry (MS) screening or assessment. Antibody efficacy and capability may be evaluated using standard neurological imaging and assessment. Brain volumetric analysis by MRI including ventricle size may be utilized in efficacy studies. Ventriculomagaly is a typical neuropathological outcome in preterm infants diagnosed with PVL. Thus, any effects of antibodies to prevent the pathologically increased ventricle size would demonstrate efficacy. The brain area around the ventricles is particularly sensitive to hypoxic stress showing increased cell death and delayed oligodendrocyte maturation. Antibody-mediated effects on prevention of cell death or stimulation of oligodendrocyte maturation would be highly beneficial and can be evaluated via histological findings.

Efficacy can be assessed in behavioral tests including neuro-motor outcome and cognitive tests. MRI and MS are useful tools for objective quantifiable data regarding brain development. Standard neurological scales and examinations may be used, and can demonstrate sustained effects and efficacy. Long term loss of cognitive function can be evaluated in children suffering from or having suffered neonatal hypoxia, encephalopathy of PVL as they mature. In toddlers to young children (18 months to 3 years), Bailey Scales of Infant Development-III are applicable. The Wechsler Intelligence Scale for Children is applicable for children and adolescents ages 6-16.

In an aspect of the invention, methods are provided for improvement or stabilization of neurological function or of motor function in instances, particularly following, or upon or in instances of PVL or suspected PVL or presence of PVL-associated risk factors as detailed herein, particularly in an infant, particularly a pre-term infant shortly after, at or within seconds, minutes, hours or days of birth. In a particular aspect, the antibodies or fragments thereof are utilized or administered in early or upon diagnosis of PVL, at birth or shortly after birth in very low birth weight infants, including infants weighing less than 1500 g or less than 1200 g, or premature or preterm infants or infants born before gestational age of 32 weeks or 36 weeks or 37 weeks. In accordance with the method, the antibodies or fragments may be administered in a single dose, alone or in combination or in series, or repeated over the first hour, hours, day, days or week(s), or months, or year after birth.

In the method, antibodies may be administered to a patient in need of treatment via any suitable route, including by injection intraperitoneally, into the bloodstream or CSF, or directly into the site of injury or compromise. Antibodies may be administered by injection or intravenously (i.v.). A particular advantage of the exemplary antibodies of the present invention is that they cross the BBB and can therefore target the CNS even on i.p. administration. The precise dose will depend upon a number of factors, including whether the antibody is for diagnosis or for treatment, the size or extent and location of the injury, the precise nature of the antibody (whether whole antibody, fragment, diabody, etc), and the nature of any detectable or functional label attached to the antibody. Where a radionuclide is used for therapy, a suitable maximum single dose may be about 45 mCi/$m^2$, to a maximum of about 250 mCi/$m^2$. Preferable dosage is in the range of 15 to 40 mCi, with a further preferred dosage range of 20 to 30 mCi, or 10 to 30 mCi. Such therapy may require bone marrow or stem cell replacement. Clinically-approved naked antibodies are generally administered in sub-mg or in mg quantities, with adult doses of 20 to 2000 mg protein per dose, 20 to 1500 mg protein per dose, or 20 to 1000 mg protein per dose, or 20 to 500 mg protein per dose, or 20 to 100 mg protein per dose. Clinically-approved injectable monoclonal antibodies are administered in mg amounts, 3-5 mg/kg, 5-10 mg/kg per dose, 300-400 mg/dose, 300-500 mg/dose (Newsome B W and Ernstoff M S (2008) Br J Clin Pharmacol 66(1):6-19; herceptin.net, tysabri.net, avastin.net, remicade.com). Antibodies administered to infants or neonates may be administered in mg or sub mg doses, such as less than 0.5 mg, less than 1 mg, 1-3 mg, 3 mg, 3-5 mg, 5-7 mg, 5-10 mg, 10 mg, 10-12 mg, 10-15 mg, 15 mg, 15-20 mg, 20 mg, 20-25 mg, 25 mg, 25-30 mg, 30 mg, 3-30 mg doses for example. Lowest effective doses are preferred in these small infants and neonates.

It is notable that the remyelinating antibody IgM22 has been shown to be effective in comparatively significantly lower doses, in the µg range, and is capable of crossing the BBB to be active in the CNS with even a single dose of antibody (WO 2004/110355; Warrington A E et al (2007) J Neurosci Res 85(5):967-976). Recombinant IgM12 antibody and IgM22 antibody are each shown herein to have therapeutically relevant activity in animal models upon a single i.p. dose in the µg range (30 µg to a mouse showed efficacy). Thus dosing of the antibodies in accordance with the methods of the present invention, may be either single dose, or multiple and/or periodic doses, in the range of gigs per dose or µg/kg doses, or in low mg per dose (100 µg-1 mg, less than 1 mg, 1 mg-5 mg, 1 mg-10 mg, 5 mg-15 mg, 10 mg-20 mg per dose), and may be applicable and effective. A dose for a single treatment of an adult patient, may be proportionally adjusted for children and infants, and also adjusted for other antibody formats, in proportion for example to the weight of the patient. Treatments may be repeated at hourly, daily, twice-weekly, weekly or monthly intervals, at the discretion of the physician. Dosing may be done in multiple doses spaced over hours or days, so as to limit or minimize the protein dose to the infant or neonate in each dose, while ensuring effectiveness of the individual or combined doses. One advantage of the exemplary antibodies for use in the method is that they cross the BBB and target sites of damage or injury, thus facilitating the methods wherein lower and potentially fewer doses are required or utilized to achieve suitable effects.

A subject or patient administered a CNS reactive antibody of use in accordance with the methods herein is preferably a human, but can be any animal, and may particularly be a mammal. Thus, as can be readily appreciated by one of ordinary skill in the art, the methods of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., i.e., for veterinary medical use. The preferred subject or patient is a human.

Antibodies and Compositions for Use in the Methods

The invention provides human antibodies, including monoclonal antibodies and particularly recombinant antibodies, for use in the methods to demonstrate activity in treating PVL, particularly PVL in infants, including neonates. The exemplary method antibodies, including fragments thereof, demonstrate activity in the alleviation or amelioration of myelin alteration, maintenance of myelin quality, and treatment or reduction of neuromotor deficits or alterations associated with or causally related to PVL in the central nervous system. The antibodies and compositions applicable in the method of the invention are applicable in reducing the development of neuromotor deficits in a young child or young animal when administered to an infant, particularly a premature infant diagnosed with PVL or demonstrating persistent diffuse periventricular hyperechogenecity for more than 7 days or periventricular cysts on ultrasound, or such other relevant and accepted diagnostic of PVL.

The present invention provides exemplary antibody(ies) or fragment(s) thereof of use and applicable in the methods of the invention, particularly recombinant HIgM12 or HIgM22, particularly recombinant HIgM42 or HIgM46, and combinations thereof. Recombinant antibody IgM12 of use in the present invention comprises the variable heavy chain (SEQ ID NO: 7) and light chain sequence (SEQ ID NO: 8) as set out in FIG. 10, including an antibody having 90% amino acid sequence identity and the capabilities of IgM12. Recombinant antibody IgM22 of use in the present invention comprises the variable heavy chain (SEQ ID NO: 17) and light chain sequence (SEQ ID NO: 18) as set out in FIG. 11, including an antibody having 90% amino acid sequence identity and the capabilities of IgM22. Recombinant antibody IgM42 of use in the present invention comprises the variable heavy chain (SEQ ID NO: 27) and light chain sequence (SEQ ID NO: 28) as set out in FIG. 12, including an antibody having 90% amino acid sequence identity and the capabilities of IgM42. Recombinant antibody IgM46 of use in the present invention comprises the variable heavy chain (SEQ ID NO: 37) and light chain sequence (SEQ ID NO: 38) as set out in FIG. 13, including an antibody having 90% amino acid sequence identity and the capabilities of IgM46.

Panels of recombinant antibodies or fragments thereof, including Fab fragments or phage display libraries, which are capable of recognizing neurons, particularly human neurons, can be screened for various properties; i.e., affinity, isotype, epitope, stability, etc. Of particular interest are antibodies that mimic the activity of exemplary antibodies IgM12 and/or IgM22 and/or IgM42 and/or IgM46, and have the ability to bind neurons and to protect neurons from cell death or injury, and particularly that are capable of treating white matter disease or injury, particularly PVL, and alleviating the effects or deficits thereof and associated therewith, including in a PVL animal model as described herein. Such antibodies can be identified and/or screened in specific binding and activity assays. Such antibodies include antibodies capable of competing with binding of antibody IgM22, including competing with binding of IgM22 as deposited with American Type Culture Collection (ATCC) on Sep. 28, 2007 as PTA-8671. Antibodies include antibodies capable of competing with binding of antibody IgM12, including competing with binding of IgM12 as deposited with ATCC on Jan. 17, 2008 as PTA-8932. Recombinant antibodies comprising the antigen binding region or the heavy and/or light chain CDR regions of the present antibodies IgM12 and/or IgM22 or of IgM42 and/or IgM46, may be generated and screened for activity. Recombinant antibodies comprising the antigen binding region or the heavy and/or light chain CDR1, CDR2, and CDR3 regions of IgM22 antibody as deposited with ATCC on Sep. 28, 2007 as PTA-8671, or the heavy and/or light chain CDR1, CDR2, and CDR3 regions of IgM12 antibody as deposited with ATCC on Jan. 17, 2008 as PTA-8932 are suitable and contemplated in the methods of the invention.

Alternative antibodies of use and applicable in the methods of the invention may be identified by determining competition binding with antibodies IgM12, IgM22, IgM42 and/or IgM46. Further, alternative antibodies or variant antibodies may be assessed for binding to ligands recognized or bound by any one or more of antibodies IgM12, IgM22, IgM42 and/or IgM46. Such binding may include recognition or binding of oligodendrocytes, glycolipid binding, binding to gangliosides, particularly GT1b and/or GD1a, and/or binding to neural cell adhesion molecule (NCAM), particularly polysialylated NCAM (PSA-NCAM). In a particular aspects alternative or variant antibodies are isolated, screened or evaluated for or by determining binding to NCAM, particularly PSA-NCAM, and/or competition with IgM12 and/or IgM42 binding. In particular aspects alternative or variant antibodies are isolated, screened or evaluated for or by determining binding to oligodendrocytes, and/or competition with IgM22 and/or IgM46 binding.

In general, the CDR regions, comprising amino acid sequences substantially as set out as the CDR regions of FIG. 10, 11, 12 or 13 will be carried in a structure which allows for binding of the CDR regions to the surface or at the surface of neurons, and particularly to mammalian neurons, particularly human, monkey, baboon, rat, and/or mouse neurons. By "substantially as set out" it is meant that that variable region sequences, and/or particularly the CDR sequences, of the invention will be either identical or highly homologous to the specified regions of FIG. 10, 11, 12 or 13 and as detailed herein. By "highly homologous" it is contemplated that only a few substitutions, preferably from 1 to 8, preferably from 1 to 5, preferably from 1 to 4, or from 1 to 3, or 1 or 2 substitutions may be made in the variable region sequence and/or in the CDR sequences. The term "substantially as set out" includes particularly conservative amino acid substitutions which do not materially or significantly affect the specificity and/or activity of the instant antibodies.

Substitutions may be made in the variable region sequence outside of the CDRs so as to retain the CDR sequences. Thus, changes in the variable region sequence or alternative non-homologous or veneered variable region sequences may be introduced or utilized, such that the CDR sequences are maintained and the remainder of the variable region sequence may be substituted. Alternatively, substitutions may be made particularly in the CDRs. For example, antibody 12, IgM12, comprises heavy chain CDR sequences CDR1 GGSVSLYY (SEQ ID NO:1), CDR2 GYIYSSGST (SEQ ID NO:2) and CDR3 ARSASIRGWFD (SEQ ID NO:3), and light chain CDR sequences CDR1 QSISSY (SEQ IDNO: 4), CDR2 AAS (SEQ ID NO:5) and CDR3 QQSYHTPW (SEQ ID NO:6), as set out in FIG. 10. Antibody 22 comprises heavy chain CDR sequences CDR1 SSGMH (SEQ ID NO: 11), CDR2 V(I)ISYDGSRKYY-ADSVKG (SEQ ID NO:12) and CDR3 GVTGSPTLDY (SEQ ID NO:13), and light chain CDR sequences CDR1 SGSSSNIGNNFVS (SEQ ID NO: 14), CDR2 DITKRPS (SEQ ID NO:15) and CDR3 G(E)TWDSSLSAVV (SEQ ID NO: 16), as set out in FIG. 11. In another embodiment, antibody 22 comprises heavy chain CDR sequences CDR1 SSGMH (SEQ ID NO: 11), CDR2 VAIISYDGSRKYY-ADSVKG (SEQ ID NO:55) and CDR3 GVTGSPTLDY (SEQ ID NO:13), and light chain CDR sequences CDR1 SGSSSNIGNNFVS (SEQ ID NO: 14), CDR2 DITKRPS (SEQ ID NO:15) and CDR3 CETWDSSLSAVV (SEQ ID NO: 56). Antibodies of the invention having substitutions as above described and contemplated are selected to maintain the activities and specificity commensurate with the exemplary antibodies, including antibodies IgM12, IgM22, IgM42 and/or IgM46 and having the characteristics as set out herein and capability in the methods hereof.

The structure for carrying the CDRs of the invention will generally be of an antibody heavy or light chain sequence or substantial portion thereof in which the CDR regions are located at locations corresponding to the CDR region of naturally occurring VH and VL antibody variable domains encoded by rearranged immunoglobulin genes. The structures and locations of immunoglobulin variable domains and/or CDRs may be determined by reference to numbering schemes known in the art (e.g., Kabat Numbering, see Kabat, E. A. et al, Sequences of Proteins of Immunological Interest. 4th Edition. US Department of Health and Human Services. 1987, and updates thereof, now available on the Internet (immuno.bme.nwu.edu), Clothia Numbering). The variable domains may be derived from any germline or rearranged human variable domain, or may be a synthetic variable domain based on consensus sequences of known human variable domains. The CDR-derived sequences of the invention, as defined in the preceding paragraph, may be introduced into a repertoire of variable domains lacking CDR regions, using recombinant DNA technology.

For example, Marks et al (Bio/Technology, 1992, 10:779-783) describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR/CDRs. Marks et al further describe how this repertoire may be combined with a CDR of a particular antibody. The repertoire may then be displayed in a suitable host system such as the phage display system of WO92/01047 so that suitable specific binding members may be selected. A repertoire may consist of from anything from $10^4$ individual members upwards, for example from $10^6$ to $10^8$ or $10^{10}$ members. Analogous shuffling or combinatorial techniques are also disclosed by Stemmer (Nature, 1994, 370:389-391), who describes the technique in relation to a β-lactamase gene but observes that the approach may be used for the generation of antibodies.

A further alternative is to generate novel VH or VL regions carrying the CDR-derived sequences of the invention using random mutagenesis of, for example, the Ab VH or VL genes to generate mutations within the entire variable domain. Such a technique is described by Gram et al (1992, Proc. Natl. Acad. Sci., USA, 89:3576-3580), who used error-prone PCR. Another method which may be used is to direct mutagenesis to CDR regions of VH or VL genes. Such techniques are disclosed by Barbas et al, (1994, Proc. Natl. Acad. Sci., USA, 91:3809-3813) and Schier et al (1996, J. Mol. Biol. 263:551-567). All the above described techniques are known as such in the art. The skilled person will be able to use such techniques to provide specific binding members of the invention using routine methodology in the art.

A substantial portion of an immunoglobulin variable domain will comprise at least the three CDR regions, together with their intervening framework regions. Preferably, the portion will also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of specific binding members of the present invention made by recombinant DNA techniques may result in the introduction of N- or C-terminal residues encoded by linkers introduced to facilitate cloning or other manipulation steps. Other manipulation steps include the introduction of linkers to join variable domains of the invention to further protein sequences including immunoglobulin heavy chains, other variable domains (for example in the production of diabodies) or protein labels as provided herein and/or known to those of skill in the art.

Although in a preferred aspect of the invention recombinant antibodies comprising a pair of binding domains based on sequences substantially set out in FIGS. 10, 11, 12 and/or 13 are preferred, single binding domains based on either of these sequences form further aspects of the invention. In the case of the binding domains based on the sequence substantially set out in FIG. 10 and/or 11 and/or 12 and/or 13, such binding domains may be used as targeting agents for CNS cells such as neurons or oligodendrocytes, particularly sites of myelin or nerve damage or injury, since it is known that immunoglobulin VH domains are capable of binding target antigens in a specific manner.

Antibodies of use in the methods of the present invention may further comprise antibody constant regions or parts thereof. For example, recombinant antibodies based on the VH and VL sequences of FIGS. 10, 11, 12 and/or 13 may be attached at their C-terminal end to antibody heavy and/or light chain constant domains, particularly human constant domains. Examples of human light chains, include, but are not limited to, kappa or lambda. Examples of human heavy chains include, but are not limited to, mu, epsilon, gamma, alpha and delta. In one embodiment the antibody comprises mu heavy chains and lambda light chains. The recombinant antibodies based on the sequences of FIG. 10, 11, 12 or 13 may be attached at their C-terminal end to all or part of an immunoglobulin heavy chain derived from any antibody isotype, e.g. IgG, IgA, IgE, IgD and IgM and any of the isotype sub-classes, particularly IgG1, IgG2b, and IgG4, and then tested to affirm or determine comparable and/or suitable activity and capability. IgM is preferred. In a preferred aspect, recombinant antibodies of use in the invention are selected from IgM12, IgM22, IgM42 and IgM46. In an aspect, IgM12 antibody comprises heavy chain CDR sequences SEQ ID NO: 1-3 and light chain CDR sequences SEQ ID NO: 4-6, IgM22 antibody comprises heavy chain CDR sequences SEQ ID NO: 11-13 and light chain CDR sequences SEQ ID NO: 14-16 or heavy chain CDR sequences SEQ ID NO: 11, 55 and 13 and light chain CDR sequences SEQ ID NO: 14, 15 and 56, IgM42 antibody comprises heavy chain CDR sequences SEQ ID NO: 21-23 and light chain CDR sequences SEQ ID NO: 24-26, IgM46 antibody comprises heavy chain CDR sequences SEQ ID NO: 31-33 and light chain CDR sequences SEQ ID NO: 34-36. In some embodiments the antibodies comprise a human J chain. In some embodiments the J chain of the recombinant antibody is a human J chain (e.g., SEQ ID NO: 54). In some embodiments, the J chain of the recombinant antibody is a non-human J chain, for example a mouse J chain (e.g., SEQ ID NO: 53). The recombinant antibody is preferably an IgM antibody.

The antibodies, or any fragments thereof, may be conjugated or recombinantly fused to any cellular toxin, bacterial or other, e.g. pseudomonas exotoxin, ricin, or diphtheria toxin. The part of the toxin used can be the whole toxin, or any particular domain of the toxin. Such antibody-toxin molecules have successfully been used for targeting and therapy of different kinds of cancers, see e.g. Pastan, Biochem Biophys Acta. 1997 Oct. 24; 1333(2):C1-6; Kreitman et al., N Engl J Med. 2001 Jul. 26; 345(4):241-7; Schnell et al., Leukemia. 2000 January; 14(1):129-35; Ghetie et al., Mol Biotechnol. 2001 July; 18(3):251-68. Bi- and tri-specific multimers can be formed by association of different scFv molecules and have been designed as cross-linking reagents for T-cell recruitment into tumors (immunotherapy), viral retargeting (gene therapy) and as red blood cell agglutination reagents (immunodiagnostics), see e.g. Todorovska et al., J Immunol Methods. 2001 Feb. 1; 248 (1-2):47-66; Tomlinson et al., Methods Enzymol. 2000; 326:461-79; McCall et al., J Immunol. 2001 May 15; 166(10):6112-7.

Antibodies of use in the methods of the invention may be labeled with a detectable or functional label. Detectable labels include, but are not limited to, radiolabels such as the isotopes $^3$H, $^{14}$C, $^{32}$P, $^{35}$S, $^{36}$Cl, $^{51}$Cr, $^{57}$Co, $^{58}$Co, $^{59}$Fc, $^{90}$Y, $^{121}$I, $^{124}$I, $^{125}$I, $^{131}$I, $^{111}$In, $^{117}$Lu, $^{211}$At, $^{198}$Au, $^{67}$Cu, $^{225}$Ac, $^{213}$Bi, $^{99}$TC and $^{186}$Re, which may be attached to antibodies of the invention using conventional chemistry known in the art of antibody imaging. Labels also include fluorescent labels (for example fluorescein, rhodamine, Texas Red) and labels used conventionally in the art for MRI-CT imaging. They also include enzyme labels such as horseradish peroxidase, β-glucoronidase, β-galactosidase, urease. Labels further include chemical moieties such as biotin which may be detected via binding to a specific cognate detectable moiety, e.g. labeled avidin. Functional labels include substances which are designed to be targeted to the site of compromise, damage or injury to provide protection of or cause destruction of neural tissue. Such functional labels include cytotoxic drugs such as 5-fluorouracil or ricin and enzymes such as bacterial carboxypeptidase or nitroreductase, which are capable of converting prodrugs into active drugs at the site Immunoconjugates or antibody fusion proteins of the present invention are contemplated, wherein the antibodies and fragments thereof are conjugated or attached to other molecules or agents further include, but are not limited to binding members conjugated to a chemical ablation agent, toxin, immunomodulator, cytokine, cytotoxic agent, chemotherapeutic agent or drug. When radioactive labels are used, known currently available counting procedures may be utilized to identify and quantitate the specific binding members. In the instance where the label is an enzyme, detection may be accomplished by any of the presently utilized colorimetric, spectrophotometric, fluorospectrophotometric, amperometric or gasometric techniques known in the art.

The hypoxia in vivo animal model of PVL described herein, rearing mice in hypoxic conditions for a defined postnatal period, particularly from P3 to P7, which results in myelin alterations and neuromotor deficits, may be utilized by the skilled artisan to further or additionally screen, assess, and/or verify antibodies or fragments thereof suitable in the methods of the present invention, variants thereof, or of combinations thereof, or of combinations with other CNS reactive antibodies. Alternative PVL or white matter injury animal models, particularly those mimicking human gestational weeks 32-36 or pre-term and term infancy, may also or alternatively be utilized to evaluate, screen and assess antibodies, fragments, variants, or combinations for use in the methods of the invention. Alternative models are known in the art and available. Several such models may provide differential manifestations of PVL or of brain and body weight alterations or of altered animal survival, however, they may still provide useful or differential information and data regarding methods and compositions of the invention. PVL models include the Rice-Vanucci model (Rice J R et al (1981) Ann Neurol 9(2):131-141); Vanucci and Vanucci (2005) Dev Neurosci 27:81-86), chronic hypoxia models (Back et al (2006) Ann Neurol 60:696-705; Fagel et al (2006) Exp Neurol 199:77-91; Chahboune et al (2009) Cereb Cortex 19:2891-2901; Scafidi et al (2009) Int J Dev Neurosci 27:863-871), in utero ischemia models (Cai et al (1998) Brain Res Dev Brain Res 109:265-269; Drobyshevsky et al (2005) J Neurosci 25:5988-5997; McClure et al (2008) J Cereb Blood Flow Metab 5:995-1008), and others (reviewed by Silbereis et al (2010) Dis Models & Mech 3:678-688).

Antibodies or fragments of use in the methods of the present invention will usually be administered in the form of a pharmaceutical composition, which may comprise at least one component in addition to the antibody(ies) or fragments of the invention. Thus pharmaceutical compositions according to the present invention, and for use in accordance with the present invention, may comprise, in addition to active ingredient, a pharmaceutically acceptable excipient, carrier, buffer, stabilizer or other materials well known to those skilled in the art. Such materials should be non-toxic and should not interfere with the efficacy of the active ingredient. The precise nature of the carrier or other material will depend on the route of administration, which may be oral, or by injection, e.g. intravenous, or by deposition at a tumor site.

Pharmaceutical compositions for oral administration may be in tablet, capsule, powder or liquid form. In one embodiment the pharmaceutical compositions are in a liquid form for injection, including subcutaneous injection, intravenous and or administration via a shunt. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. For intravenous, injection, or injection at the site of affliction, the active ingredient may be in the form of a parenterally acceptable aqueous solution which is pyrogen-free and has suitable pH, isotonicity and stability. In one embodiment the pharmaceutical compositions are in a liquid form for injection, including subcutaneous injection, intravenous and or administration via a shunt. By way of example, and not limitation, administration of antibodies, including pharmaceutical compositions, of the invention is by injection, particularly intravenous injection. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required.

A composition may be administered alone or in combination with other treatments, therapeutics or agents, either simultaneously or sequentially dependent upon the condition to be treated. Compositions comprising combinations of one or more recombinant antibody or fragment thereof as described herein are contemplated. In addition, the present invention contemplates and includes compositions comprising the antibody or fragment thereof, herein described and other agents or therapeutics such as neuroactive agents or therapeutics, anti-inflammatory agents, neurotransmitter release modulating agents, neuroreceptor ligands or agonists or antagonists, calcium channel agents, immune modulators, or other CNS reactive antibodies. In accordance with the methods herein, one or more CNS reactive antibody may be utilized and/or administered in combination with, in conjunction with, or as additional therapy with, administered before or after, an anti-inflammatory agent, such as a steroid or glucocorticoid. The antibody(ies) may be administered in a method of therapy combined or associated with therapeutic hypothermia. Compositions comprising combinations of one or more recombinant antibody or fragment thereof as described herein are contemplated. Other treatments or therapeutics may include the administration of suitable doses of pain relief drugs such as non-steroidal anti-inflammatory drugs (e.g. aspirin, paracetamol, ibuprofen or ketoprofen) or opiates such as morphine, or anti-emetics. In addition, the composition may be administered with immune modulators, such as interleukins, tumor necrosis factor (TNF) or other growth factors, colony stimulating factors, cytokines or hormones such as dexamethasone which modulate the immune response or inflammatory response, and/or reduce immune reactions, inflammatory responses or inflammatory cells. The present invention further contemplates therapeutic compositions useful in practicing the therapeutic methods of this invention. A subject therapeutic composition includes, in admixture, a pharmaceutically acceptable excipient (carrier) and one or more of an antibody, polypeptide analog thereof, or active fragment thereof, as described herein as an active ingredient. In a preferred embodiment, the composition comprises an antibody or fragment of IgM12, IgM42, IgM22 and/or IgM46, including antibodies comprising the heavy chain CDRs or heavy and light chain CDRs thereof.

The preparation of therapeutic or pharmaceutical compositions which contain antibodies, polypeptides, or active fragments as active ingredients is well understood in the art. Typically, such compositions are prepared as injectables, either as liquid solutions or suspensions. However, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient. An antibody or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic antibody- or active fragment-containing compositions are conventionally administered intraperitoneally or intravenously, as by injection of a unit dose, for example. The compositions may be administered intranasally, by inhalation, or via the airway or orally. In an aspect the antibodies are administered by any effective means to provide dosing to a neonate or infant, including by intravenous (IV), intraperitoneal (IP), intranasal (IN) or oral or mucosal means, or intrathecally or by direct CNS administration (e.g., via a shunt). The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on for example the subject to be treated, capacity of the subject's system to utilize the active ingredient, and degree of neuron binding capacity desired or extent of white matter disease or injury, the degree or length of hypoxia, the gestational age of the neonate or infant. Precise amounts of active ingredient required to be administered depend on the judgment of the practitioner and are peculiar to each individual. Suitable regimes for initial administration and follow on administration are also variable, and may include an initial administration followed by repeated doses at one or more hour, day, week or month intervals by a subsequent injection or other administration. Alternatively, continuous infusion or administration sufficient to maintain appropriate and sufficient concentrations in the blood, CNS or at the site of desired therapy are contemplated.

The timing of administration may vary and may be determined by the skilled artisan or medical practitioner, based on the teaching of the specification, the clinical parameters of the patient or subject, the status or severity of the condition or disease, or the degree or nature of neural injury, involvement or compromise. Thus, improvement in neural function or enhanced protection of neurons, e.g. from death or compromise, may be enhanced by administration early in the onset or clinical demonstration of a disease, so as to minimize the extent of neurological damage or compromise. In an aspect, timing of administration is coordinated with neurological function assessments, status determination and/or other clinical evaluations so as to minimize or alleviate progression of disease of neurological impairment or damage.

The compositions are administered in a manner compatible with the dosage formulation, and in a therapeutically effective amount. The quantity to be administered depends on the subject to be treated, capacity of the subject's immune system to utilize the active ingredient, and degree or extent of deficit, including neuromotor deficit, evident or the extent of prevention or repair deemed necessary or applicable. Precise amounts of active ingredient required to be administered depend on the judgment of the practitioner and are peculiar to each individual. However, suitable dosages may range from about 0.1 to 20, preferably about 0.5 to about 10 (e.g., 0.5, 1, 2, 3, 4, 5, 6, 7, 8, 9, 10), and more preferably less than two milligrams (e.g., 0.025, 1, 2) per kilogram body weight. The milligrams of active ingredient per kilogram body weight of individual per day and depend on the route of administration. Suitable doses to neonates or infants may be less than two milligrams (e.g., 0.1, 0.2, 0.25, 0.5, 0.75, 1, 2) per kilogram, and particularly in the µg range per kilogram. Suitable regimes for initial administration and booster shots are also variable, but are typified by an initial administration followed by repeated doses at one or more hour or day intervals by a subsequent injection or other administration. Alternatively, continuous intravenous infusion sufficient to maintain suitable or effective concentrations in the blood are contemplated. Dosing in neonates or infants should be particularly catered to consider the size of the patient, volume of administration, and timing of administration, minimizing the volume, amount and dosing as much as possible.

The therapeutic compositions suitable in the methods of the invention may further include an effective amount of one or more antibody of the invention, and one or more of the following active ingredients: an antibiotic, a steroid, an immune modulator, a growth factor, a neuromodulatory agent.

Diagnostic Assays

The present invention also relates to diagnostic applications, including methods for detecting or evaluating white matter disease or injury, including PVL in neonates or infants. The antibodies and fragments provided herein may be utilized to assess, quantitate, target and/or image neurons, including in white matter disease, including PVL, affected infants, in vitro or in vivo. The present antibodies including fragments thereof, and drugs that modulate the production or activity of the antibodies and/or their subunits may possess certain diagnostic applications and may for example, be utilized for the purpose of detecting and/or measuring white matter injury, damage or death, or PVL.

The labels most commonly employed for these studies are radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA blue and Lucifer Yellow. The antibody(ies) of use in the invention or fragments thereof can also be labeled with a radioactive element or with an enzyme. The radioactive label can be detected by any of the currently available counting procedures. The preferred isotope may be selected from 3H, $^{14C,}$ 32P, $^{35}$S, $^{36}$Cl, $^{51}$Cr, $^{57}$Co, $^{58}$Co, $^{59}$Fe, $^{90}$Y, $^{125}$I, $^{131}$I, At and $^{186}$Re. Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase.

The labeled, including radiolabelled, antibodies and fragments thereof, are useful in in vitro diagnostics techniques and in in vivo radioimaging techniques and in radioimmunotherapy. In the instance of in vivo imaging, the antibodies or fragments of the present invention may be conjugated to an imaging agent rather than a radioisotope(s), including but not limited to a magnetic resonance image enhancing agent, wherein for instance an antibody molecule is loaded with a large number of paramagnetic ions through chelating groups. Examples of chelating groups include EDTA, porphyrins, polyamines crown ethers and polyoximes. Examples of paramagnetic ions include gadolinium, iron, manganese, rhenium, europium, lanthanium, holmium and ferbium. In a further aspect of the invention, radiolabelled antibodies and fragments thereof, particularly radioimmunoconjugates, are useful in radioimmunotherapy, particularly as radiolabelled antibodies for cellular therapy. In a still further aspect, the radiolabelled specific binding members, particularly antibodies and fragments thereof, are useful in radioimmuno-guided surgery techniques, wherein they can identify and indicate the presence and/or location of compromised or damaged neurons or the sites of nerve injury, during or following surgery to target or remove such cells or to transplant or administer cells to those specific sites.

Radioimmunotherapy (RAIT) has entered the clinic and demonstrated efficacy using various antibody immunoconjugates. $^{131}$I labeled humanized anti-carcinoembryonic antigen (anti-CEA) antibody hMN-14 has been evaluated in colorectal cancer (Behr T M et al (2002) Cancer 94(4Suppl): 1373-81) and the same antibody with $^{90}$Y label has been assessed in medullary thyroid carcinoma (Stein R et al (2002) Cancer 94(1):51-61). Radioimmunotherapy using monoclonal antibodies has also been assessed and reported for non-Hodgkin's lymphoma and pancreatic cancer (Goldenberg D M (2001) Crit Rev Oncol Hematol 39(1-2):195-201; Gold D V et al (2001) Crit Rev Oncol Hematol 39 (1-2) 147-54). Radioimmunotherapy methods with particular antibodies are also described in U.S. Pat. Nos. 6,306,393 and 6,331,175. Radioimmunoguided surgery (RIGS) has also entered the clinic and demonstrated efficacy and usefulness, including using anti-CEA antibodies and antibodies directed against tumor-associated antigens (Kim J C et al (2002) Int J Cancer 97(4):542-7; Schneebaum S et al (2001) World J Surg 25(12):1495-8; Avital S et al (2000) Cancer 89(8): 1692-8; McIntosh D G et al (1997) Cancer Biother Radiopharm 12 (4):287-94).

Diagnostic applications of the antibodies and fragments thereof of the invention include in vitro and in vivo applications well known and standard to the skilled artisan and based on the present description. Diagnostic assays and kits for in vitro assessment and evaluation of neurons or nervous tissue, may be utilized to diagnose, evaluate and monitor patient samples including those known to have or suspected of having white matter injury, including PVL, as or in an infant or determining the extent of cell death or injury or of a CNS tumor or cancer, including in a sample from a patient or subject. The assessment and evaluation of neurological disease status is also useful in determining the suitability of a patient for a clinical trial of a drug or for the administration of a particular neurotherapeutic or chemotherapeutic agent or an antibody of the present invention, including combinations thereof, versus a different agent or antibody.

Nucleic Acids

The present invention further provides methods wherein an isolated nucleic acid encoding an antibody, particularly a recombinant antibody, particularly a fully human antibody, is utilized in the methods of the present invention. Nucleic acid includes DNA and RNA. In a preferred aspect, the present invention provides methods utilizing a nucleic acid which codes for a polypeptide applicable in the methods, including a polypeptide antibody IgM12, IgM22, IgM42 or IgM46 as set out in FIG. 10, 11, 12 or 13 or capable of encoding the CDR regions thereof. Exemplary nucleic acid sequences encoding antibodies of use the invention and CDR regions thereof are provided, including in FIGS. 10 and 11, and include for IgM12 heavy and light chain variable regions SEQ ID NO: 9 and 10 and for IgM22 heavy and light chain variable regions SEQ ID NO: 19 and 20, and including in FIGS. 12 and 13 and for IgM42 heavy and light chain variable regions SEQ ID NO: 29 and 30, and for IgM46 heavy and light chain variable regions SEQ ID NO: 39 and 40.

The present invention may utilize constructs in the form of plasmids, vectors, transcription or expression cassettes which comprise at least one polynucleotide as above. The present invention also may utilize a recombinant host cell which comprises one or more constructs as above. A nucleic acid encoding any antibody or fragment as provided may be used in an aspect method of the present invention. Expression may conveniently be achieved by culturing under appropriate conditions recombinant host cells containing the nucleic acid. Following production by expression a specific binding member may be isolated and/or purified using any suitable technique, then used as appropriate.

Antibodies and encoding nucleic acid molecules and vectors of use according to the present invention may be provided isolated and/or purified, e.g. from their natural environment, in substantially pure or homogeneous form, or, in the case of nucleic acid, free or substantially free of nucleic acid or genes origin other than the sequence encoding a polypeptide with the required function. Nucleic acid according to the present invention may comprise DNA or RNA and may be wholly or partially synthetic.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, cancer cells, ovarian cancer cells and many others. A common, preferred bacterial host is *E. coli*. The expression of antibodies and antibody fragments in prokaryotic cells such as *E. coli* is well established in the art. Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. 'phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Short Protocols in Molecular Biology, Second Edition, Ausubel et al. eds., John Wiley & Sons, 1992. The disclosures of Sambrook et al. and Ausubel et al. are incorporated herein by reference.

As is well known in the art, DNA sequences may be expressed by operatively linking them to an expression control sequence in an appropriate expression vector and employing that expression vector to transform an appropriate unicellular host. A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., E. coli plasmids col E1, pCR1, pBR322, pMB9 and their derivatives, plasmids such as RP4; phage DNAs, e.g., the numerous derivatives of phage λ, e.g., NM989, and other phage DNA, e.g., M13 and filamentous single stranded phage DNA; yeast plasmids such as the 2u plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like. Any of a wide variety of expression control sequences— sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast a-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of E. coli, Pseudomonas, Bacillus, Streptomyces, fungi such as yeasts, and animal cells, such as CHO, YB/20, NSO, SP2/0, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products. Considering these and other factors a person skilled in the art will be able to construct a variety of vector/expression control sequence/host combinations that will express the DNA sequences of this invention on fermentation or in large scale animal culture.

A DNA sequence encoding an antibody or fragment thereof can be prepared synthetically rather than cloned. The DNA sequence can be designed with the appropriate codons for the specific binding member amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, Nature, 292:756 (1981); Nambair et al., Science, 223:1299 (1984); Jay et al., J. Biol. Chem., 259:6311 (1984). Synthetic DNA sequences allow convenient construction of genes which will express specific binding member analogs or "muteins". Alternatively, DNA encoding muteins can be made by site-directed mutagenesis of native specific binding member genes or cDNAs, and muteins can be made directly using conventional polypeptide synthesis.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

EXAMPLE 1

Animal Model of PVL

Neonatal white matter injury (nWMI), particularly Periventricular leukomalacia (PVL), is an increasingly common cause of cerebral palsy in premature infants resulting predominantly from hypoxic injury to progenitor cells, including those of the oligodendrocyte lineage. Existing mouse models utilize prolonged periods of hypoxia during the neonatal period, but this requires complex cross-fostering of pups, and prolonged hypoxia exposed mice exhibit poor growth and high mortality rates.

Given the link between hypoxic stress and the pathogenesis of PVL, a number of investigators have modeled the disease by exposing neonatal rodent pups to various degrees and durations of hypoxia (Back et al., 2006; Chahboune et al., 2009; Douglas et al., 2007; Fagel et al., 2009; Ganat et al., 2002; Kanaan et al., 2006; Zhou et al., 2008). In both mice and rats, exposure to 9-11% oxygen for 7 to 30 days during the first month of life yields a spectrum of white matter disease that closely resembles PVL seen in human ELBWs. Specifically, chronic hypoxia reduces the volumes of the cerebral cortex, subcortical white matter and the corpus callosum, followed by progressive ventriculomegaly (Back et al., 2006; Ment et al., 1998; Turner et al., 2003; Weiss et al., 2004).

While these murine models are well established and valuable for the study of PVL, they are fraught with limitations. First, the hypoxic exposure most typically begins at postnatal day 3 (P3) and continues for 8 to 11 days (Back et al., 2006; Fagel et al., 2009; Fagel et al., 2006; Jablonska et al., 2012; Li et al., 2009; Scafidi et al., 2014; Turner et al., 2003; Weiss et al., 2004), a period that correlates with human brain development between 32 weeks gestation through the first year of postnatal life (Dobbing and Sands, 1979; Hagberg et al., 2002; Romijn et al., 1991; Semple et al., 2013). Thus, this exposure strategy does not selectively affect the early phases of OL development relevant to human PVL. Second, the timing and duration of this hypoxic exposure reduces skeletal muscle mass, body and brain weights, and overall survival, suggesting that malnourishment and/or systemic illness may confound interpretation in these models (Lan et al., 2011; Ment et al., 1998; Radom-Aizik et al., 2013). Moreover, attempts to obviate these two confounding factors, such as co- or cross-fostering neonatal mice by dams of another strain (Back et al., 2006; Turner et al., 2003) add cost and an undesirable degree of complexity to the in vivo study of PVL.

A simplified model of nWMI and PVL was developed in which neonatal mice are exposed to low oxygen (10% oxygen) from postnatal day 3 (P3) to P7, which corresponds to the developmental phase of the human brain between pre-term and term infancy (gestational weeks 32-36). It was hypothesized that this relatively brief hypoxic exposure corresponding to the developmental phase of the human brain between preterm and term infancy would be sufficient to induce neuropathological and functional deficits consistent with human PVL. The data corroborate this hypothesis; specifically, hypoxia-exposed mice displayed severe hypomyelination throughout brain and spinal cord, delayed cerebellar development and persistent neuromotor deficits. While the neuromotor phenotype persisted, confounding factors that have been reported to occur with longer hypoxic exposures, such as severe decreases in body weight, brain weight and low survival rates, were ameliorated.

This model's hypoxia-exposed mice display impaired myelination of the cerebrum, spinal cord and cerebellum, as well as motor and behavioral abnormalities that persist into adulthood. Additional findings include reduced expression of oligodendrocyte progenitor cell (OPC) markers as well as late-onset microglial activation. Together these findings suggest that a brief hypoxic exposure is sufficient to induce experimental PVL or nWMI in neonatal mice, thus providing a model to test new therapeutic modalities.

Immediately following hypoxia treatment, cell death was evident in multiple brain regions, most notably in superficial and deep cortical layers as well as the subventricular zone progenitor compartment. PDGFαR, Nkx2.2, and Olig2 positive oligodendrocyte progenitor cell were significantly reduced until postnatal day 27. In addition to CNS dysmyelination we identified a novel pathological marker for adult hypoxic animals that strongly correlates with life-long neuro-motor deficits. Mice reared under hypoxia reveal an abnormal spinal neuron composition with increased small and medium diameter axons and decreased large diameter axons in thoracic lateral and anterior funiculi. Differences were particularly pronounced in white matter motor tracts left and right of the anterior median fissure. Our findings suggest that 4 days of exposure to hypoxia are sufficient to induce experimental nWMI or PVL in CD1 mice, thus providing a model to test new therapeutics. Pathological hallmarks of this model include early cell death, decreased OPCs and hypomyelination in early postnatal life, followed by dysmyelination, abnormal spinal neuron composition, and neuro-motor deficits in adulthood.

In the present study, we tested whether exposure of neonatal mice to 4 days of hypoxia (abbreviated hypoxia) from P3 to P7 in an outbred CD1 mouse strain is sufficient to induce the neuropathological and functional deficits consistent with human nWMI, particularly PVL. We also evaluated how cross-fostering neonatal mice during and after hypoxia impacts survival, growth, and myelination. In addition, we identified pathological changes of myelin and axons that correlate with persistent neuro-motor deficits in our model of PVL/nWMI.

Methods

Experimental animals: Timed-pregnant CD1 mice were obtained from Charles River Laboratories and maintained in usual conditions. The litter size used until P21 was 12 per dam. All animals were cared for according to all local, state and federal regulations and used according to a protocol approved by the Mayo Clinic Institutional Animal Care and Use Committee (IACUC) and the National Institute of Health.

Chronic Hypoxia-Induced White Matter Disease Model

Abbreviated or Brief hypoxia: Litters of CD1 mice were randomly assigned for rearing in hypoxia or room air (normoxia) from P3 to P7, using a litter size of 12 for all dams throughout the study. For litters assigned to hypoxic rearing, cages were placed within an acrylic chamber that was ventilated with nitrogen to lower ambient oxygen tension to 10+/−0.5%. On P7, these cages were removed from the chamber, and mice were subsequently reared in usual, normoxic conditions. Litters assigned to normoxia were reared in usual conditions throughout the study. Mice from both exposure groups were randomly sacrificed at P13, P27 or P80 for use in the histological and molecular studies described below. At the time of sacrifice, body weights and cerebral weights (cerebellums and brain stems were removed) were measured. Additional mice were randomly selected and maintained in usual conditions for use in neuromotor testing at P21, P43 and P80.

Standard hypoxia: In order to compare our brief hypoxia model with a well-established model of PVL, we randomly assigned litters of CD1 mice for rearing in hypoxia or normoxia from P3 to P12, again using a litter size of 12 for all dams. As above, body weight and cerebral weights were measured at the time of sacrifice. Proper functioning of the oxygen sensor, control unit and ventilation system was verified by BioSpherix Ltd (Lacona, N.Y.) before the assignment of all litters used in the below experiments and oxygen levels were monitored continuously over four days.

Brain and spinal cord pathology: Brains and spinal cords were harvested at P13 and P27 and immediately immersed in 4% paraformaldehyde for paraffin processing. Paraffin-embedded sections (5 μm) were stained with Luxol Fast Blue (LFB) and Periodic Acid-Schiff (PAS) to assess the general histology and myelination of these structures. Micrographs were prepared using an Olympus DP73 camera attached to an Olympus AX70 research microscope (Olympus America Inc., Center Valley, Pa., USA). (n=20 hypoxic animals P13; 14 normoxic animals P13; 4 normoxic animals P27; 4 hypoxic animals P27).

Immunohistochemistry and Cell Counts: Brains harvested from mice were post-fixed overnight in 4% PFA, cryoprotected in 30% sucrose, processed for OCT embedding and sectioned at 40 μm as previously described. For immunohistochemistry, standard methods with antigen retrieval in sodium citrate were used. Antibodies used in this study included: anti-Olig2 (Millipore 1:500), anti-myelin basic protein (MBP; Millipore 1:500), anti-Cleaved Caspase 3 (CC3; Cell Signaling 1:500), and anti-Nkx2.2 (Iowa Hybridoma 1:50) Immunoreactivity was detected by incubation with appropriate Alexa-conjugated secondary antibodies (Molecular Probes—Life Technologies). Images of brain sections were captured using a Nikon NIE fluorescent microscope. The number of immune-positive cells per 100 µm2 area was quantified using Nikon Elements analysis software. Statistical significance was determined using Student's t-test and presented as mean cells per field. All studies were blinded and performed on coded sections (n=6 hypoxic+6 normoxic animals for IHC and Western blotting (each)).

Quantification of myelin-associated gene transcripts: Cerebral hemispheres of each animal were bisected, with one used for measurement of gene expression levels and the other for measurement of protein levels (described below). In analogy to nWMI/PVL as it is seen in human neonates (males display a more severe nWMI/PVL phenotype than females), molecular analyses beyond the weaning age of P21 were performed using the brains of male mice only. For gene-expression studies, total RNA was extracted according to the manufacturer's recommendations (TRIzol reagent, Life Technologies) and then was reverse-transcribed and amplified in one step (LightCycler 408, Roche Applied Science). Each reaction contained 12.5 µL of 2× master mix (QuantiFast SYBR Green RT-PCR Kit, Qiagen), 0.25 µL Quantifast RT Mix (Qiagen), 100 ng RNA, 1 µM of each forward and reverse primer (Table 1) in molecular grade water. Samples were run in duplicate, and the mean crossing point for each transcript was determined and normalized to Gapdh (deltaCt). DeltaCt values were used to calculate relative fold-change using the 2-[delta][delta]Ct method (Schmittgen and Livak, 2008). Calculation of p-values used Student's unpaired, two-tailed t-test (GraphPad 6, Prism); $p<0.05$ was considered significant. (n=6 normoxic and 6 hypoxic animals P13; n=6 normoxic and 6 hypoxic animals P27; n=6 normoxic and 6 hypoxic animals P80, normoxic and hypoxic animals were from two independent experimental setups).

Quantification of myelin-associated proteins: Total protein was isolated from each cerebrum, with brain lysates brought to a concentration of 150 µg/µL in ice-cold lysis buffer [1× RIPA buffer supplemented with 10 mM NaF, 1 mM MgCl2, 100 µg/mL DNase I and a protease inhibitor cocktail (cOmplete™, Roche)]. Lysates were homogenized on ice by trituration through a 27-gauge needle before incubation for 30 minutes on ice. Detergent-insoluble material and brain lipids were removed by serial centrifugation (four rounds at 20,000 g for 10 minutes at 4° C.). For immuno-blotting, 150 ug brain tissue from each animal was loaded into each well of a 4-20% gradient gel and analyzed as previously described (Watzlawik et al., 2013). Thus, each lane represented an individual animal. For quantification, three independent experiments were performed with lysates from six to eight individual mouse brains from each exposure group Immunoblots were analyzed by densitometry (BioRad, Quantity One™), with protein levels normalized to levels of β-actin. Student's t-test or ANOVA compared normalized protein levels between experimental groups (Sigma Plot™ and Sigma Stat®, Systat Software). Hypoxic and normoxic animals were from two independent experimental setups per time point: 4 hypoxic+4 normoxic animals from set 1, 4 hypoxic+4 normoxic animals from set 2. All data analyses were performed in a blinded fashion (i.e., without knowledge of exposure and rearing assignment).

Axon counts (thick sections): 6 month old animals were intracardially perfused with Trumps fixative. Spinal cords were dissected and cut into 1 mm thick blocks, oxidized with osmium, dehydrated and embedded in araldite. Blocks were cut into 2 um thick sections, slide mounted and myelin stained with paraphenylene diamine (PPD). Microscopic images were taken at a 60× magnification from lateral and anterior funiculi of thoracic spinal cord sections and automated axon counts were performed as previously described. As quality control, axon counts were verified manually from one slide per animal and compared to the software based outcome (animal numbers: 4 hypoxic and 4 normoxic animals).

Myelin quality (g-ratios, dysmyelination): Araldite embedded spinal cord blocks from 6 month old mice (see axon counts) were trimmed down to the lower anterior spinal cord funiculi (lower left or lower right quadrant) and sent to the Mayo electron microscopy core facility. Blocks were cut into thin sections, placed on carbon coated copper grids and stained with uranyl acetate. 20 representative electron microscopic images were taken per block (3000× or 8000×). The person taking the images was blinded to the experimental groups (JOW). Axon diameters, myelin thickness for g-ratios and dysmyelinated axons were determined from all axons per image using NIH Image J irrespective of the axon diameter with >100 axons per animal analyzed (n=4 mice per group). In addition, wmanually analyzed numbers of collapsed axons (whorls) and stressed axons (identified by intensively stained mitochondria) per treatment group.

Neuromotor assessment: All assessments of neurologic function were performed in a blinded fashion without knowledge of the rearing strategy of each experimental group.

Hanging wire tests (single wire and mesh wire): To evaluate motor function and limb strength, we performed two different hanging wire tests: for the mesh wire test, a mouse was placed in the center of a 50×50 cm wire grid, which was then gently inverted, and for the single wire test, an animal's forepaws were placed at the center of a 2 m long single wire. Each attempt by the mouse to hang from the wire is considered a trial, which is completed either when the mouse falls, sustains its grip up to the cut-off point of 180 seconds or reaches the end of the wire (in the case of the single wire) (Maurissen et al., 2003; Shinzawa et al., 2008). Each mouse performed three trials per time point, with the best performances used in comparisons between exposure groups as shown by other investigators (Maurissen et al., 2003).

Rotarod test: To assess sensorimotor coordination, mice with no prior exposure to a rotating rod were placed upon a rod that was accelerated quickly from zero to five revolutions per minute, then gradually from five to 20 revolutions per minute. We considered each attempt by the mouse to remain on the rotating rod as a trial, completed when the mouse fell or had sustained itself on the rod up to the cut-off point of 180 seconds. We recorded the latency to fall for each of three trials and used the best performance in comparisons between exposure groups (Buitrago et al., 2004; Jones and Roberts, 1968a; Jones and Roberts, 1968b; Lalonde et al., 2003).

Grip-strength meter test: The effect of hypoxia on skeletal muscular strength was assessed by a grip-strength test (Meyer et al., 1979). The grip-strength apparatus (BioSeb, Chaville, France) consisted of a wire crossbar connected to an isometric force transducer or dynamometer. Male mice at P90 were lifted by their tails until their forepaws could grasp the grid. The mice were then gently pulled backward by the tail until the bar was released. The maximal force exerted by the mouse before losing grip was recorded. The mean of three measurements for each animal was calculated and normalized to the animal's body weight, with the resulting data expressed as Newtons per gram (N/g) (Vetrone et al., 2009).

Spontaneous activity monitoring: Spontaneous locomotor activity was recorded with the Digiscan open field apparatus (Omnitech Electronics; Columbus, Ohio) and Versamax software, v.4.12-1AFE (Accuscan Instruments, Inc., Columbus, Ohio). The apparatus consists of six acrylic cages (40×40×30.5 cm) supported by a metal frame that holds two sets of photo cells. The device measures the number of discrete horizontal and vertical movements by tabulating the number of projected infrared beam interruptions. In all cages, mice were exposed to identical environmental conditions: freely accessible food and water, a normal 12 h light/dark cycle and 70° F. ambient temperature. Groups of age-matched male CD1 mice (n=3 for group responses, or n=1 for individual response) were placed in the center of each cage at P90. Spontaneous activity was monitored over a period of six consecutive days, with data collected as number of beam breaks per 1 hour blocks. The total horizontal and vertical activities were recorded using the Versadat software, v.3.02-1AFE (Accuscan Instruments) (Denic et al., 2011).

Body composition: Whole body composition (total fat mass and lean body mass) was determined by use of nuclear magnetic resonance imaging (MRI) technology produced by Echo Medical Systems LTD (Houston, Tex.). P90 male CD1 mice were placed in an MRI tube and analyzed on the accumulation 2 setting, which is specific for mice, as previously described (Kovner et al., 2010).

Statistical Analyses: The assumption of normality was tested with the Shapiro-Wilk test for normality prior to additional analysis (Sigma Plot v11.0). Normally distributed data were analyzed by Student's unpaired, two-tailed t-test (2 groups) or ANOVA (>2 groups). Data not normally distributed were analyzed using the Mann-Whitney U test (2 groups) or Kruskal-Wallis one-way ANOVA (>2 groups). A probability of p<0.05 was set as the level of significance for all comparisons.

Results

A mouse model of white matter injury, particularly manifested as Periventricular Leukomalacia (PVL), was developed that uses an abbreviated exposure to chronic hypoxia and induces hypomyelination and persistent motor deficits in male neonatal mice. Neonatal mice are exposed to chronic hypoxia (10% $O_2$) for a defined and abbreviated period of time postnatally, in particular from postnatal day 3 (P3) to postnatal day 7 (P7). The advantages of our recently developed model include: (i) a strongly improved survival rate of neonatal mice (CD1); (ii) the use of outbred CD1 mice with higher litter sizes compared to inbred C57/B16 mice; (iii) the model does not require co- or cross-fostering of neonatal mice; (iv) the therapeutic window based on myelin markers is 20 days post injury and >6 month based on motor phenotype assessment, which is in line with or potentially better than existing models of the disease.

This model allows compound testing in higher numbers of animals, is in line with FDA toxicology regulations (use of outbred CD1 mice). The model is also simpler and more cost-effective compared to more established animal models using chronic hypoxia.

In the new model, animals (mice) are reared under hypoxia from P3 to P7, or a comparatively short period of hypoxia. This short/abbreviated hypoxia is compared to long hypoxia (rearing under hypoxia from P3 to P12 in TABLE 1 below. Survival rate of animals reared P3 to P12 under hypoxia is only 35% versus 100% for animals reared normally or under hypoxia P3 to P7 only. The body weight and brain weight were reduced under all hypoxic conditions, but were far more significantly reduced under hypoxia P3 to P12.

TABLE 1

| Long hypoxia vs Abbreviated (short) hypoxia | | | |
|---|---|---|---|
| | Short hypoxia (P3→P7) | Long hypoxia (P3→P12) | Normoxia |
| Survival rate (in percent) | 100 (102/102) (P12) | 35 (7/20) (P12) | 100 (102/102) |
| Body weight (g) (mean ± std.-dev.) | 5.12 ± 0.08 (P12) (abbreviated hypoxia vs long hypoxia, (p < 0.0001) | 2.90 ± 0.30 (P12) (normoxia vs long hypoxia, (p < 0.0001) | 7.20 ± 0.60 (P12) 7.18 ± 0.09 (P13) |
| Brain weight (mean ± std.-dev.) | 0.33 ± 0.005 (P12) (abbreviated hypoxia vs long hypoxia, (p < 0.0001) | 0.21 ± 0.03 (P12) (normoxia vs long hypoxia, (p < 0.0001) | 0.39 ± 0.03 (P12) 0.42 ± 0.004 (P13) |

Chronic Hypoxia-Induced White Matter Disease Model

The time course of the abbreviated hypoxia-induced PVL model is diagrammed in FIG. 1A. CD1 mice were randomly assigned to hypoxia or room air (normoxia). The litter size for all dams used was 12. Hypoxic mice were reared from P3 to P7 under hypoxia. The cages of litters assigned to hypoxia were placed within an acrylic chamber that was ventilated with nitrogen such that the ambient oxygen tension was lowered to 10+/−0.5%. Litters assigned to normoxia were reared in usual, normoxic conditions. On P7, the litters assigned to hypoxia were removed from the chamber and subsequently reared under normoxic conditions.

Mice from both exposure groups (normoxia and hypoxia) were sacrificed at P7, P13, P27 or P80 for use in histological and molecular studies. At the time of sacrifice, body and brain weights were measured and the results are depicted in FIGS. 1B and 1C respectively. Body and brain weights were significantly different at all time points after the assignment to hypoxia except P80 and P3 (before the assignment to either hypoxia or normoxia) (n=200 mice assigned to hypoxia or normoxia).

Interestingly, the body weights and brain weights of mice immediately following hypoxia exposure at P7 (abbreviated duration mean=2.76 g, Table 2) or at P12 (long duration mean=2.90 g, Table 1) were not statistically different from P3 weights prior to treatment assignment (hypoxia mean=2.63 g, normoxia mean=2.52 g, Table 2). This data suggest a complete growth arrest in response to hypoxia. Given the apparent survival and growth benefit in abbreviated hypoxia, we followed subsequent litters of mice for extended periods of time to compare their body mass and brain growth compared to mice reared in room air. Hypoxic exposure impaired growth in body weight and brain weight for many weeks, although normalization did occur by adulthood (P80) (FIG. 1; Table 2).

Body and brain weights of mice exposed to short (P3 to P7) hypoxia are depicted are fully tabulated in TABLE 2 below.

TABLE 2

Body and brain weights of mice exposed to abbreviated/short hypoxia

| | Body weight (g) (mean ± std.-dev.) | | Brain weight (g) (mean ± std.-dev.) | |
|---|---|---|---|---|
| | 10% O2 | 21% O2 | 10% O2 | 21% O2 |
| P3 - before assignment | 2.63 ± 0.05 | 2.52 ± 0.04 (p = 0.071) | | |
| P7 | 2.76 ± 0.04 | 4.30 ± 0.06 (p < 0.0001) | 0.22 ± 0.005 | 0.31 ± 0.008 (p < 0.0001) |
| P13 | 5.12 ± 0.08 | 7.18 ± 0.09 (p < 0.0001) | 0.33 ± 0.005 | 0.42 ± 0.004 (p < 0.0001) |
| P21 male | 9.27 ± 0.32 | 13.81 ± 0.35 (p < 0.0001) | | |
| P27 male | 16.37 ± 0.35 | 21.71 ± 0.43 (p < 0.0001) | 0.41 ± 0.008 | 0.46 ± 0.005 (p < 0.0001) |
| P43 male | 29.52 ± 0.28 | 30.78 ± 0.32 (p = 0.0041) | | |
| P80 male | 36.51 ± 0.92 | 38.12 ± 0.81 (p = 0.1943) | 0.50 ± 0.01 | 0.52 ± 0.01 (p = 0.3377) |

A known disadvantage of the more established hypoxia model is the need to co- or crossfoster hypoxic neonatal mice to avoid severe malnutrition or ultimately death. It was hypothesized that C57/B16 dams neglect their offspring when exposed to hypoxic stress. Although the survival rate in our model was 100% (therefore obviating the need for cross fostering in our paradigm), cross fostering could potentially impact post-hypoxic growth and therefore myelination. To eliminate the influence of litter size on nutrient availability we culled litters to 6 per group immediately prior to assignment to hypoxia at P3. To examine maternal impact on growth during and after 4 days of hypoxia, CD1 pups were raised with either a C57/B16 dam (cross fostered) or CD1 dam (non-cross fostered). In addition, we evaluated C57/B16 pups cross fostered with a CD1 dam. Experiments were also performed for all assignment groups under normoxia. We measured survival, body weight, and performed western blot analysis of myelin proteins (see following section) (FIG. 2A-2D).

Surprisingly, the survival rates of neonatal mice in all assignment groups were identical (100% survival), including those litters fostered by C57B1/6 dams. Body weight ratios of normoxic compared to hypoxic neonatal mice were similar in all assignment groups at P7 ((normoxic: hypoxic): 2.0 (cross-fostered C57/B16 pups), 1.9 (cross-fostered CD1 pups), 1.8 (noncross-fostered CD pups)) but were significantly different at P13 ((normoxic: hypoxic: 1.6 (cross-fostered C57/B16 pups), 2.2 (cross-fostered CD1 pups), 1.4 (non-cross-fostered CD1 pups)). It is of note that non-cross-fostered CD1 mice showed the lowest body weight ratios of normoxic versus hypoxic mice at both time points, indicating the best growth rates post hypoxia (FIG. 2A-2D).

It is of note that all CD1 dams lost approximately 25% of their body weight during the 4 day exposure to hypoxia compared to their body weight before hypoxia and compared to normoxic control dams (data not shown). This data suggested that the dams are likely responsible for malnourishment of neonatal pups under hypoxia and strongly questions co- or cross-fostering of neonatal mice during the hypoxic treatment.

In brief, results demonstrate improved survival, body, and brain growth under four days of hypoxia compared with 10 days of hypoxia. Body and brain weights of neonatal mice were lower in the hypoxic groups until mouse adulthood. No obvious beneficial effect of cross-fostering on survival rates or weight loss was observed during the 4 day hypoxic insult without obvious differences between mouse strains. However, weight gain of neonatal mice post injury occurred faster with CD1 dams. Importantly, non-cross-fostered neonatal CD1 mice demonstrated the best weight gain post hypoxia with the smallest interference of malnutrition.

Chronic Hypoxia Induces Global Hypomyelination in Cerebrum, Spinal Cord and Cerebellum.

Figure 3:
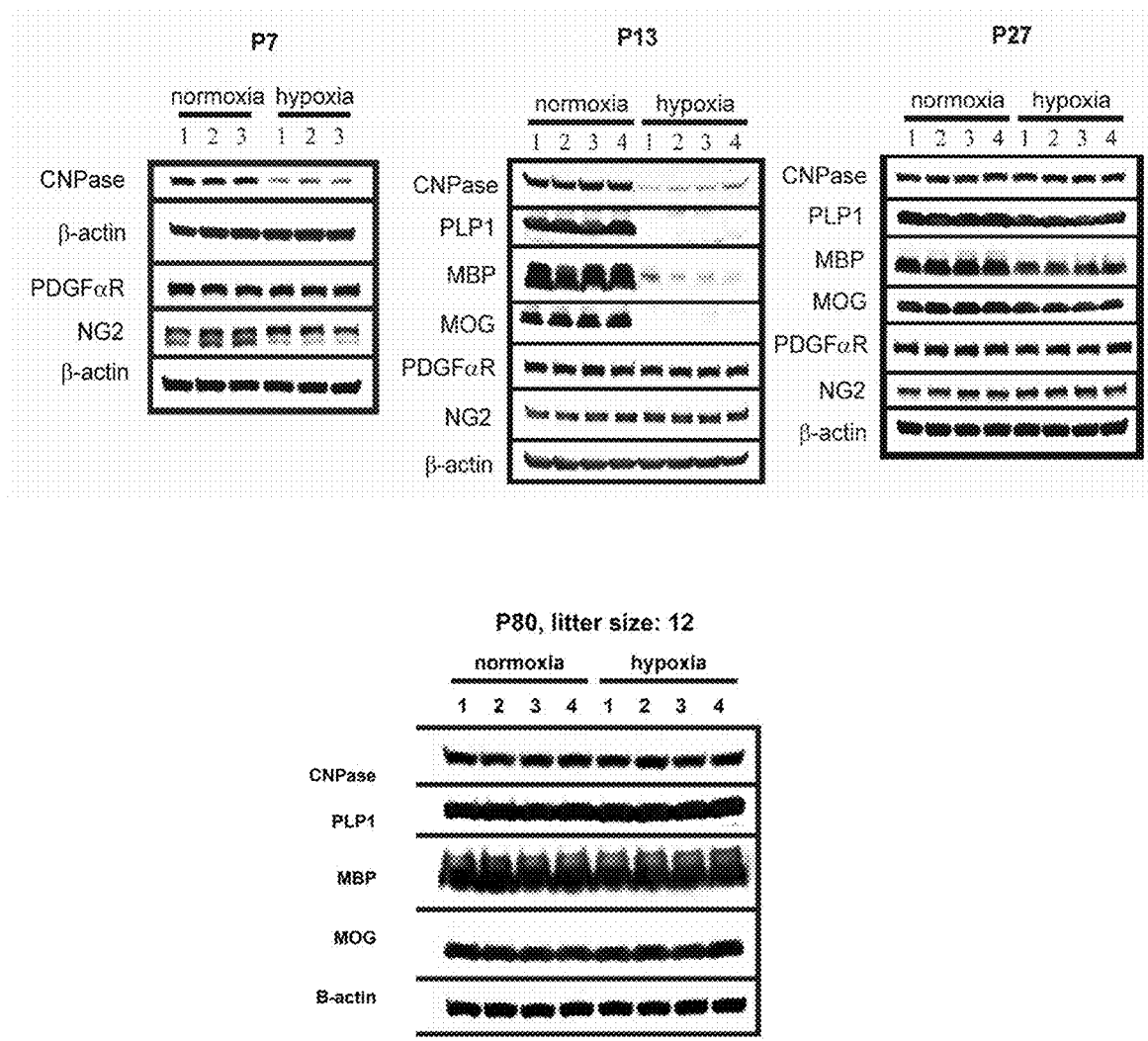
FIG. 3A-3C. (A) provides Western blots of normoxia and hypoxia mice at each of P7, P13, P27 and P80. Each lane represents an individual animal, with 1.5 mg brain tissue loaded. Proteins evaluated are CNPase, β-actin (control), PDGFαR, NG2, PLP1, MBP and MOG as indicated. (B) Lipid staining luxol fast blue (LFB) of tissue from cortex and spinal cord of normoxia and hypoxia mice. Black arrows point to myelin, which is reduced in hypoxic animals. (C) Lipid staining luxol fast blue (LFB) of tissue from cerebellum of normoxia and hypoxia mice. Black arrows point to myelin, which is reduced in hypoxic animals. Yellow arrows denote the cerebellar granular layer (EGL), which is substantially thicker in hypoxia-reared animals.

CD1 mice assigned to hypoxia (P3→P7) or normoxia were sacrificed at P7, P13, P27 and P80 and assessed for myelin markers and myelin protein expression. The results are depicted in FIG. 3A-3C (P80 data not shown). Western blot study results are shown in FIG. 3A. Whole cerebra from hypoxic and control mice were analyzed by Western blot using 1.5 mg of tissue per lane. Each lane is representative for an individual animal. Myelin proteins CNPase (immature OL marker 2',3'-cyclic-nucleotide 3'-phosphodiesterase), PLP1, MBP and MOG were used to represent whole myelin; markers PDGFαR and NG2 represent oligodendrocyte progenitor cells (OPCs). The representative Western blots at different time points show reduced levels of myelin marker CNPase already at P7 with PLP1, MBP and MOG undetectable at this time point. Similar to CNPase, the late OPC marker NG2 and the OPC/immature OL marker Oligo-2 were significantly reduced at P7. Hypomyelination in hypoxic mice peaked around P13 with all myelin markers strongly reduced. At P27 myelin markers were still significantly different between both groups (all myelin proteins) (n=16 per age group). The levels of these proteins did not normalize until approximately P80. In contrast, OPC markers showed minor or no differences between both assignment groups at all time points with the exception of NG2 at P7. In summary, these results demonstrate that neonatal CD1 mice exposed to four days of hypoxia develop significant hypomyelination that persists through the first month of postnatal life.

To quantify the extent to which brief hypoxia reduced the elaboration of cerebral myelin, we measured the expression levels of myelin-associated gene transcripts. RT-PCR for various myelin-related gene transcripts was conducted on samples at P13 from mice under hypoxia (P3→P7) and under normoxia conditions. Primers utilized in the RT-PCR are provided in TABLE 3. Results are tabulated in TABLE 4. Brief hypoxia strongly down-regulated the gene expression of myelin markers PLP1, MBP and MOG at P13.

TABLE 3

RT-PCR Primers

| Gene | Primer Pair | |
|---|---|---|
| PLP-1 | forward 5'-GCTTTCCCTGGCAAGGTTTG-3' | (SEQ ID NO: 41) |
| | reverse 5'-AGCTCAGAACTTGGTGCCTC-3' | (SEQ ID NO: 42) |
| MBP | forward 5'-GGCAAGGTACCCTGGCTAAA-3' | (SEQ ID NO: 43) |
| | reverse 5'-AAATCTGCTGAGGGACAGGC-3' | (SEQ ID NO: 44) |
| MOG | forward 5'-ATCGCACTTGTGCCTACGAT-3' | (SEQ ID NO: 45) |
| | reverse 5'-GCTCCAGGAAGACACAACCA-3' | (SEQ ID NO: 46) |
| Beta-actin | forward 5'-CCACCATGTACCCAGGCATT-3' | (SEQ ID NO: 47) |
| | reverse 5'-AGGGTGTAAAACGCAGCTCA-3' | (SEQ ID NO: 48) |
| PDGFαR | forward 5'-AAAATGCGGGTTTTGAGCCC-3' | (SEQ ID NO: 49) |
| | reverse 5'-CGTTGGGGTCGTCTTCTTCA-3' | (SEQ ID NO: 50) |
| Olig-1 | forward 5'-GCTCCCCAACAGTGTCTACC-3' | (SEQ ID NO: 51) |
| | reverse 5'-TCGGCTACTGTCAACAACCC-3' | (SEQ ID NO: 51) |

TABLE 4

Fold-change in gene transcripts at P13, as detected by RT-PCR

| gene | Fold change under hypoxia P13 | Fold change under hypoxia P27 | Fold change under hypoxia P80 |
|---|---|---|---|
| PLP-1 | 0.26 (unpaired t-test; P value: 0.0013) | 1.13 (unpaired t-test; P value: 0.1711) | 0.84 (P value: 0.159) |
| MBP | 0.27 (unpaired t-test; P value: 0.0027) | 1.18 (unpaired t-test; P value: 0.8596) | 0.98 (P value: 1.00) |
| MOG | 0.26 (unpaired t-test; P value: 0.0007) | 1.18 (unpaired t-test; P value: 0.2689) | 0.87 (P value: 0.385) |
| PDGFRα | 0.78 (unpaired t-test; P value: 0.1553) | | |
| Olig-1 | 0.68 (unpaired t-test; P value: 0.1186) | | |

Densitometric testing was conducted on Western blot analyses for various CNS proteins on cerebrums of hypoxic-reared mice. The results are tabulated below for each of time points P7, P13, P27 and P80 in TABLES 5-8 below.

TABLE 5

Densitometric analysis of Western blots from cerebrum at P7

| CNS protein | 10% O2 | 21% O2 | Fold change rel. to control | Statistical analysis |
|---|---|---|---|---|
| CNPase | 0.20 ± 0.04 | 0.47 ± 0.15 | 0.43 | P = 0.002 |
| PLP-1 | 0.24 ± 0.05 | 0.26 ± 0.05 | 0.94 | P = 0.588 |
| MBP | 0.20 ± 0.06 | 0.27 ± 0.09 | 0.76 | P = 0.189 |
| Cleaved caspase-3 | 0.54 ± 0.07 | 0.38 ± 0.12 | 1.43 | P < 0.022 |
| PDGFRα | 0.34 ± 0.04 | 0.40 ± 0.14 | 0.85 | P = 0.302 |
| NG2 | 0.34 ± 0.05 | 0.44 ± 0.06 | 0.77 | P = 0.007 |
| Olig-2 | 0.55 ± 0.10 | 0.74 ± 0.14 | 0.74 | P = 0.017 |
| Olig-1 | 0.29 ± 0.09 | 0.34 ± 0.09 | 0.85 | P = 0.054 |
| GFAP | 0.16 ± 0.05 | 0.30 ± 0.05 | 0.54 | P < 0.001 |
| BS lectin | 0.29 ± 0.05 | 0.37 ± 0.13 | 0.79 | P = 0.184 |
| b3tubulin | 0.28 ± 0.03 | 0.19 ± 0.03 | 1.51 | P < 0.001 |
| MAP-2 | 0.22 ± 0.03 | 0.25 ± 0.05 | 0.89 | P = 0.266 |
| Double-cortin | 0.58 ± 0.02 | 0.44 ± 0.04 | 1.33 | P < 0.001 |

TABLE 6

Densitometric analysis of Western blots from cerebrum at P13

| CNS protein | 10% O2 | 21% O2 | Fold change rel. to control | Statistical analysis |
|---|---|---|---|---|
| CNPase | 0.29 ± 0.08 | 1.08 ± 0.14 | 0.27 | P < 0.001 |
| PLP-1 | 0.09 ± 0.09 | 1.44 ± 0.45 | 0.06 | P < 0.001 |
| MBP | 0.10 ± 0.10 | 1.07 ± 0.18 | 0.09 | P < 0.001 |
| MOG | 0.77 ± 0.32 | 1.31 ± 0.13 | 0.59 | P < 0.001 |
| PDGFRα | 0.65 ± 0.07 | 0.72 ± 0.07 | 0.90 | P = 0.048 |
| NG2 | 0.72 ± 0.11 | 0.71 ± 0.07 | 1.03 | P = 0.627 |
| Olig-2 | 0.47 ± 0.06 | 0.56 ± 0.06 | 0.85 | P = 0.019 |
| Olig-1 | 0.33 ± 0.09 | 0.47 ± 0.07 | 0.70 | P = 0.005 |
| GFAP | 0.68 ± 0.14 | 0.65 ± 0.17 | 1.05 | P = 0.680 |
| BS lectin | 0.43 ± 0.12 | 0.37 ± 0.07 | 1.15 | P = 0.300 |
| b3tubulin | 0.31 ± 0.04 | 0.35 ± 0.06 | 0.90 | P = 0.169 |
| MAP-2 | 0.55 ± 0.11 | 0.60 ± 0.13 | 0.93 | P = 0.479 |
| Double-cortin | 0.55 ± 0.05 | 0.47 ± 0.02 | 1.18 | P < 0.001 |
| NCAM | 0.97 ± 0.10 | 1.04 ± 0.07 | 0.93 | P = 0.118 |
| calbindin | 0.45 ± 0.13 | 0.72 ± 0.14 | 0.62 | P = 0.001 |
| Ki67 | 0.43 ± 0.14 | 0.15 ± 0.05 | 2.50 | P < 0.001 |

TABLE 7

Densitometric analysis of Western blots from cerebrum at P27

| CNS protein | 10% O2 | 21% O2 | Fold change rel. to control | Statistical analysis |
|---|---|---|---|---|
| CNPase | 0.25 ± 0.04 | 0.33 ± 0.05 | 0.77 | P = 0.016 |
| PLP-1 | 0.49 ± 0.05 | 0.59 ± 0.08 | 0.83 | P = 0.026 |
| MBP | 0.28 ± 0.02 | 0.45 ± 0.04 | 0.62 | P < 0.001 |
| MOG | 0.30 ± 0.03 | 0.36 ± 0.05 | 0.82 | P = 0.026 |
| PDGFRα | 0.57 ± 0.10 | 0.63 ± 0.03 | 0.91 | P = 0.310 |
| NG2 | 0.61 ± 0.08 | 0.60 ± 0.05 | 1.02 | P = 0.770 |
| Olig-2 | 0.40 ± 0.05 | 0.45 ± 0.06 | 0.89 | P = 0.187 |
| Olig-1 | 0.66 ± 0.05 | 0.62 ± 0.05 | 1.05 | P = 0.312 |
| GFAP | 0.51 ± 0.21 | 0.62 ± 0.14 | 0.83 | P = 0.319 |
| BS lectin | 0.73 ± 0.14 | 0.30 ± 0.06 | 2.45 | P < 0.001 |
| b3tubulin | 0.21 ± 0.01 | 0.20 ± 0.02 | 1.07 | P = 0.116 |
| MAP-2 | 1.24 ± 0.07 | 1.20 ± 0.06 | 1.03 | P = 0.358 |
| Double-cortin | 0.37 ± 0.05 | 0.19 ± 0.04 | 1.94 | P < 0.001 |
| NCAM | 0.68 ± 0.12 | 0.69 ± 0.10 | 0.99 | P = 0.891 |
| calbindin | 0.32 ± 0.07 | 0.37 ± 0.07 | 0.87 | P = 0.247 |

TABLE 8

Densitometric analysis of Western blots from cerebrum at P80

| CNS protein | 10% O2 | 21% O2 | Fold change rel. to control | Statistical analysis |
|---|---|---|---|---|
| CNPase | 1.29 ± 0.10 | 1.09 ± 0.23 | 1.18 | P = 0.043 |
| PLP-1 | 0.38 ± 0.05 | 0.33 ± 0.07 | 1.15 | P = 0.128 |
| MBP | 0.20 ± 0.03 | 0.20 ± 0.04 | 1.04 | P = 0.602 |
| MOG | 0.37 ± 0.06 | 0.41 ± 0.05 | 0.91 | P = 0.166 |
| PDGFRα | 1.85 ± 0.16 | 1.48 ± 0.46 | 1.25 | P = 0.130 |
| NG2 | 0.42 ± 0.06 | 0.30 ± 0.06 | 1.40 | P = 0.002 |
| Olig-2 | 0.41 ± 0.07 | 0.43 ± 0.08 | 0.96 | P = 0.661 |
| Olig-1 | 0.20 ± 0.03 | 0.13 ± 0.04 | 1.60 | P = 0.001 |
| GFAP | 1.21 ± 0.42 | 0.82 ± 0.38 | 1.47 | P = 0.073 |
| BS lectin | 0.66 ± 0.21 | 0.42 ± 0.24 | 1.57 | P = 0.051 |
| b3tubulin | 0.28 ± 0.03 | 0.21 ± 0.03 | 1.34 | P < 0.001 |
| MAP-2 | 0.63 ± 0.09 | 0.50 ± 0.08 | 1.26 | P = 0.008 |
| Doublecortin | 0.22 ± 0.09 | 0.17 ± 0.11 | 1.27 | P = 0.364 |
| NCAM | 0.85 ± 0.17 | 0.65 ± 0.20 | 1.31 | P = 0.048 |
| calbindin | 0.89 ± 0.04 | 0.78 ± 0.05 | 1.14 | P < 0.001 |

To qualitatively confirm myelin differences seen in Western blots (shown in FIG. 3A), the lipid staining luxol fast blue (LFB) was performed in tissue from cortex, spinal cord (FIG. 3B) and cerebellum (FIG. 2C). Representative images show lower myelin levels in hypoxic vs normoxic animals in cortices, spinal cords and cerebella (black arrows). In addition, the external cerebellar granular cell layer (EGL) was substantially thicker in hypoxia cerebella compared to controls, suggesting a delayed cerebellar development in mice reared under hypoxia (yellow arrows).

Abbreviated Exposure to Hypoxia causes Reduced OPC Levels and Substantial Apoptosis.

Figure 4:
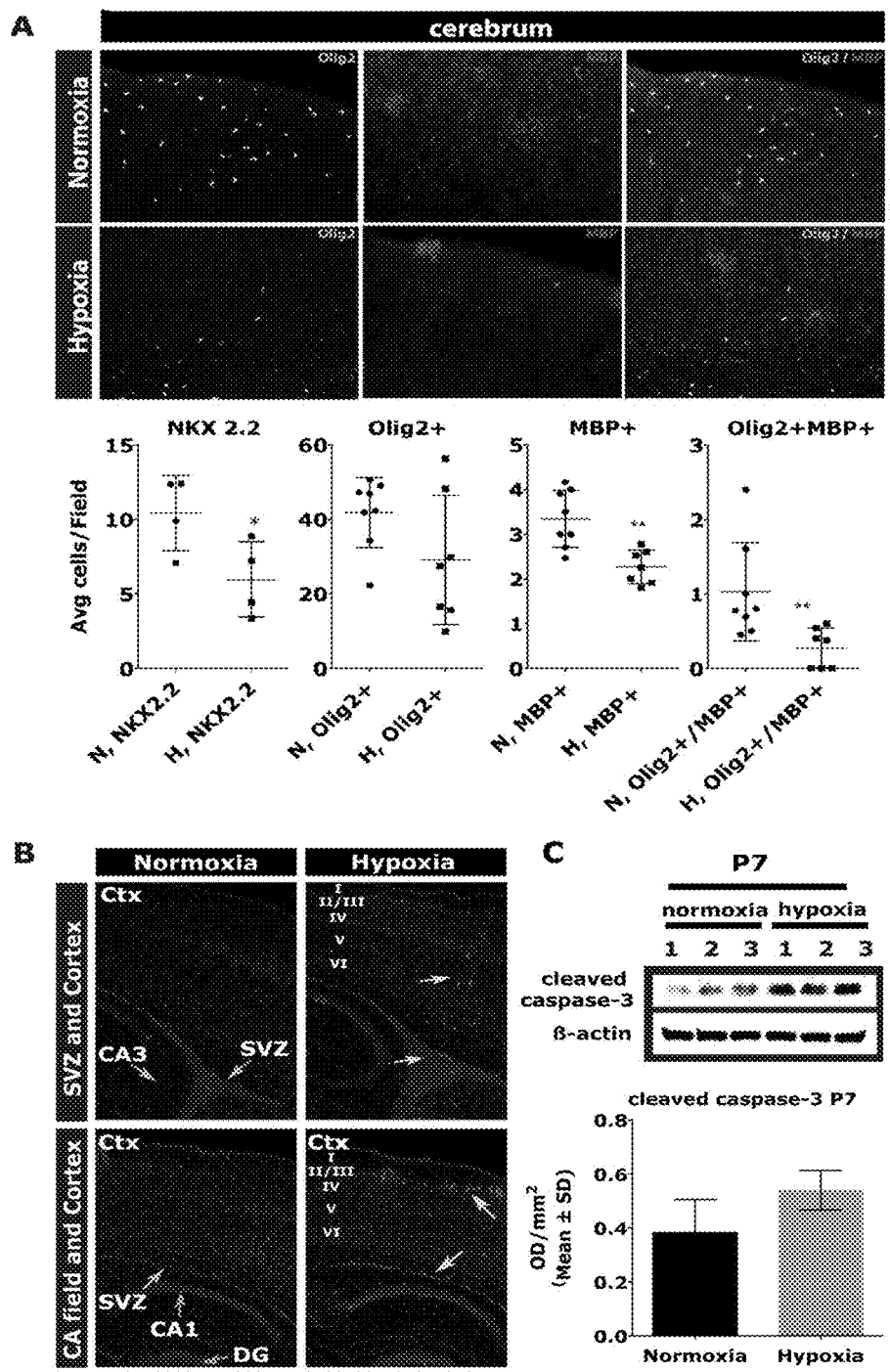
FIG. 4A-4C shows that abbreviated hypoxia (P3→P7) does not increase levels of OPCs but causes substantial apoptosis throughout cortical layers, hippocampus and SVZ. A: Immunohistochemistry and stereologic analysis of mouse cerebra at P13 using OL markers Olig-2 (OPCs, immature OLs, mature OLs), MBP (mature OLs) and NKX2.2 (OPCs). B: Immunohistochemical staining of level matched hypoxic and control cerebra at P7 showing anti-Cleaved Caspase 3 (CC3) (red) and nuclear marker DAPI (green arrows indicate specific regions SVZ, DG and CA1/3 field; yellow arrows mark levels of high apoptotic intensity in hypoxic mice). C: Representative Western blots using total brain homogenates from hypoxic and control CD1 mice at P7 using apoptosis marker CC3 and β-actin as a loading control. Densitometric analysis of Western blots from 3 independent experiments showing brain levels of CC3 at P7 in hypoxic and control mice with * equals $p<0.001$;  equals $p<0.01$; *equals $p<0.05$. SVZ, subventricular zone; DG, dentate gyrus; CA1-3, hippocampal CA fields; Ctx, cortex, I-VI=cortical layers 1-6. (n=6 hypoxic+6 normoxic animals for immunohistochemistry and Western blotting (each)).

An important question was whether CNS hypomyelination post hypoxia is caused by oligodendrocyte maturation arrest with increased levels of OPCs, or whether death of CNS cells including OL lineage cells is responsible for the effect seen. We first performed cell counts of Olig2(+) and MBP(+) cells of the OL-lineage at P13 in the rostral and caudal cerebrum including the extent of double-labeled Olig-2(+)/MBP(+) cells. Olig-2 is a marker for late OPCs, immature and mature OLs, while MBP specifically labels mature OLs only. MBP(+)/Olig2(+) double-labeled cells are therefore mature OLs. Whole brain quantitation of cell counts revealed reduced numbers of Olig-2(+) and MBP(+) cells in the hypoxic group. Differences were significant for mature MBP(+) cells. Similarly, levels of MBP(+)/Olig2(+) double-labeled cells (mature OLs) were significantly reduced in the hypoxic group throughout the entire cerebrum (FIG. 4A). Results indicated lower levels of mature MBP(+) OLs as suggested by Western blot analysis from whole brain at the same time point. It was unclear, however, whether reduced numbers of Olig-2(+) cells under hypoxia were based on mature OLs only or due to reductions in numbers of OPCs and immature OLs as well. We therefore performed cerebral cell counts using the OPC marker NKX2.2 showing significantly reduced levels of OPCs in the hypoxic group at P13 (FIG. 4A).

To further address this question we performed Western blots from the entire brain using different OPC markers Olig-1, Olig-2, PDGFαR and NG2 at P7, P13, P27 and P80. The late OPC marker NG2 and the OPC/immature/mature OL marker Olig-2 were significantly reduced at P7 (TABLE 5). Slight, albeit not significant, reductions in levels of OPC markers Olig-1 and PDGFRα at P7 were also noted. At postnatal day 13, OPC markers PDGFRα, Olig-1 and Olig-2 were reduced in cerebral tissue from hypoxic mice, but their levels all had normalized by P27 (TABLE 6 and TABLE 7). Levels of NG2 protein were similar in the exposure groups at P13 and P27 and were actually higher in the hypoxia group at P80 as were levels of Olig-1 at P80 (TABLE 8). In summary, cell counts and Western blot analysis showed no increase in numbers of OPCs/OPC markers, which might be expected in case of an OPC differentiation block. Instead, both sets of data indicated moderate reductions of OPCs/OPC markers.

We next assessed levels of apoptosis in the forebrain using the marker cleaved caspase-3 (CC3). Western blot analysis using whole brain lysates at P7 revealed increased levels of CC3 in the hypoxic group relative to control animals (FIG. 4C). To further characterize which brain regions were most impacted by the hypoxic insult we performed immunofluorescent staining with CC3. Morphological analysis directly after hypoxia at P7 revealed an increase in CC3(+) cells in many brain regions, most notably in cortical layers 2 and 5, the hippocampus and SVZ progenitor compartment. Differences in CC3 were not detected by Western blot analysis at later time points (P13 and P27) (FIG. 4B). These results demonstrate that abbreviated hypoxia affects levels of OPCs (FIG. 4A), immature OLs (FIG. 3A) and mature OLs (FIG. 3A, FIG. 4A). Reductions in OPC numbers and OPC markers for longer than 6 days post-injury do not support the hypothesis of an oligodendrocyte differentiation arrest in this model. Instead, we demonstrate substantial cell death post-injury throughout the entire brain and particularly present in cortical projection neurons of layers 2 and 5 and in the SVZ.

Abbreviated Hypoxia Induces Persistent Neuromotor Deficits in Mice.

Figure 5:
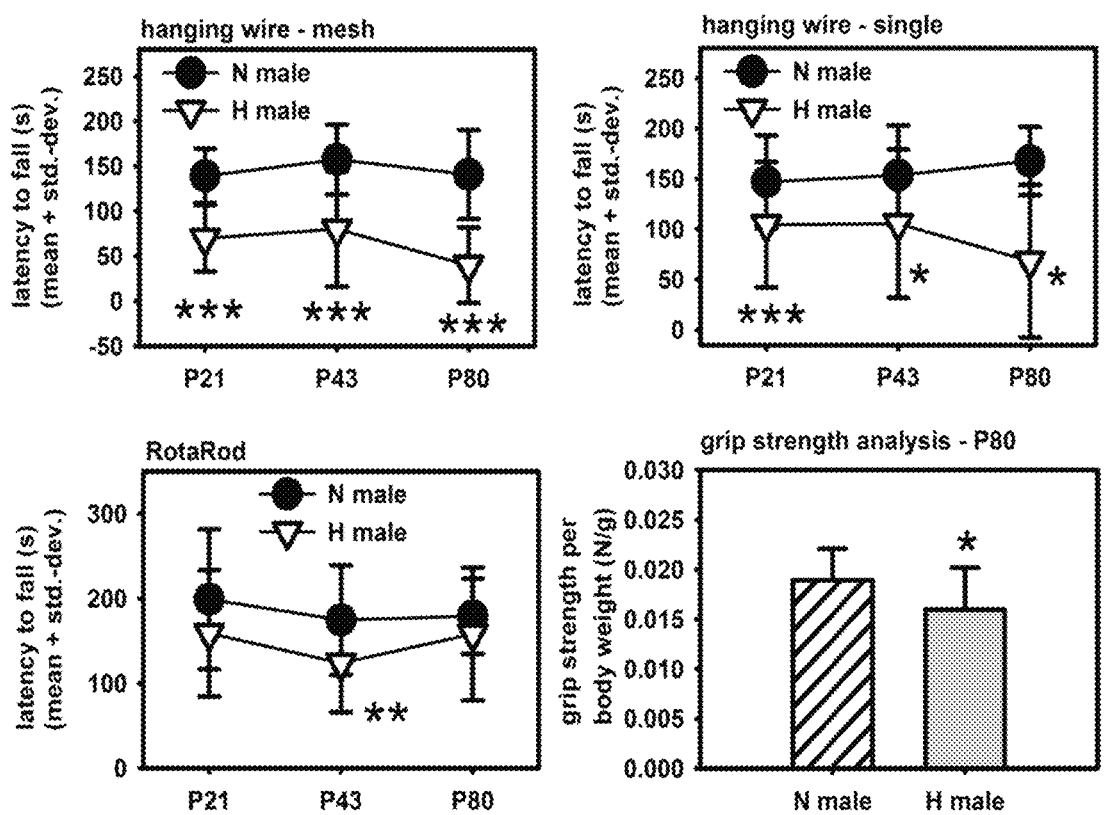
FIG. 5 depicts neuromotor capacity assessments of hypoxic and normoxic mice using the hanging wire—mesh and single wire—assessments, RotaRod testing, and grip strength analysis. Latency to fall or grip strength is graphed, with each time point representing >20 mice. Significant differences between hypoxic and normoxic are indicated by asterisks.

To assess neuromotor capacity and deficits in the hypoxic versus normoxic animals, motor phenotype analysis was performed at P21, P43 and P80 in male mice by using two different hanging wire tests (single wire+mesh wire), the RotaRod test and the grip strength meter test. The results are depicted in FIG. 5. In hanging wire tests assessing coordination, strength and endurance, male mice exposed to hypoxia displayed shorter grip latencies at P21, P43 and P80 (FIG. 5, TABLE 9). Hypoxic mice performed at lower levels in hanging wire tests, RotaRod test and in the grip strength meter test at all time points. Results from hanging wire tests indicated exacerbation of the disease course with age. All tests were performed >3 times per time point and mouse. Each test was performed with >20 mice per group for each time point. To assess forelimb grip strength we used the grip strength meter test. Grip strength was reduced by 16% in adult hypoxic mice at P90 (FIG. 5). Body weight and MRI-measured lean muscle mass were similar in the two experimental groups, indicating motor performance was not secondary to differences in body composition.

Specific results of behavioral motor testing using mesh wire, single wire and RotaRod at P21, P43 and P76 and grip strength at P90 are provided below in TABLE 9.

Mice exposed to brief hypoxia displayed shorter grip latencies at P21, P43 and P76. Similarly, brief hypoxia significantly reduced the latency to fall from the RotaRod at P43. In contrast to the behavioral outcome from both hanging wire tests at P76, no differences were detected between hypoxic and control animals in RotaRod performance at this time point. Last, forelimb strength was reduced by 16% in adult mice from the brief hypoxia group at P90 (TABLE 9) at which point body weights and MRI measured lean muscle mass were similar in the two experimental groups (data not shown).

Figure 6:
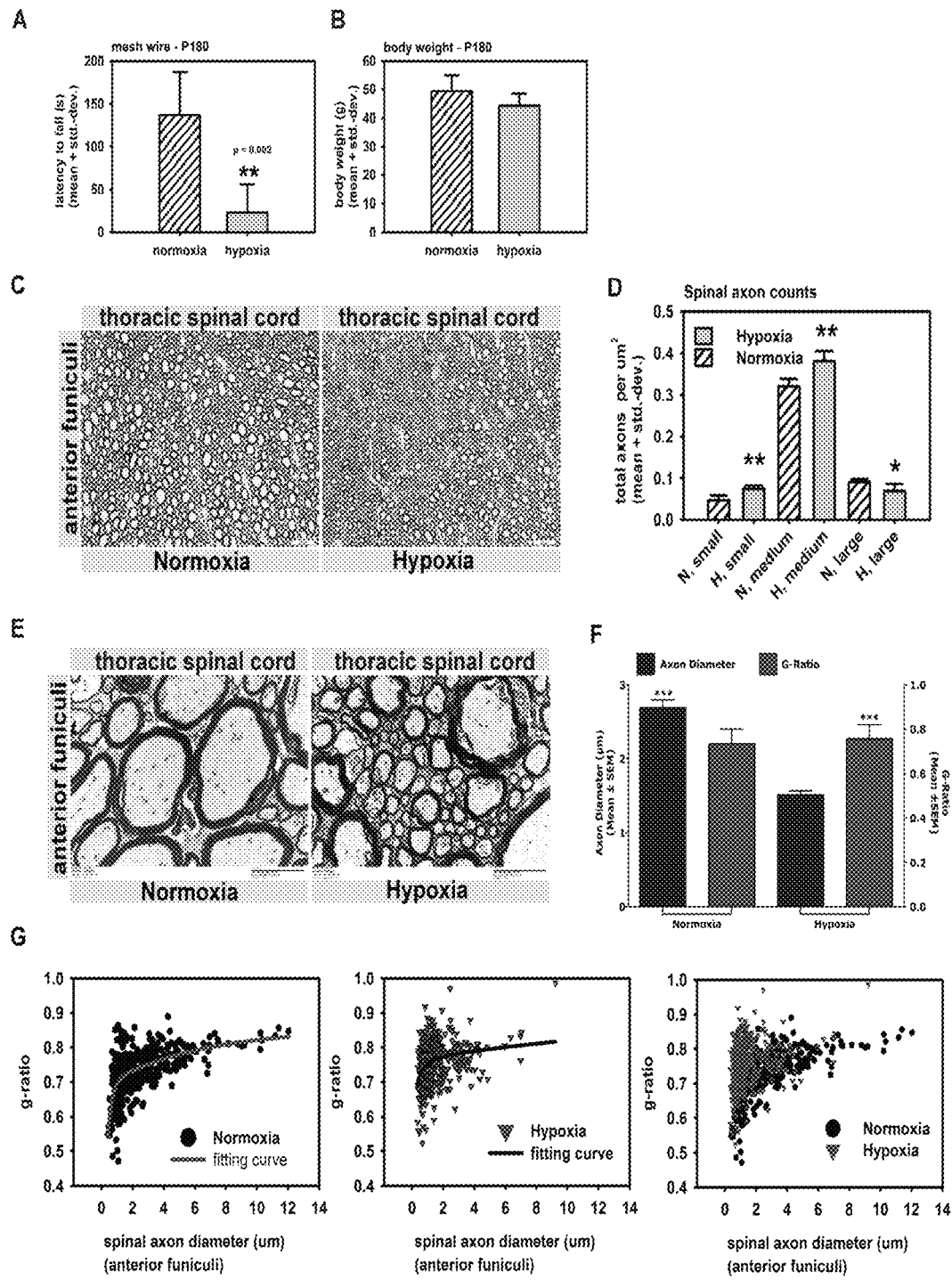
FIG. 6A-6G depicts abbreviated hypoxia changes axonal composition in spinal cords and causes dysmyelination of spinal axons. A, B: 6 month old hypoxic mice showed strong motor deficits in hanging wire tests (A) without having different body weights (B) (n=4 normoxic+6 hypoxic animals). C: Spinal cord thick sections from anterior and lateral funiculi (thoracic regions) in hypoxic and normoxic mice 6 month after the hypoxic insult (4 control+4 hypoxic mice). D: Automated axon counts of spinal cord thick sections from C. showing abnormal axonal compositions in spinal anterior funiculi with increased small and medium diameter axons and decreased numbers of large diameter axons relative to normoxic controls (small=1-4 μm; medium=4-10 μm; large=>10 μm) (4 control+4 hypoxic mice). E: Electron microscopy of spinal cord sections left and right of the anterior median fissure (thoracic spinal cord) in hypoxic and control animals (magnification: 8 kx). Higher g-ratios (thinner myelin sheaths) and loosely wrapped myelin around axons was prominent by Electron microscopy in thoracic spinal motor neurons (anterior funiculi) (4 control+4 hypoxic mice, 100 axons per animal). F. Chi-Square analysis of the g-ratio/axon diameter relationship in hypoxic and normoxic animals. G: Scatter plots of g-ratio vs. axon diameter in control (black) and hypoxic animals (red) with best fitting curves, with * equals $p<0.001$;  equals $p<0.01$; * equals $p<0.05$.

Beginning at P90, we monitored the global nocturnal activity of mice from each experimental group for six days. Mice in the brief hypoxia group displayed increased horizontal and vertical activity, as evidenced by more frequent horizontal (normoxia mean=9283; hypoxia mean=12,726; $p<0.004$) and vertical (normoxia mean=898; hypoxia mean=1,291; $p<0.001$) beam-breaks. To determine whether social interactions or intrinsic hyperactivity of hypoxic mice was responsible for this effect, testing was repeated with individual mice under otherwise identical conditions. Interestingly, the results of these experiments were even more pronounced than those described above (normoxia mean=342; hypoxia mean=642; $p<0.001$). Thus, along with their motor deficits, mice exposed to brief hypoxia display signs of abnormal hyperactivity as well.

ference) and imperfect myelin wrapping around axons was recently discovered in adult mice reared under hypoxia and served as an explanation for persistent neuro-motor deficits. To confirm this finding and further characterize the impact of hypoxia on spinal cord dysmyelination, we assessed "myelin quality" (g-ratios, axon diameters and proper myelin wrapping) in 6 month old hypoxic and normoxic CD1 mice. We first confirmed the severe motor phenotype in all hypoxic mice using hanging wire tests (FIG. 6A) with no significant differences in body weights between both groups (FIG. 6B). Thick sections of thoracic spinal cords from all animals were analyzed for overall spinal cord preservation of perfused animals without obvious squeeze artifacts. Surprisingly, the spinal axon composition in anterior funiculi containing motor and efferent pathways including the ves-

TABLE 9

BEHAVIORAL MOTOR TESTING

| Motor test | Normoxia, F | Normoxia, M | Hypoxia, F | Hypoxia, M | Statistical method |
|---|---|---|---|---|---|
| P21, mesh wire | 151.7 ± 39.6 (n = 28) | 139.1 ± 30.3 (n = 25) | 86.5 ± 49.5 (n = 29) ($p < 0.001$) | 69.8 ± 36.9 (n = 30) ($p < 0.001$) | Student's t-test (Normoxia, M vs Hypoxia, M); Mann-Whitney Rank Sum Test (Normoxia, F vs Hypoxia, F) |
| P21, single wire | 166.3 ± 26.4 (n = 22) | 147.0 ± 46.3 (n = 21) | 130.6 ± 55.6 (n = 27) ($p = 0.018$) | 104.4 ± 62.4 (n = 28) ($p = 0.011$) | Mann-Whitney Rank Sum Test (Normoxia, F vs Hypoxia, F; Normoxia, M vs Hypoxia, M) |
| P21, Rotarod | 254.5 ± 65.6 (n = 17) | 199.0 ± 82.7 (n = 20) | 169.8 ± 67.9 (n = 21) ($p < 0.001$) | 158.9 ± 74.6 (n = 26) ($p = 0.092$) | Student's t-test (Normoxia, F vs Hypoxia, F; Normoxia, M vs Hypoxia, M) |
| P43, mesh wire | 152.3 ± 51.2 (n = 24) | 157.4 ± 38.8 (n = 22) | 136.9 ± 61.6 (n = 25) ($P = 0.509$) | 80.1 ± 64.0 (n = 22) ($p < 0.001$) | Mann-Whitney Rank Sum Test (Normoxia, F vs Hypoxia, F; Normoxia, M vs Hypoxia, M) |
| P43, single wire | 151.5 ± 50.1 (n = 24) | 153.5 ± 49.7 (n = 22) | 99.8 ± 77.0 (n = 21) ($p < 0.015$) | 105.4 ± 73.8 (n = 22) ($p < 0.016$) | Mann-Whitney Rank Sum Test (Normoxia, F vs Hypoxia, F; Normoxia, M vs Hypoxia, M) |
| P43, Rotarod | 231.5 ± 57.8 (n = 15) | 174.5 ± 64.7 (n = 21) | 127.1 ± 61.5 (n = 23) ($p < 0.001$) | 123.8 ± 57.8 (n = 25) ($P = 0.008$) | Mann-Whitney Rank Sum Test (Normoxia, F vs Hypoxia, F); Student's t-test (Normoxia, M vs Hypoxia, M) |
| P76, mesh wire | 169.6 ± 36.0 (n = 20) | 140.7 ± 49.5 (n = 20) | 108.0 ± 68.1 (n = 14) ($P = 0.008$) | 39.8 ± 42.0 (n = 20) $P < 0.001$ | Mann-Whitney Rank Sum Test (Normoxia, F vs Hypoxia, F; Normoxia, M vs Hypoxia, M) |
| P76, single wire | 180.0 ± 0.0 (n = 20) | 167.7 ± 33.8 (n = 19) | 131.0 ± 71.5 (n = 14) ($p = 0.002$) | 68.2 ± 75.9 (n = 20) ($p < 0.001$) | Mann-Whitney Rank Sum Test (Normoxia, F vs Hypoxia, F; Normoxia, M vs Hypoxia, M) |
| P76, Rotarod | 190.5 ± 53.3 (n = 19) | 179.1 ± 44.5 (n = 17) | 207.0 ± 64.1 (n = 20) ($p = 0.389$) | 158.1 ± 78.4 (n = 25) ($p = 0.200$) | Mann-Whitney Rank Sum Test (Normoxia, F vs Hypoxia, F; Normoxia, M vs Hypoxia, M) |
| Grip strength meter test P90 | | 0.019 ± 0.003 (N/g), (n = 14) | | 0.016 ± 0.004 (N/g), (n = 27) ($p = 0.027$) | |

Abbreviated Exposure to Hypoxia causes Dysmyelination of Spinal Neurons and Changes to Axonal Composition in Spinal Cords CNS hypomyelination post hypoxia is a potential cause for neuro-motor deficits in nWMI and PVL models. However, while myelin levels catch up biochemically within weeks post injury, motor deficits persist in animals. Cerebral dysmyelination with thinner myelin sheaths or increased g-ratios (the ratio of axon circumference to myelin circumtibulospinal tract (stimulates axial extensor muscles), the anterior corticospinal tract (control of voluntary, skilled movements), and the tectospinal tract (mediates reflex movements in response to visual stimuli) was visibly different between both assignment groups.

Hypoxic animals showed lower numbers of large diameter axons (small diameter: 1-4 µM; medium diameter: 4-10 µM, large diameter: >10 µM) in anterior and lateral funiculi of the thoracic spinal cord (FIG. 6C). Automated (software-based) quantitation (60× images) from spinal anterior and lateral funiculi (throracic region) confirmed our qualitative assessment and demonstrated not only significantly fewer large diameter axons in hypoxic mice but at the same time more small and medium diameter axons compared to normoxic control mice born on the same day (FIG. 6D). Electron microscopy of 800 spinal axons (400 hypoxic, 400 normoxic, 100 axons per animal) left and right of the anterior median fissure from adult hypoxic and normoxic animals and subsequent data analysis (Sigma Plot) indicated a) absence of the Normality criterion for the data distribution (Shapiro-Wilk Test) and b) highly significant differences in the g-ratios as well as axon diameters between the hypoxic and normoxic group with $p<0.001$ (each) using the Mann-Whitney Rank Sum Test and the Kruskal-Wallis One Way Analysis of Variance on Ranks. A Contingency test (Chi-square, two-sided) analyzing the data distribution of g-ratio versus axon diameter in hypoxic and normoxic animals resulted in a highly significant difference between both datasets ($p<0.0001$, Odds ratio: 1.840) (FIGS. 6E and 6F). The axon diameters (median) were 2.12 μm in the normoxic group and 1.13 μm in the hypoxic group while g-ratios (median) were 0.742 for normoxic animals and 0.759 for hypoxic animals (FIG. 6F). Smaller g-ratios found in control animals are equivalent with thicker myelin sheaths compared to those in hypoxic mice. No significant difference was found in the number of whorls (collapsed, apoptotic axons), or axons with intensively stained mitochondria between both groups. The data shown in FIG. 6G suggested a non-linear relationship between g-ratio and axon diameter in small diameter axons and a rather linear relationship in large diameter axons. In an attempt to identify the best fit for the data distribution in both groups we used a non-linear equation (Sigma Plot) for the normoxic group: "Exponential Rise to Maximum, Double, 5 Parameter" with $f=y0+a\_(1-\exp(-b\_x))+c\_(1-\exp(-d\_x))$; $R=0.614$, $R2=0.377$; Standard Error of Estimate: 0.053. Logarithmic functions (3rd function) and Ligand binding functions (one and two site saturation) had a similar outcome with slightly reduced $R2$ values. Importantly, using the same functions for the data distribution in the hypoxic group resulted in a poor fit with $R2$ values of 0.1 or below (FIG. 6G), which indicated a different relationship between g-ratio and axon diameter in the spinal cord of hypoxic animals.

In summary, results indicate that hypoxia from P3 until P7 is sufficient to cause long-term myelination deficits in 6 month old mice. In addition, we demonstrate spinal white matter changes affecting tracts responsible for motor function. Both myelination deficits and axonal composition in the spinal cord strongly correlate with the persistent motor phenotype in adult animals.

Discussion

Neonatal white matter injury (nWMI), particularly PVL, underlies the neurodevelopmental delays often seen in children born at the extremes of prematurity. Diffuse hypomyelination, reduced cortical white matter and increased ventricle sizes are characteristic disease markers. In these patients, it is suspected that hypoxia and recurrent episodes of mild hypoxia-ischemia impair or delay OPC differentiation or may reduce OPC cell death, thereby reducing the pool of mature OLs capable of myelination. Rodent models exposing neonatal mice to a long-duration chronic hypoxia (for up to 11 days) beginning at P3 (Back et al., 2006; Fagel et al., 2009; Fagel et al., 2006; Li et al., 2009; Scafidi et al., 2014; Turner et al., 2003; Weiss et al., 2004) may inaccurately recapitulate the human disease from a neurodevelopmental perspective. Furthermore, such prolonged hypoxia impairs growth and survival in neonatal mice, confounding the ability to accurately interpret these models. In the present study, it is demonstrated that exposure to hypoxia during postnatal day 3 (P3) until P7, which corresponds to the developmental phase of the human brain between pre-term and term infancy (gestational weeks 32-36), is sufficient to induce CNS hypomyelination and lasting motor and neurobehavior disturbances in mice, without severely reducing corporal and cerebral growth or compromising survival.

Mice reared in brief hypoxia strongly down-regulated markers of mature OLs including MBP, PLP and MOG, as well as the immature OL marker CNPase. While the present findings cannot be directly equated with similar hypoxia models due to differences in exposure time and strain (Back et al., 2006; Jablonska et al., 2012; Scafidi et al., 2014; Turner et al., 2003), it is notable that the reduction in myelin protein expression and delay in myelination through P27 is comparable to or exceeds what has been reported previously (Back et al., 2006; Jablonska et al., 2012; Scafidi et al., 2014; Turner et al., 2003). This protein-level reduction in mature myelin occurred despite a normalization of myelin-associated gene transcripts by P27, suggesting that posttranscriptional regulation of gene expression or protein turn-over may influence the amount of myelin present in the affected CNS structures.

Recent studies have shown that exposure to a standard duration of hypoxia (P3-P11) induces the proliferation of OPCs and reduces the number of immature OLs undergoing apoptosis one week after the exposure (Jablonska et al., 2012; Scafidi et al., 2014). While we did find evidence of increased cerebral apoptosis at the end of hypoxic exposure (P7), we also found much lower levels of OPC markers at P7 and P13. Thus, the present abbreviated course of hypoxia may reduce the OPC pool and limit the number of cells that develop into mature, myelinating OLs. No matter the cellular mechanism, we have demonstrated that a brief period of hypoxia is sufficient to induce a degree of hypomyelination and a neurological phenotype comparable to those seen by others (Back et al., 2006; Jablonska et al., 2012; Li et al., 2009; Scafidi et al., 2014; Turner et al., 2003).

In the models of PVL, a prolonged period of hypoxia does not appear to induce CNS inflammation (Back et al., 2006; Jablonska et al., 2012). In the present model, however, evidence of microglial activation is shown three weeks after the hypoxic insult that persists into adulthood. This activation could reflect on-going cellular and axonal injury that contributes to the pathological and behavioral abnormalities in the hypoxia-exposed mice. However, a certain degree of inflammation is necessary to induce remyelination in patients with multiple sclerosis and in animal models of demyelinating disease (Arnett et al., 2001; Arnett et al., 2003; Bieber et al., 2003; Graca and Blakemore, 1986; Kotter et al., 2001; Kotter et al., 2005; Li et al., 2005; Ludwin, 1980; Mason et al., 2001; Njenga et al., 1999); perhaps the observed microglial activation is a beneficial response to hypoxic injury. The increased external cerebellar granular cell layer (EGL) thickness in hypoxic mice at P13 may indicate a delay in cerebellar development with changes in cellular behavior of neuronal progenitor cells. Alternatively, the increased EGL thickness may be the result of premature granule cell differentiation in response to hypoxia with remaining granule cell progenitors being eliminated around P21. Differences observed in the cerebellar EGL thickness became undetectable between hypoxic and normoxic animals at P27. Despite the general importance of the cerebellum for motor coordination, it remains undetermined whether a delay in cerebellar development between P13 and P27 is sufficient to explain aggravation of a persisting neuromotor phenotype between P43 and P80 in mice.

A persistent neurological phenotype has been described in C57BL/6 mice exposed to the longer, standard period of hypoxia (Scafidi et al., 2014; Weiss et al., 2004). However, it was previously unclear whether and, to what extent, outbred CD1 mice are susceptible to hypoxic stress (Li et al., 2009). The present data demonstrate that CD1 mice suffer from significant motor and behavioral abnormalities that persist well into adulthood after only brief exposure to hypoxia during the neonatal period. While a quantitative myelin "catch-up" was observed in hypoxia-exposed mice at P27 and P80, recent electron microscopic studies have demonstrated a qualitative difference in myelin adulthood (Jablonska et al., 2012; Scafidi et al., 2014), perhaps explaining the phenotype observed here.

In summary, a novel model of PVL is characterized in detail in which a brief course of hypoxia targeting the neonatal brain of outbred CD1 mice induces hypomyelination and a persisting motor phenotype throughout adulthood. The added benefits of this PVL model include decreased neonatal death, diminished weight loss, and elimination of cross-fostering. Importantly, the use of CD1 mice affords large litter sizes (relative to C57BL/6 mice) and reduced research costs due to lack of co- or cross-fostering, which enables large-scale, preclinical screening, development, and testing of therapeutic compounds. This brief hypoxia animal model may be appropriate for future in vivo studies of PVL, especially those focusing on therapeutic interventions.

REFERENCES

Arnett, H. A., et al., 2001. TNF alpha promotes proliferation of oligodendrocyte progenitors and remyelination. Nat Neurosci. 4, 1116-22.

Arnett, H. A., et al., 2003. Functional genomic analysis of remyelination reveals importance of inflammation in oligodendrocyte regeneration. J Neurosci. 23, 9824-32.

Back, S. A., et al., 2006. Protective effects of caffeine on chronic hypoxia-induced perinatal white matter injury. Annals of Neurology. 60, 696-705.

Back, S. A., et al., 2002. Selective vulnerability of late oligodendrocyte progenitors to hypoxia-ischemia. The Journal of Neuroscience. 22, 455-63.

Back, S. A., et al., 2001. Late oligodendrocyte progenitors coincide with the developmental window of vulnerability for human perinatal white matter injury. The Journal of Neuroscience. 21, 1302-12.

Back, S. A., et al., 2005. Selective vulnerability of preterm white matter to oxidative damage defined by F2-isoprostanes. Annals of Neurology. 58, 108-20.

Barkovich, A. J. et al. 1999. Proton MR spectroscopy for the evaluation of brain injury in asphyxiated, term neonates. Am J Neuroradiol. 20, 1399-1405.

Barkovich, A. J., et al., 2006. MR imaging, MR spectroscopy, and diffusion tensor imaging of sequential studies in neonates with encephalopathy. Am J Neuroradiol. 27, 533-47.

Bieber, A. J., et al., 2003. Efficient central nervous system remyelination requires T cells. Ann Neurol. 53, 680-4.

Billiards, S. S., et al., 2008. Myelin abnormalities without oligodendrocyte loss in periventricular leukomalacia. Brain pathology. 18, 153-63.

Buitrago, M. M., et al., 2004. Short and long-term motor skill learning in an accelerated rotarod training paradigm. Neurobiology of learning and memory. 81, 211-6.

Buser, J. R., et al., 2012. Arrested preoligodendrocyte maturation contributes to myelination failure in premature infants. Annals of neurology. 71, 93-109.

Chahboune, H., et al., 2009. Hypoxic injury during neonatal development in murine brain: correlation between in vivo DTI findings and behavioral assessment. Cerebral cortex. 19, 2891-901.

Craig, A., et al., 2003. Quantitative analysis of perinatal rodent oligodendrocyte lineage progression and its correlation with human. Experimental neurology. 181, 231-40.

Dean, J. M., et al., 2011. Strain-specific differences in perinatal rodent oligodendrocyte lineage progression and its correlation with human. Developmental neuroscience. 33, 251-60.

Denic, A., et al., 2011. A single dose of neuron-binding human monoclonal antibody improves spontaneous activity in a murine model of demyelination. PloS One. 6, e26001.

Dobbing, J., Sands, J., 1979. Comparative aspects of the brain growth spurt. Early human development. 3, 79-83.

Douglas, R. M., et al., 2007. Chronic intermittent but not constant hypoxia decreases NAA/Cr ratios in neonatal mouse hippocampus and thalamus. American journal of physiology. Regulatory, integrative and comparative physiology. 292, R1254-9.

Fagel, D. M., et al., 2009. Fgfr1 is required for cortical regeneration and repair after perinatal hypoxia. The Journal of neuroscience: the official journal of the Society for Neuroscience. 29, 1202-11.

Fagel, D. M., et al., 2006. Cortical neurogenesis enhanced by chronic perinatal hypoxia. Experimental neurology. 199, 77-91.

Ferriero, D. M., 2004. Neonatal brain injury. The New England Journal of Medicine. 351, 1985-95.

Folkerth, R. D., 2005. Neuropathologic Substrate of Cerebral Palsy. J Child Neurol 20, 940-49.

Ganat, Y., et al., 2002. Chronic hypoxia up-regulates fibroblast growth factor ligands in the perinatal brain and induces fibroblast growth factor-responsive radial glial cells in the sub-ependymal zone. Neuroscience. 112, 977-91.

Gluckman, P. D., et al., 2005. Selective head cooling with mild systemic hypothermia after neonatal encephalopathy: multicentre randomized trial. The Lancet. 365,663-70.

Graca, D. L., Blakemore, W. F., 1986. Delayed remyelination in rat spinal cord following ethidium bromide injection. Neuropathol Appl Neurobiol. 12, 593-605.

Hack, M., et al., 2005. Chronic conditions, functional limitations, and special health care needs of school-aged children born with extremely low-birth-weight in the 1990s.

JAMA: the journal of the American Medical Association. 294, 318-25.

Hagberg, H., et al., 2002. Animal models of developmental brain injury: relevance to human disease. A summary of the panel discussion from the Third Hershey Conference on Developmental Cerebral Blood Flow and Metabolism. Developmental neuroscience. 24, 364-6.

Jablonska, B., et al., 2012. Oligodendrocyte regeneration after neonatal hypoxia requires FoxO1-mediated p27Kip1 expression. The Journal of neuroscience: the official journal of the Society for Neuroscience. 32, 14775-93.

Jones, B. J., Roberts, D. J., 1968a. The quantiative measurement of motor inco-ordination in naive mice using an acelerating rotarod. The Journal of pharmacy and pharmacology. 20, 302-4.

Jones, B. J., Roberts, D. J., 1968b. A rotarod suitable for quantitative measurements of motor incoordination in naive mice. Naunyn-Schmiedebergs Archiv fur experimentelle Pathologie and Pharmakologie. 259, 211.

Kanaan, A., et al., 2006. Effect of chronic continuous or intermittent hypoxia and reoxygenation on cerebral capillary density and myelination. American journal of physiology. Regulatory, integrative and comparative physiology. 290, R1105-14.

Kinney, H. C., et al., 2005. Hypoxic-ischemic brain injury in infants with congenital heart disease dying after cardiac surgery. Acta Neuropathol 110, 563-78.

Kotter, M. R., et al., 2001. Macrophage depletion impairs oligodendrocyte remyelination following lysolecithin-induced demyelination. Glia. 35, 204-12.

Kotter, M. R., et al., 2005. Macrophage-depletion induced impairment of experimental CNS remyelination is associated with a reduced oligodendrocyte progenitor cell response and altered growth factor expression. Neurobiol Dis. 18, 166-75.

Kovner, I., et al., 2010. Calibration and validation of EchoMRI whole body composition analysis based on chemical analysis of piglets, in comparison with the same for DXA. International journal of body composition research. 8, 17-29.

Lalonde, R., et al., 2003. Motor coordination in mice with hotfoot, Lurcher, and double mutations of the Grid2 gene encoding the delta-2 excitatory amino acid receptor. Physiology & behavior. 80, 333-9.

Lan, W. C., et al., 2011. Sex-specific cognitive deficits and regional brain volume loss in mice exposed to chronic, sublethal hypoxia. Pediatric research. 70, 15-20.

Li, Q., et al., 2009. Strain differences in behavioral and cellular responses to perinatal hypoxia and relationships to neural stem cell survival and self-renewal: Modeling the neurovascular niche. The American journal of pathology. 175, 2133-46.

Li, W. W., et al., 2005. Minocycline-mediated inhibition of microglia activation impairs oligodendrocyte progenitor cell responses and remyelination in a non-immune model of demyelination. J Neuroimmunol. 158, 58-66.

Liu, Y, et al., 2002. Hypoxic-ischemic oligodendroglial injury in neonatal rat brain. Pediatric Res. 51, 25-33.

Lodygensky, G. A., et al., 2010. Neuroimaging of cortical development and brain connectivity in human newborns and animal models. Journal of anatomy. 217, 418-28.

Ludwin, S. K., 1980. Chronic demyelination inhibits remyelination in the central nervous system. An analysis of contributing factors. Lab Invest. 43, 382-7.

Mason, J. L., et al., 2001. Interleukin-lbeta promotes repair of the CNS. J Neurosci. 21, 7046-52.

Maurissen, J. P., et al., 2003. Factors affecting grip strength testing. Neurotoxicology and teratology. 25, 543-53.

Ment, L. R., et al., 1998. Association of chronic sublethal hypoxia with ventriculomegaly in the developing rat brain. Brain research. Developmental brain research. 111, 197-203.

Meyer, O. A., et al., 1979. A method for the routine assessment of fore- and hindlimb grip strength of rats and mice. Neurobehavioral toxicology. 1, 233-6.

Miller, S. P. et al., 2002. Predictors of 30-month outcome after perinatal depression: Role of proton MRS and socio-economic factors. Pediatr Res. 52, 71-77.

Miller, S. P. et al., 2005. Patterns of brain injury in term neonatal encephalopathy. J Pediatrics. 146, 453-60.

Miller, S. P., et al., 2007. Abnormal brain development in newborns with congenital heart disease. N Eng J Med. 357:1928-38.

Morita, S., et al., 2014. Changes in pericytic expression of NG2 and PDGFRB and vascular permeability in the sensory circumventricular organs of adult mouse by osmotic stimulation. Cell biochemistry and function. 32, 51-61.

Ness, J. K., et al., 2001. Perinatal hypoxia-ischemia induces apoptotic and excitotoxic death of periventricular white matter oligodendrocyte progenitors. Developmental neuroscience. 23, 203-8.

Njenga, M. K., et al., 1999. Absence of spontaneous central nervous system remyelination in class II-deficient mice infected with Theiler's virus. J Neuropathol Exp Neurol. 58, 78-91.

Radom-Aizik, S., et al., 2013. Growth inhibition and compensation in response to neonatal hypoxia in rats. Pediatric research. 74, 111-20.

Rezaie, P., Dean, A., 2002. Periventricular leukomalacia, inflammation and white matter lesions within the developing nervous system. Neuropathology : official journal of the Japanese Society of Neuropathology. 22, 106-32.

Riddle, A., et al., 2006. Spatial heterogeneity in oligodendrocyte lineage maturation and not cerebral blood flow predicts fetal ovine periventricular white matter injury. The Journal of neuroscience : the official journal of the Society for Neuroscience. 26, 3045-55.

Romijn, H. J., et al., 1991. At what age is the developing cerebral cortex of the rat comparable to that of the full-term newborn human baby? Early human development. 26, 61-7.

Scafidi, J., et al., 2014. Intranasal epidermal growth factor treatment rescues neonatal brain injury. Nature. 506, 230-4.

Schmittgen, T. D., Livak, K. J., 2008. Analyzing real-time PCR data by the comparative C(T) method. Nature protocols. 3, 1101-8.

Semple, B. D., et al., 2013. Brain development in rodents and humans: Identifying benchmarks of maturation and vulnerability to injury across species. Progress I neurobiology. 106-107, 1-16.

Shankaran, S., et al., 2005. Whole-body hypothermia for neonates with hypoxic-ischemic encephalopathy. N Eng J Med. 353, 1574-84.

Shinzawa, K., et al., 2008. Neuroaxonal dystrophy caused by group VIA phospholipase A2 deficiency in mice: a model of human neurodegenerative disease. The Journal of neuroscience: the official journal of the Society for Neuroscience. 28, 2212-20.

Silbereis, J. C., et al., 2010. Towards improved animal models of neonatal white matter injury associated with cerebral palsy. Disease models & mechanisms. 3, 678-88.

Skoff, R. P., et al., 2001. Hypoxic-ischemic injury results in acute disruption of myelin gene expression and death of oligodendroglial precursors in neonatal mice. Int J Devl Neuroscience. 19, 197-208.

Steinman, K. J., et al., 2009. Neonatal watershed brain injury on MRI correlates with verbal IQ at four years. Pediatrics. 123(3), 1025-30.

Turner, C. P., et al., 2003. A1 adenosine receptors mediate hypoxia-induced ventriculomegaly. Proceedings of the National Academy of Sciences of the United States of America. 100, 11718-22.

Vetrone, S. A., et al., 2009. Osteopontin promotes fibrosis in dystrophic mouse muscle by modulating immune cell subsets and intramuscular TGF-beta. The Journal of clinical investigation. 119, 1583-94.

Volpe, J. J., 2001. Neurobiology of periventricular leukomalacia in the premature infant. Pediatric research. 50, 553-62.

Volpe, J. J., 2001a. Neurology of the Newborn, 4$^{th}$ ed, WB Saunder Company, Philadelphia.

Volpe, J. J., 2003. White matter injury of the premature infant—More common than you think. Pediatrics. 112, 176-180.

Volpe, J. J., 2008. Neurology of the newborn/Joseph J. Volpe. Saunders/Elsevier, c2008., Philadelphia Watzlawik, J. O., et al., 2013. PDGF is required for remyelination-promoting IgM stimulation of oligodendrocyte progenitor cell proliferation. PloS one. 8, e55149.

Weiss, J., et al., 2004. Neonatal hypoxia suppresses oligodendrocyte Nogo-A and increases axonal sprouting in a rodent model for human prematurity. Experimental Neurology. 189, 141-9.

Welin, A. K., et al., 2005. White matter injury following prolonged free radical formation in the 0.65 gestation fetal sheep brain. Pediatric Research. 58, 100-5.

Wohl, S. G., et al., 2011. In situ dividing and phagocytosing retinal microglia express nestin, vimentin, and NG2 in vivo. PloS One. 6, e22408.

Woodward, L. J., et al., 2006. Neonatal MRI to predict neurodevelopmental outcomes in preterm infants. The New England Journal of Medicine. 355, 685-94.

Zhou, D., et al., 2008. Gene expression in mouse brain following chronic hypoxia: role of sarcospan in glial cell death. Physiological Genomics. 32, 370-9.

Zhu, L., et al., 2012. Microglia/monocytes with NG2 expression have no phagocytic function in the cortex after LPS focal injection into the rat brain. Glia. 60, 1417-26.

EXAMPLE 2

Antibody Treatment of Hypoxia-Mediated PVL

The rate of cerebral palsy (CP) has increased steadily over the past few decades to its current incidence of more than 3 per 1000 live births, with 800000 Americans affected as of 2009. Much of this increase is due to the improving rate of survival of premature neonates born prematurely and at very low birth weight. Over the course of infancy and childhood, these former preemies often display motor deficits and cognitive-behavioral disturbances that correlate closely with the neuropathology of modern-day periventricular leukomalacia (PVL). White matter disease predominates in PVL and is manifest as diffuse hypomyelination and reduced white matter volume. These abnormalities appear to result from the selective death or disordered development of the preoligodendrocyte (pre-OL) during episodes of hypoxia-ischemia (H-I) (18). Because most OL progenitors are predisposed to hypoxia-ischemia (H-I) injury due to their predominantly periventricular location, pre-OLs lost to H-I may not be repopulated to an extent sufficient to permit normal cerebral myelination.

At present there are no therapies available to prevent or cure white matter disease or injury in neonates or infants, particularly including PVL. Antibodies that promote remyelination and CNS regeneration in animal models of MS and ALS (6-14, 19) have been identified and cloned. The human antibody HIgM22 currently in clinical trials for MS patients targets cells of the OL-lineage and stimulates OPC proliferation, rescues OPCs from undergoing cell death and thus promotes remyelination (7, 20, 21). A second human antibody, HIgM12, targets OPCs and CNS neurons as well as their progenitors. HIgM12 stimulates neurite outgrowth in vitro and improves function in models of MS (22, 23). Human and mouse antibodies HIgM22 and SCH94.03 deliver to the CNS with i.p. administration, crossing the blood brain barrier, where they target demyelinated lesions in adult mice (15, 16).

The molecular and cellular effects of a potentially therapeutic antibody already in clinical trials for MS (HIgM22) as well as an antibody that shows promise in animal models of MS and ALS (HIgM12) were evaluated for the treatment or alleviation of white matter disease or injury in neonates and infants, particularly PVL, particularly including hypoxia-ischemia induced PVL. HIgM22 is a human antibody that stimulates remyelination most likely through stimulation of OPC proliferation and possibly rescue of OPCs. The data shown here are the first in vivo data using antibodies suggesting stimulation of OPC proliferation and maturation in antibody-stimulated rescue of the neuropathology underlying neonatal white matter disease or injury, particularly PVL. Potential cellular targets of both HIgM22 and HIgM12 antibodies—OL progenitors, neuronal progenitors and possibly neural stem cells—are abundantly present in neonatal mice during their first two weeks postnatal, which may amplify the beneficial effects of both antibodies seen in adult mice with little progenitor pools. Based on key developmental processes and growth trajectories in humans and rodents the gestational weeks 23-40 in the human situation correspond to postnatal days 1-10 (P1-10) in rodents (Dobbing, J., Sands, J., 1979. Comparative aspects of brain growth spurt. Early Human Development 311, 79-83; Bockhorst, K. H., Narayana, P. A., Liu, R., Ahobila-Vijjula, P., Ramu, J., et al., 2008. Early postnatal development of rat brain: in vivo diffusion tensor imaging. Journal of Neuroscience Research 86, 1520-1528; for review see: Semple, Blomgren, Gimlin, Ferriero, Noble-Haeusslein. 2013. Brain development in rodents and humans: Identifying benchmarks of maturation and vulnerability to injury across species. Progress in Neurobiology 106-107. 1-16). The time of treatment in rodents (P7) in the studies provided herein therefore corresponds to a term human neonate (P36). The peak in gliogenesis including OL progenitors occurs between P7-10 in rodents and gestational weeks 36-40 in human neonates (Catalani, A., Sabbatini, M., Consoli, C., Cinque, C., Tomassoni, D., et al., 2002. Glial fibrillary acidic protein immunoreactive astrocytes in developing rat hippocampus. Mechanics of Ageing & Development 123, 481-490; Kriegstein, A., Alvarez-Buylla, A., 2009. The glial nature of embryonic and adult neural stem cells. Annual Review of Neuroscience 32, 149-184). Based on rodent data shown here and brain growth comparisons between the rodent versus human brain, comparable administration of the HIgM antibodies can be performed between gestational weeks 36-40 in human neonates.

Periventricular leukomalacia (PVL) is a principal cause of cerebral palsy in survivors of preterm birth (1, 2). White matter disease predominates in PVL and is manifest as diffuse hypomyelination and reduced white matter volume in the cerebral cortex (3). At a cellular level, PVL is characterized by death and disordered maturation of glial cells. Neural stem cells (NSCs) and neural progenitor cells (NPCs, such as neuroblasts and OPCs) may be capable of promoting the recovery of the cerebral white matter in each of these conditions, a process that may be facilitated by treatment with regenerative and remyelination-promoting antibodies.

It was evaluated whether the treatment of hypoxia-exposed mice with HIgM22 or HIgM12 improves cerebral development and neuromotor function. The data presented herein demonstrates that treating mice with either or both HIgM22 and HIgM12 human antibodies intraperitoneally (i.p) as a single dose almost completely rescues the severe PVL-like motor phenotype in mice. Cerebral tissue analysis from hypoxic and control mice shows antibody-mediated effects on neuronal progenitor cells and OPCs which may explain the rescued phenotype and further underlines the impact of early glial and possibly neuronal progenitor cells in this study. The treatment of hypoxia-exposed mice in an animal model of PVL with antibody HIgM22 or HIgM12, or with both HIgM22 and HIgM12 antibodies, improves cerebral development and neuromotor function.

Using the new short hypoxia mouse model of Periventricular Leukomalacia (PVL) (Example 1) that induces hypomyelination and persistent motor deficits in male neonatal mice, antibodies were evaluated in the PVL model.

General procedure: Timed pregnant CD1 mice are obtained from Charles River laboratories with an average litter size of 12-15 pups. Litters are culled down to 12 neonatal mice within the first 24 hrs after birth. Neonatal CD1 mice plus dam are reared under hypoxia for 96 h from postnatal day 3 (P3) until P7 under constant chronic hypoxia (10±0.5% O2). Proper functioning of the oxygen sensor is determined before each run and oxygen levels are checked every other hour for the first 12 hrs and twice daily every consecutive day. Age matched control mice are housed under identical conditions under room air (21% O2). At P7 mice are removed from the hypoxic chamber, injected i.p. with PBS or antibodies and housed under normal, normoxic conditions. Normoxic control animals receive PBS i.p. All neonatal mice receive ear punches at P7 directly before the antibody/PBS injection (left ear=antibody x; right ear=antibody y). Half the litter antibodies from the category one and the other half will receive antibodies from category two. Category one antibodies are HIgM12 or HIgM22 and category 2 antibodies are control antibodies HIgM116 or HIgM126. All antibodies are administered in a blinded manner with mice randomly assigned to antibody category one or two. Female mice are sacrificed at weaning age P21 and male mice assigned to groups of 3 or 4 per cage depending on the number of male mice per litter.

Myelin quantity is determined at P13 by Western blotting. The motor outcome is tested at P21, P43 and P80 using hanging wire tests (mesh wire and single wire), Rotarod testing and grip strength, using standard methodology used in our laboratory. All studies were performed in a blinded manner.

The data provided herein using human monoclonal antibodies HIgM12 or HIgM22 for the treatment of hypoxia-mediated PVL in mice show rescue of the PVL-like motor phenotype throughout mouse adulthood with both human antibodies compared to human control antibody HIgM126. Antibodies were administered i.p. in a single dose at P7 directly after the hypoxic insult. The data further indicates molecular changes in levels of CNS proteins with HIgM12 and HIgM22 compared to isotype control treated animals. We conclude that both HIgM12 and HIgM22 rescue the motor phenotype in our animal model of PVL including into mouse adulthood (P80). Antibody HIgM22 increased levels of cerebral myelin proteins and oligodendrocyte progenitor cell (OPC) markers compared to control antibody HIgM126 at P13.

Figure 7:
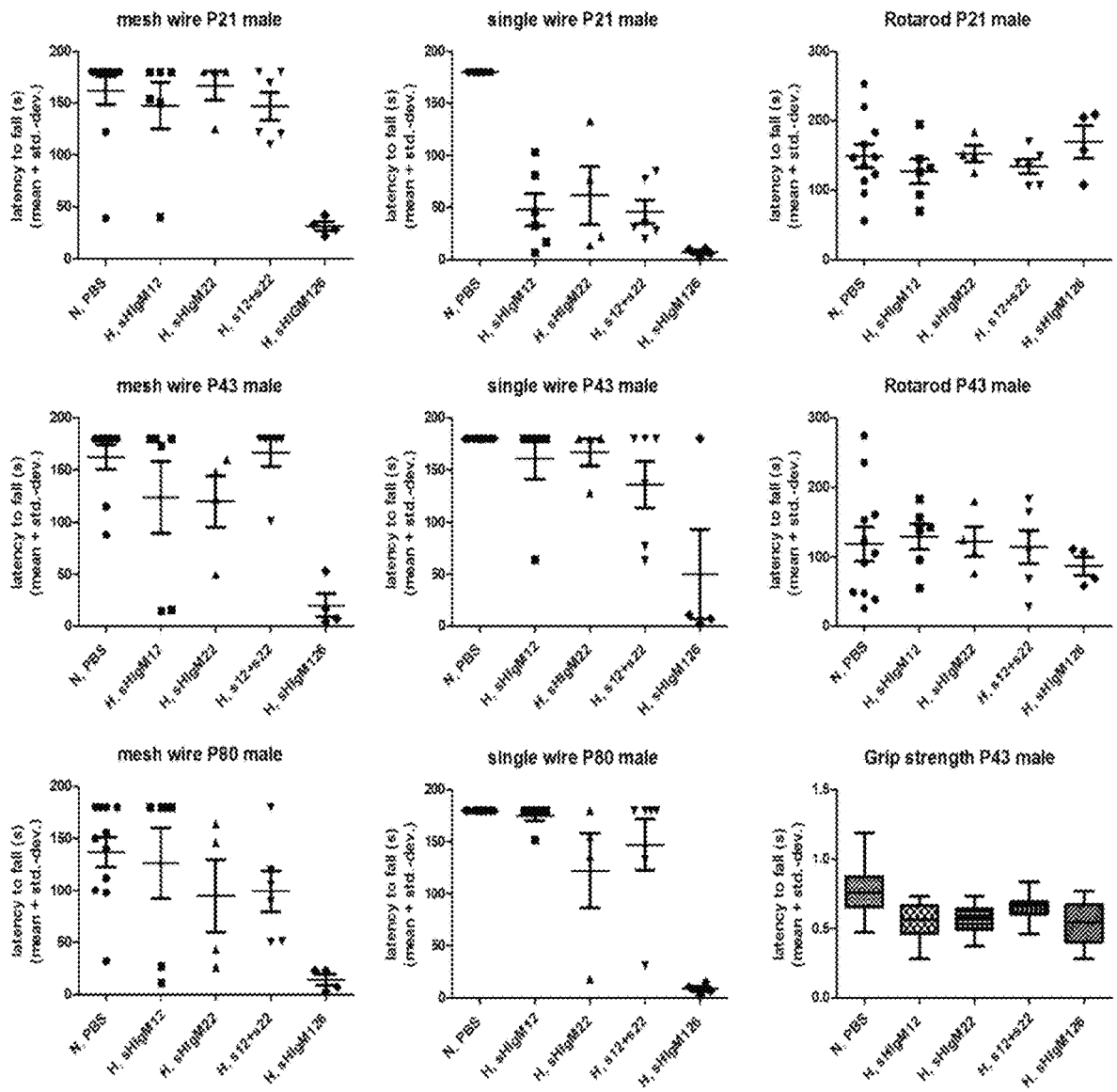
FIG. 7 presents neuromotor capacity testing of hypoxia PVL model animals treated with antibodies versus normoxic animals treated with PBS (N,PBS). Hypoxic animals are indicated by H, followed by the antibody administered. At P7, mice were treated with a single dose of either PBS (normoxia), human antibody HIgM12, HIgM22, a combination of antibodies HIgM22+HIgM12, or isotype control antibody HIgM126 in the hypoxic groups (30 μg each antibody per mouse/60 μg per animal for the combined treatment 12+22). Behavioral assessment was performed at P21, P43 and P80 using hanging wire tests (mesh+single wire), the rotarod test and the grip strength meter test (P43).

Human antibodies HIgM12 and HIgM22 rescue male mice from the PVL-like phenotype. Mice were reared under hypoxia from P3→P7 or normoxia and subsequently under room air. At P7 mice were treated with a single dose of either PBS (normoxia) human antibody HIgM12, HIgM22, a combination of antibodies HIgM22+HIgM12, or isotype control antibody HIgM126 in the hypoxic groups (30 μg each antibody per mouse/60 μg per animal for the combined treatment 12+22). Behavioral assessment was performed at P21, P43 and P80 using hanging wire tests (mesh+single wire), the rotarod test and the grip strength meter test (P43). The results are graphed in FIG. 7.

All hypoxic groups treated with HIgM12, HIgM22 or combined HIgM12+HIgM22 performed at a higher level in both hanging wire tests compared to control antibody HIgM126-treated hypoxic animals at all time points. This was statistically significant with the exception of the single wire test at P21. Differences in latencies to fall for the single wire test increased with age between P21 and P43 in hypoxic animals treated with HIgM12, HIgM22, combined treatment compared to control antibody HIgM126 treated animals. Hypoxic animals treated with control antibody HIgM126 did not improve in levels of performance with age. The rotarod test showed no significant differences at both time points (P21 and P43) between hypoxic animals treated with HIgM12, HIgM22 or combined treatment compared to control antibody treated animals. The grip strength meter test indicated a significant difference between normoxic and all hypoxic animals as well as between hypoxic animals treated with HIgM12 combined with HIgM22 compared to HIgM126-treated animals.

HIgM12 and HIgM22 change expression levels of CNS progenitor markers and myelin markers in hypoxic cerebra. Mice reared under hypoxia (P3→P7) or room air were treated at P7 with PBS (normoxia), HIgM22 (hypoxia), HIgM12 (hypoxia) or isotype control antibody sHIgM126 (IC) (hypoxia) and reared for 6 additional days under room air. Neonatal animals received a single dose of 30 μg of antibody (HIgM12, HIgM22, HIgM126) in 50 μl of PBS i.p. at P7 after the hypoxic injury (10 μg antibody/gram body weight). Normoxic animals received an equal volume of PBS i.p. at P7.

At P13, mice were sacrificed and cerebra from all groups analyzed by Western blotting using antibodies against various CNS proteins. The results are presented in FIG. 8, with each lane representing an individual animal. Protein levels were evaluated for each of CNPase, myelin basic protein (MBP), Olig-1, PDGFαR, NG2, Fyn, Lyn, GFAP, β3tubulin, double cortin (DC), Nestin and β-actin (protein control) Protein lysates from 1.5 mg cerebral tissue was loaded per lane in 4-20% polyacrylamide gradient gels. Proteins were transferred to PVDF membrane (Millipore, Immobilon-P, #IPVH00010), blocked with 10% instant nonfat dry milk powder in PBS-T, washed extensively with PBS-T and probed with antibodies targeting CNPase, myelin basic protein (MBP), Olig-1, PDGFαR, NG2, Fyn, Lyn, GFAP, β3tubulin, double cortin (DC), Nestin and β-actin (protein control) in 5% bovine serum albumin (BSA) (Sigma, A9647) in PBS-T. Antibodies were purchased from Millipore (MBP, rabbit polyclonal, AB980; NG2, rabbit polyclonal, AB5320), Chemicon (Olig-1, rabbit polyclonal, AB15620), Abcam (GFAP, rabbit polyclonal, Ab7779; Nestin, rabbit monoclonal, Ab105389), Sigma (CNPase, mouse monoclonal, C5922), Santa Cruz (Lyn, mouse monoclonal, sc-7274; PDGFαR, rabbit polyclonal, sc-338), Cell Signaling (doublecortin (DC), rabbit polyclonal, #4604; β3tubulin, rabbit polyclonal, #5568; Fyn, rabbit polyclonal, #4023; β-actin, rabbit polyclonal, #4967). Mini-Protean TGX polyacrylamide gels (#456-1094), XT Sample buffer (#161-

0791), β-mercaptoethanol (#161-0710), sodium dodecyl sulfate (SDS) (#161-0302), TRIS (#161-0719) were purchased from Biorad. Glycine (BP381-5) was purchased from Fisher Scientific.

Figure 8:
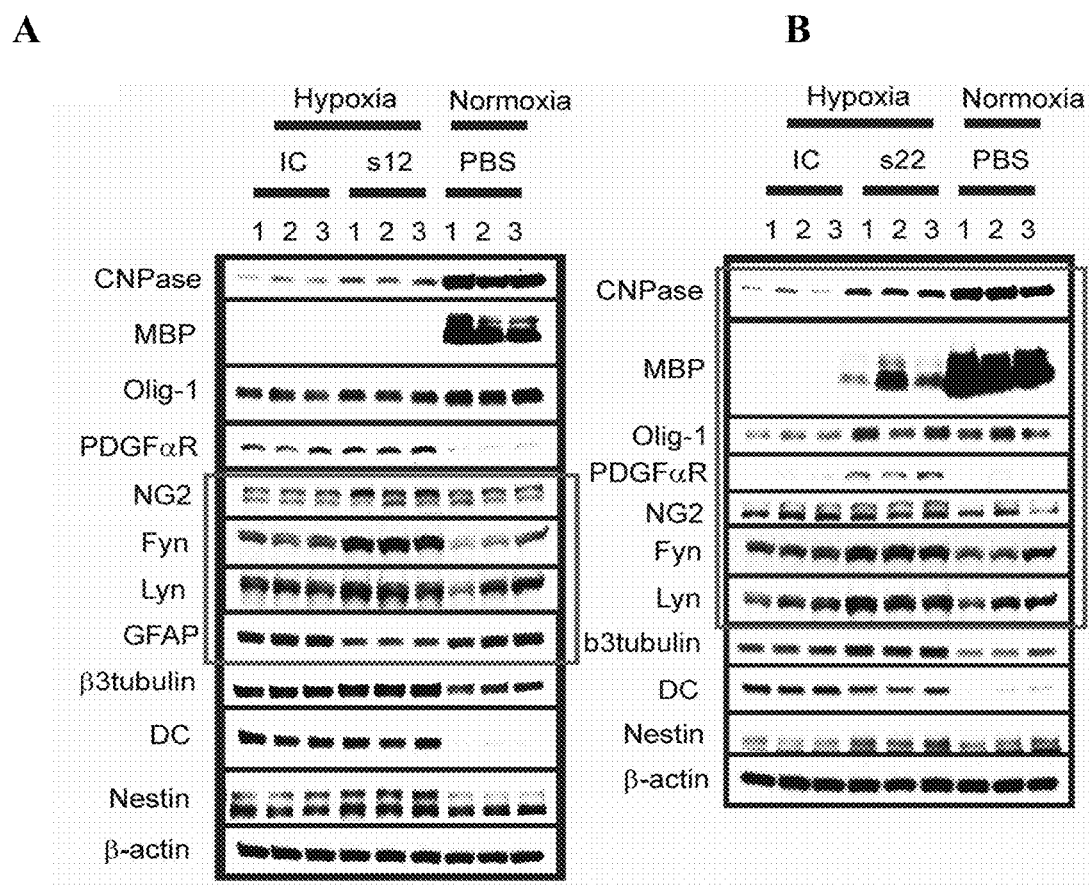
FIG. 8A-8B depicts Western blots of normoxia and hypoxia mice sacrificed at P13 and assessed for various myelin and brain proteins. (A) provides Western blots of normoxia and hypoxia mice treated with isotype control (IC) antibody, HIgM12 antibody or PBS. (B) provides Western blots of normoxia and hypoxia mice treated with isotype control (IC) antibody, HIgM22 antibody or PBS. Each lane represents an individual animal, with 1.5 mg brain tissue loaded. Proteins evaluated are CNPase, MBP, Olig-1, PDGFαR, NG2, Fyn, Lyn, GFAP, β3tubulin, double cortin (DC), nestin and β-actin (control) as indicated.

As shown in FIG. 8, HIgM12 reduces levels of stem cell marker GFAP, and increased levels of OPC markers NG2 and PDGFαR and levels of kinases Fyn and Lyn six days (P13) after the antibody injection at P7. HIgM22 increases levels of myelin markers CNPase and MBP, stimulates expression of OPC markers Olig-1 and PDGFαR, and increases levels of kinases Fyn and Lyn. Fyn is ubiquitously present in CNS cells with the exception of microglia. Lyn is expressed at a high level in microglia/macrophages and to a lower extent in OPCs and neurons. In OPCs, Fyn is involved in differentiation while Lyn mediates OPC proliferation. Both Src family kinases may be used as key molecules in future mechanistic studies and may serve as indicators of successful antibody delivery into the brain. In contrast, neuroblast markers doublecortin and β3tubulin showed no or little differences between both hypoxic groups (12 vs IC or 22 vs IC). HIgM12 and HIgM22 both stimulated expression of the neural stem cell marker/angiogenesis marker Nestin.

Figure 9:
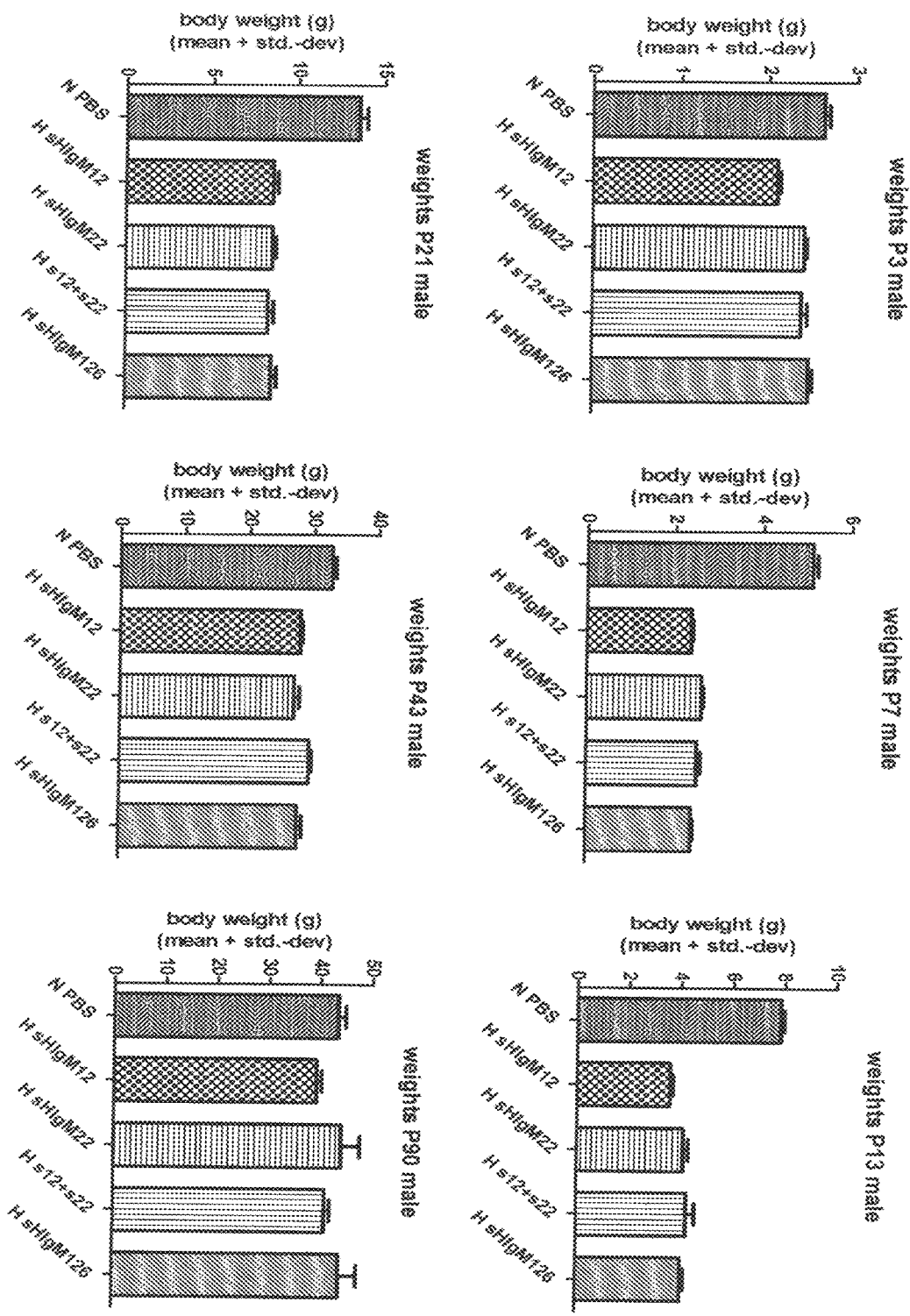
FIG. 9 depicts body weight measurements of normoxic animals mock treated with PBS (N, PBS), compared to hypoxic animals given various treatments. Hypoxic animals are indicated by H, followed by the antibody administered. Mice were treated with a single dose of either PBS (normoxia), human antibody HIgM12, HIgM22, a combination of antibodies HIgM22+HIgM12, or isotype control antibody HIgM126 in the hypoxic groups (30 µg each antibody per mouse/60 µg per animal for the combined treatment 12+22). Weights were measured in grams at P3, P7, P13, P21, P43 and P90 as indicated.

Body weight of hypoxic animals were evaluated after treatment with or administration of HIgM12, HIgM22 or a combination of HIgM12 and HIgM22 antibodies, compared to normoxic animals administered PBS. Weights of male mice were assessed at P3, P7, P13, P21 (postnatal day 21, weaning age), P43 (postnatal day 43, early adulthood of mice) and P90 (mouse adulthood) (FIG. 9).

These results indicate a stimulating role of HIgM12 on stem cell differentiation. HIgM12 may also facilitate angiogenesis resulting in higher OPC levels that may lead to higher myelin levels over time. In contrast, HIgM22 has an impact on OPC differentiation and possibly OPC proliferation.

These results show efficacy with antibodies HIgM22, HIgM12, or a combination of HIgM12 and HIgM22 antibodies, in a hypoxia-mediated model of PVL. Antibodies HIgM22 and HIgM12 rescued the phenotype while control antibody HIgM126 had no effect in this model. Myelin quality is reported to serve as a possible explanation for the persisting motor phenotype during adulthood while myelin quantity and other molecular marker(s) catch up typically within two weeks after the hypoxic insult. It is surprising to see a molecular outcome—biochemical changes in Western blots—with antibodies administered six days after the treatment in P13 neonatal mice (FIG. 8), which is in contrast to results seen in a viral model of demyelination during the chronic axonal phase of demyelination using adult mice. This further emphasizes the importance of the PVL model developed in neonatal mice showing systemic effects on myelination and development. In contrast, spinal cords of virally demyelinated mice show only 10-20% demyelinated lesions with the surrounding tissue having normal myelin levels. It may also underline the importance of progenitor cells abundantly present early postnatal but to a much lower extent during adulthood. Chronically demyelinated brain and spinal cord lesions are expected to have particularly low OL progenitor pools due to the lesions hostile, non-permissive environment. Thus, hypoxic neonatal animals are particularly responsive to the neuroactive antibodies including HIgM12 and HIgM22.

Based on dosing studies performed in adult mice using 10 µg of antibody per gram body weight we expect the optimal dose for the treatment of hypoxia-mediated PVL to be in the range of between 7.5 µg per mouse (2.5 µg per gram body weight) and 75 µg per mouse (25 µg per gram body weight). Pre-term infants with very low birth weight (<1200 g) are particularly vulnerable to the hypoxic-ischemic environment. A low dose of antibody administered into a 1200 g premature neonate would be 3 mg and a high antibody dose would be 30 mg for a 1200 g premature neonate. However, based on the vast amount of stem cells and progenitor cells in neonatal mice at the time of treatment, lower levels of antibodies may be sufficient to rescue the motor phenotype and to improve myelin quality.

The above results indicate HIgM12 stimulates stem cell differentiation and may also facilitate angiogenesis resulting in higher OPC levels, leading to higher myelin levels over time in neonatal hypoxia-ischemia and PVL. HIgM22 impacts OPC differentiation and possibly OPC proliferation more directly in the PVL model. Thus, while each and both of HIgM12 and HIgM22 antibodies correct aspects of and rescue the PVL phenotype and neuropathology, they act via apparently distinct pathways or mechanisms and cell stimulatory signals. It is remarkable that these distinct human monoclonal antibodies, particularly administered in a single dose i.p. serve to correct PVL.

EXAMPLE 3

A novel model of PVL has been developed in which neonatal mice exposed to chronic hypoxia (10% $O_2$) from postnatal days 3 (P3) until P7 (see Example 1) develop extensive hypomyelination and persistent neuromotor deficits throughout adulthood. While myelin quantity normalizes by adulthood, myelin quality however remains poor and is potentially responsible for the observed motor phenotype (4, 5).

Human antibodies that stimulate remyelination and function in models of primary demyelination have been previously described (6-14). The human antibody HIgM22 recently entered phase I clinical trials in multiple sclerosis patients (ClinicalTrials.gov Identifier: NCT01803867. "An Intravenous Infusion Study of rHIgM22 in Patients With Multiple Sclerosis"). Another human antibody, HIgM12, induced functional improvement during the chronic axonal phase of Theiler's virus infection (14) and enhanced survival in SOD mice (a model of amyotrophic lateral sclerosis, or ALS). Both HIgM22 and HIgM12 human antibodies target CNS progenitor cells and possibly neural stem cells (FIG. 5) that are abundantly expressed during embryonic and early postnatal stages in humans and mice. Strong evidence confirms that human and mouse remyelination promoting antibodies HIgM22 and SCH94.03 cross the blood brain barrier and target demyelinated lesions (15, 16).

The above Example 2 data shows that a single intraperitoneal dose of the HIgM12 monoclonal antibody and/or HIgM22 monoclonal antibody—either alone or in combination—at the end of a period of hypoxia (administered at P7 in this model) almost completely rescue the severe PVL-like motor phenotype in hypoxia-induced PVL model mice. Control human antibodies had no effect.

Human antibodies can serve as potent myelinating agents and improve function through binding to CNS progenitor cells (neuroblasts and OPCs) and possibly neural stem cells abundantly present during early developmental stages. These studies are designed to further demonstrate efficacy with human antibodies in the hypoxia-driven PVL model with a longitudinal study design that includes adulthood (P13, P60, P80). Demonstration of successful treatment is based on myelin markers at P13 and neuromotor function and quality of myelin during adulthood (P60 and P80) by blinded reviewers.

As a primary endpoint, levels of myelin proteins MBP, PLP, MOG at P13 in Western blots (myelin quantity) are evaluated. Secondary endpoints are (i) at P60, evaluation of neuro-motor behavior of mice in hanging wire tests and (ii) at P80, measurement of g-ratio and axonal myelination by electron microscopy (myelin quality). This evaluation is set to demonstrate a clear increase with HIgM12 or HIgM22 treatment in myelin quantity or myelin quality plus motor outcome.

Using the new short hypoxia mouse model of Periventricular Leukomalacia (PVL) (Example 1) that induces hypomyelination and persistent motor deficits in male neonatal mice, antibodies are evaluated in the PVL model.

General procedure: Timed pregnant CD1 mice are obtained from Charles River laboratories with an average litter size of 12-15 pups. Litters are culled down to 12 neonatal mice within the first 24 hrs after birth. Neonatal CD1 mice plus dam are reared under hypoxia for 96 h from postnatal day 3 (P3) until P7 under constant chronic hypoxia (10±0.5% O2). Proper functioning of the oxygen sensor is determined before each run and oxygen levels are checked every other hour for the first 12 hrs and twice daily every consecutive day. Age matched control mice are housed under identical conditions under room air (21% O2). At P7 mice are removed from the hypoxic chamber, injected i.p. with PBS or antibodies and housed under normal, normoxic conditions. Normoxic control animals receive PBS i.p. All neonatal mice receive ear punches at P7 directly before the antibody/PBS injection (left ear=antibody x; right ear=antibody y). Half the litter receive antibodies from the category one and the other half receive antibodies from category two. Category one antibodies are HIgM12 or HIgM22 and category 2 antibodies are control antibodies HIgM116 or HIgM126. All antibodies are administered in a blinded manner with mice randomly assigned to antibody category one or two. Female mice are sacrificed at weaning age P21 and male mice assigned to groups of 3 or 4 per cage depending on the number of male mice per litter.

Myelin quantity is determined at P13 by Western blotting and myelin quantity by electron microscopy at P80. The motor outcome is tested at P60 using hanging wire tests (mesh wire and single wire), using standard procedures. All studies are performed in a blinded manner. In addition, weights and survival rates of control and treated animals are compared. For myelin quantity assessment, mice are perfused with PBS only at P13 and cerebral myelin proteins analyzed by Western blotting. Myelin quantity is analyzed by densitometry of Western blots. Protein levels are normalized to levels of beta-actin to guarantee equal protein loading. Cerebral myelin quality is analyzed by electron microscopy at P90. Mice are perfused with 4% paraformaldehyde containing 0.5% glutaraldehyde and post-fixed for two weeks. Tissue samples are post-fixed in 1% osmium tetroxide, dehydrated and embedded in Araldite. Thin sagittal sections of white matter are stained with potassium permanganate and alcoholic uranyl acetate and examined by transmission electron microscopy. Measurements are performed by an individual blinded to groups. At least 100 axons are measured for each brain with 10 brains per hypoxic treatment group (HIgM12, HIgM22, control antibody HIgM126) and 10 normoxic control brains (PBS group). Measurements and image processing are performed using NIH Image J. Myelin thickness is calculated from the average of radial measurements at four points per sheath, avoiding areas of tongue processes or fixation artifact. Axon diameters are calculated from measurement of the axon circumference. Axons with diameters typical of unmyelinated fibres (0.3 mm) are excluded from the analysis. The extent of myelination is quantitatively compared by determining g ratios, which are calculated by dividing the diameter of the axon by the diameter of the entire myelinated fibre, as described elsewhere (24, 25).

Behavioral tests: Hanging wire tests are performed within one week with 3 repeats per mouse and day and 30 minutes breaks between each run. The best performance per mouse is counted for the hanging wire analysis due to possible fatigue induced by consecutive trials (motor coordination but not endurance is the primary outcome tested for). For behavioral tests the recommended minimal number of animals is 10 per group, thus twenty animals per treatment group are tested.

Dosing studies are performed to evaluate and identify the optimal dose of both human antibodies HIgM12 and HIgM22 for the treatment of hypoxia-mediated PVL in mice. Based on the outcome of both human antibodies in previous studies using adult mice 0.25 µg antibody/gram body weight is used as the lowest dose (~0.75 µg/mouse), 2.5 µg antibody/gram body weight as the medium dose (~7.5 µg/mouse) and 25 µg antibody/gram body weight as the highest dose (~75 µg/mouse). Antibodies are administered i.p. in animals at P7 after the hypoxic insult. The total volume injected is 50 nl per mouse.

Statistical Analysis: The assumption of normality is evaluated using the Shapiro-Wilk test for normality prior to additional analysis (Sigma Plot v11.0). Normally distributed data is analyzed by Student's unpaired, two-tailed t-test (2 groups) or ANOVA (>2 groups). Data not normally distributed is analyzed using the Mann-Whitney U test (2 groups) or Kruskal-Wallis one-way ANOVA (>2 groups). A probability of $p<0.05$ is set as the level of significance for all comparisons.

As another example the above protocol can be carried out using antibodies IgM42 and IgM46.

REFERENCES

1. Ferriero D M (2004) Neonatal brain injury. *N Engl J Med* 351(19):1985-1995.
2. Volpe J J (2003) Cerebral white matter injury of the premature infant-more common than you think. *Pediatrics* 112(1 Pt 1):176-180.
3. Back S A, et al. (2006) Protective effects of caffeine on chronic hypoxia-induced perinatal white matter injury. *Ann Neurol* 60(6):696-705.
4. Jablonska B, et al. (2012) Oligodendrocyte regeneration after neonatal hypoxia requires FoxO1-mediated p27Kip1 expression. *J Neurosci* 32(42):14775-14793.
5. Scafidi J, et al. (2014) Intranasal epidermal growth factor treatment rescues neonatal brain injury. *Nature* 506 (7487):230-234.
6. Asakura K, et al. (1996) Monoclonal autoantibody SCH94.03, which promotes central nervous system remyelination, recognizes an antigen on the surface of oligodendrocytes. *J Neurosci Res* 43 (3):273-281.
7. Asakura K, Miller D J, Pease L R, & Rodriguez M (1998) Targeting of IgMkappa antibodies to oligodendrocytes promotes CNS remyelination. *J Neurosci* 18(19):7700-7708.
8. Asakura K, Pogulis R J, Pease L R, & Rodriguez M (1996) A monoclonal autoantibody which promotes central nervous system remyelination is highly polyreactive to multiple known and novel antigens. J Neuroimmunol 65(1):11-19.

9. Bieber A J, et al. (2002) Human antibodies accelerate the rate of remyelination following lysolecithin-induced demyelination in mice. *Glia* 37(3):241-249.
10. Miller D J, Sanborn K S, Katzmann J A, & Rodriguez M (1994) Monoclonal autoantibodies promote central nervous system repair in an animal model of multiple sclerosis. *J Neurosci* 14(10):6230-6238.
11. Pavelko K D, van Engelen B G, & Rodriguez M (1998) Acceleration in the rate of CNS remyelination in lysolecithin-induced demyelination. *J Neurosci* 18(7):2498-2505.
12. Warrington A E, et al. (2000) Human monoclonal antibodies reactive to oligodendrocytes promote remyelination in a model of multiple sclerosis. *Proceedings of the National Academy of Sciences of the United States of America* 97(12):6820-6825.
13. Warrington A E, et al. (2007) A recombinant human IgM promotes myelin repair after a single, very low dose. *J Neurosci Res* 85(5):967-976 (in eng).
14. Denic A, et al. (2011) A single dose of neuron-binding human monoclonal antibody improves spontaneous activity in a murine model of demyelination. (Translated from eng) *PloS one* 6(10):e26001.
15. Hunter S F, Miller D J, & Rodriguez M (1997) Monoclonal remyelination-promoting natural autoantibody SCH 94.03: pharmacokinetics and in vivo targets within demyelinated spinal cord in a mouse model of multiple sclerosis. *J Neurol Sci* 150(2):103-113.
16. Pirko I, et al. (2004) A human antibody that promotes remyelination enters the CNS and decreases lesion load as detected by T2-weighted spinal cord MRI in a virus-induced murine model of MS *Faseb J* 18(13):1577-1579.
17. Titomanlio L, et al. (2011) Stem cell therapy for neonatal brain injury: perspectives and challenges. *Ann Neurol* 70(5):698-712.
18. Silbereis J C, Huang E J, Back S A, & Rowitch D H (2010) Towards improved animal models of neonatal white matter injury associated with cerebral palsy. *Dis Model Mech* 3(11-12):678-688.
19. Denic A, et al. (2012) Deletion of beta-2-microglobulin ameliorates spinal cord lesion load and promotes recovery of brainstem NAA levels in a murine model of multiple sclerosis. *Brain Pathol* 22(5):698-708.
20. Watzlawik J, et al. (2010) Human remyelination promoting antibody inhibits apoptotic signaling and differentiation through Lyn kinase in primary rat oligodendrocytes. *Glia* 58(15): 1782-1793.
21. Watzlawik J O, Warrington A E, & Rodriguez M (2013) PDGF is required for remyelination-promoting IgM stimulation of oligodendrocyte progenitor cell proliferation. *PloS one* 8(2):e55149.
22. Warrington A E, et al. (2004) Neuron-binding human monoclonal antibodies support central nervous system neurite extension. *J Neuropathol Exp Neurol* 63(5):461-473.
23. Xu X, et al. (2011) A human IgM signals axon outgrowth: coupling lipid raft to microtubules. *J Neurochem* 119(1): 100-112.
24. Furusho M, Dupree J L, Nave K A, & Bansal R (2012) Fibroblast growth factor receptor signaling in oligodendrocytes regulates myelin sheath thickness. *J Neurosci* 32(19):6631-6641.
25. Zhou Y X, Pannu R, Le T Q, & Armstrong R C (2012) Fibroblast growth factor 1 (FGFR1) modulation regulates repair capacity of oligodendrocyte progenitor cells following chronic demyelination. *Neurobiol Dis* 45(1):196-205.
26. Rice J E, 3rd, Vannucci R C, & Brierley J B (1981) The influence of immaturity on hypoxic-ischemic brain damage in the rat. *Ann Neurol* 9(2):131-141.

EXAMPLE 4

In Vivo Blinded Study in PVL/Neonatal White Matter Injury (WMI) Model

The overall goal of this experiment was to demonstrate efficacy using a recombinant human antibody (the recombinant antibody rHIgM22) in a mouse model of neonatal white matter injury (nWMI) and PVL. The results of this study may have implications for clinical trials in neonates at risk for cerebral white matter injury, such as term neonates with hypoxic-ischemic encephalopathy and premature neonates with periventricular leukomalacia.

Overall Procedural Design:

Timed-pregnant CD1 mice were purchased from Charles River Laboratories. Only litter sizes 12 or bigger were used in the experiment. On postnatal day 3 (P3) litters with numbers higher 12 were culled down to 12 neonatal mice per dam. The animal model described in Example 1 was utilized. At P3, three randomly chosen litters plus dam were exposed to hypoxia (10% O2) for 96 hours from postnatal day 3 (P3) to P7. Also, 2 different litters plus dam were housed under room air (normoxia). At P7, neonatal mice in control groups (normoxia) were injected i.p. with PBS, neonatal mice in hypoxic groups were injected i.p. with a single dose of compound X, Y or Z. Investigators performing the experiment (at Mayo Clinic) were blinded for treatment groups (X,Y, Z).

For each hypoxic litter (12 neonatal mice): 4 neonatal mice per litter received treatment X, 4 neonatal mice received treatment Y, and 4 neonatal mice received treatment Z. Injection volume was 30 µl per animal. At P13 all animals were sacrificed, brains were flash-frozen and stored at −80° C.; body weights, brain weights and sex were noted. Whole brain hemispheres were lyzed and homogenized; 750 µg of brain tissue from each animal were loaded in Western blots and probed against PLP, MBP and CNPase, with β-actin as a loading control.

Treatment groups P7:

Hypoxia Litter 1: 4 pups treatment X, 4 pups treatment Y, 4 pups treatment Z
Hypoxia Litter 2: 4 pups treatment X, 4 pups treatment Y, 4 pups treatment Z
Hypoxia Litter 3: 4 pups treatment X, 5 pups treatment Y, 4 pups treatment Z
Normoxia Litter 1: 12 pups received PBS
Normoxia Litter 2: 12 pups received PBS
  Z=rHIgM22, 15 µg in 30 µl
  Y=PBS, 30 µl
  X=Isotype control IgM (ChromPure human IgM; Jackson Immunoresearch Laboratories, INC., #009-000-012), 15 µg in 30 µl Investigators were blinded to the treatment groups for the study. After completion of analysis, the investigators were unblinded for the above treatment groups.

Outcome:

All neonatal mice survived the assignment to hypoxia and the antibody injections. No obvious antibody/PBS "leakage" was detectable when using 31×g needles. At P13, animals were sacrificed and cerebra from all groups was analyzed by Western blotting using antibodies against various CNS proteins (proteolipid protein (PLP), myelin basic protein (MBP), CNPase) and β-actin as a loading control. Antibodies used for Western blotting were as described in Example 2.

Figure 14:
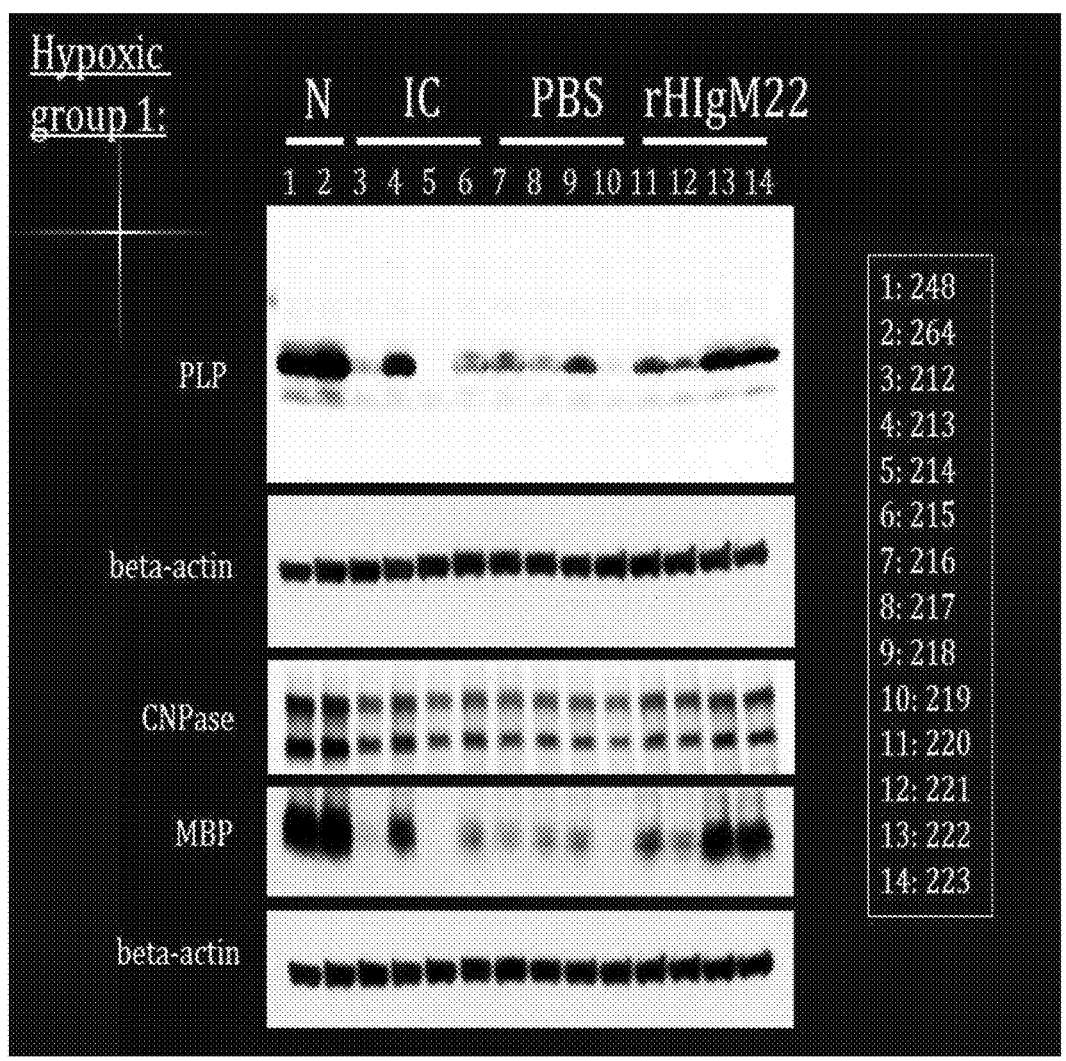
FIG. 14 provides CNS Western blots analysis of control and hypoxic mice. Representative Western blots using whole brain lysates of P13 hypoxic and control CD1 mice showing levels of myelin proteins PLP, CNPase, MBP and loading control beta-actin. Each lane is representing an individual animal. Beta-actin levels are shown for each Western blot and placed below the myelin proteins. Animals 1-2 were reared under room air (N=normoxic control animals). Animals 3-14 were reared under hypoxia (10% O2) (P3→P7) and treated with human isotype control (IC, ChromPure IgM), PBS or rHIgM22 at P7.
Figure 15:
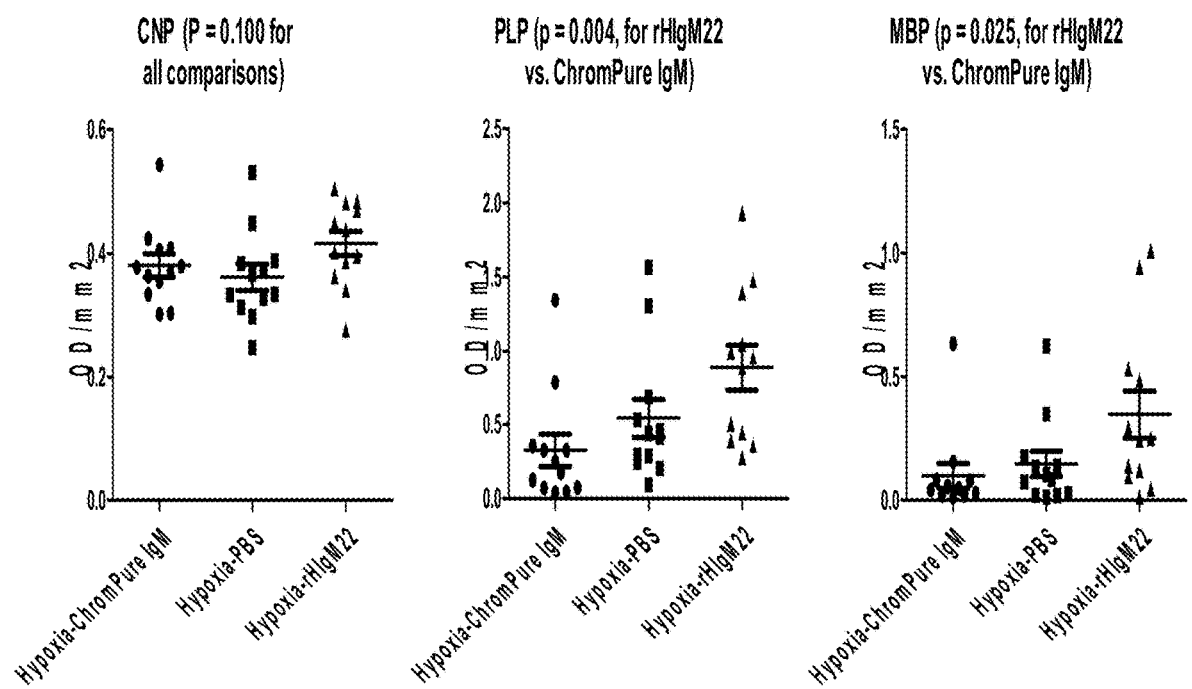
FIG. 15 shows rHIgM22 stimulates PLP and MBP expression in neonatal mice reared under hypoxia. Scatter plots showing levels of myelin proteins CNP, PLP and MBP per treatment group (rHIgM22, PBS, human isotype control IgM (ChromPure IgM)) based on densitometric analysis of Western blots using whole brain lysates of P13 hypoxic CD1 mice. Neonatal mice from three different litters (n=12 per litter) were reared under hypoxia (P3→P7) and intraperitoneally (i.p.) injected with 30 µl of rHIgM22, PBS or human isotype control IgM (ChromPure IgM) at P7. Each animal is reflected by an individual symbol (circle, square, triangle). Statistical analysis was performed in Sigma Plot using the Kruskal-Wallis One Way Analysis of Variance on Ranks function (Anova on Ranks).

Representative Western blots are shown in FIG. 14. Densitometric analysis of Western blots demonstrated significantly higher levels of myelin proteins proteolipid protein (PLP) and myelin basic protein (MBP) in treatment group Z versus treatment group X (FIG. 15). The difference in PLP and MBP protein levels remained significant over a range of parametric and non-parametric tests (student's t-test, Mann-Whitney Rank Sum Test, Kruskal-Wallis One Way Analysis of Variance on Ranks). Differences in myelin protein levels for MBP and PLP between groups Z and Y were close to significance ($p=0.089$ for MBP and PLP). Antibody rHIgM22 (Group Z) stimulates PLP and MBP expression in neonatal mice reared under hypoxia.

In summary, all injected antibodies had no adverse effects in neonatal mice. Differences in myelin protein levels at P13 were significantly different between treatment groups Z (rHIgM22 antibody) and X (isotype control antibody) in neonatal mice reared under hypoxia.

Further studies are in progress to perform dose response measurements in neonatal mice to identify the minimal effective dose of rHIgM22 on CNS myelin levels at P13. In addition, studies to assess antibody (rHIgM22, rHIgM12) effects on persistent motor disabilities and chronic markers of hypoxic-ischemic CNS injury in male adult mice (3 months). The focus of these studies is neuro-motor behavioral analysis and axonal preservation in brain and spinal cord.

This invention may be embodied in other forms or carried out in other ways without departing from the spirit or essential characteristics thereof The present disclosure is therefore to be considered as in all aspects illustrate and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

What is claimed is:

1. A method for treatment or amelioration of white matter disease or injury or Periventricular Leukomalacia (PVL) in an infant comprising administering to an infant suspected of or determined to have white matter disease or injury or PVL an effective amount of a pharmaceutical composition comprising an isolated human IgM antibody or fragment thereof, wherein the antibody or fragment comprises the variable heavy chain amino acid CDR domain sequences CDR1 SSGMH (SEQ ID NO: 11), CDR2 V(I)ISYDGSRKYYADSVKG (SEQ ID NO:12) and CDR3 GVTGSPTLDY (SEQ ID NO:13), and light chain CDR sequences CDR1 SGSSSNIGNNFVS (SEQ ID NO: 14), CDR2 DITKRPS (SEQ ID NO:15) and CDR3 G(E)TWDSSLSAVV (SEQ ID NO: 16), or the variable heavy chain amino acid CDR domain sequences CDR1 SSGMH (SEQ ID NO: 11), CDR2 VAIISYDGSRKYYADSVKG (SEQ ID NO:55) and CDR3 GVTGSPTLDY (SEQ ID NO:13), and light chain CDR sequences CDR1 SGSSSNIGNNFVS (SEQ ID NO: 14), CDR2 DITKRPS (SEQ ID NO:15) and CDR3 CETWDSSLSAVV (SEQ ID NO: 56), wherein the composition is administered within seconds, minutes, or hours after birth as a single dose to said infant suspected of or determined to have white matter disease or injury or PVL.

2. The method of claim 1 wherein the antibody or fragment comprises the variable heavy chain amino acid sequence set out in SEQ ID NO: 17 and the variable light chain amino acid sequence set out in SEQ ID NO: 18 or variants thereof having at least 90% amino acid sequence identity thereto, wherein said variants retain neuron binding and activity for treatment of white matter disease or injury in an infant.

3. The method of claim 1 wherein the composition is administered within hours after birth.

4. The method of claim 1 wherein the composition is administered to a premature or low birth weight infant within 1 hour after birth.

5. The method of claim 1 wherein the composition is administered to a premature or low birth weight infant within the first 1, 2, 3, 4, 5, 6, 7, 8, 9 or 10 hours after birth.

6. The method of claim 1 wherein the composition is administered to a premature or low birth weight infant within 24 hours after birth.

7. The method of claim 1 further comprising administering an effective amount of a pharmaceutical composition comprising an isolated human IgM antibody or fragment thereof, wherein the antibody or fragment comprises:

(a) the variable heavy chain amino acid CDR domain sequences CDR1 GGSVSLYY (SEQ ID NO:1), CDR2 GYIYSSGST (SEQ ID NO:2) and CDR3 ARSASIRGWFD (SEQ ID NO:3), and light chain CDR sequences CDR1 QSISSY (SEQ IDNO: 4), CDR2 AAS (SEQ ID NO:5) and CDR3 QQSYHTPW (SEQ ID NO:6); or (b) the variable heavy chain amino acid sequence set out in SEQ ID NO: 7 and the variable light chain amino acid sequence set out in SEQ ID NO: 8.

8. A method for treatment of white matter disease or injury or Periventricular Leukomalacia (PVL) in an infant comprising administering to an infant having one or more risk factor for PVL an effective amount of a pharmaceutical composition comprising an isolated human IgM antibody or fragment thereof, wherein the antibody or fragment comprises the variable heavy chain amino acid CDR domain sequences CDR1 SSGMH (SEQ ID NO: 11), CDR2 V(I) ISYDGSRKYYADSVKG (SEQ ID NO:12) and CDR3 GVTGSPTLDY (SEQ ID NO:13), and light chain CDR sequences CDR1 SGSSSNIGNNFVS (SEQ ID NO: 14), CDR2 DITKRPS (SEQ ID NO:15) and CDR3 G(E) TWDSSLSAVV (SEQ ID NO: 16), or the variable heavy chain amino acid CDR domain sequences CDR1 SSGMH (SEQ ID NO: 11), CDR2 VAIISYDGSRKYYADSVKG (SEQ ID NO:55) and CDR3 GVTGSPTLDY (SEQ ID NO:13), and light chain CDR sequences CDR1 SGSSSNIGNNFVS (SEQ ID NO: 14), CDR2 DITKRPS (SEQ ID NO:15) and CDR3 CETWDSSLSAVV (SEQ ID NO: 56), wherein the composition is administered within seconds, minutes, or hours after birth as a single dose to said infant suspected of or determined to have white matter disease or injury or PVL.

9. The method of claim 8 wherein the risk factor for PVL is one or more factor selected from low Apgar score, relatively long periods of ventilation and oxygen inhalation, a persistent presence of apneic spells, prolonged or repetitive variable decelerations during labor, respiratory distress syndrome type I, infants born to mothers who suffered from preterm premature rupture of membranes, preeclampsia or clinical chorioamnionitis, very low birth weight premature infants (VLBWI), VLBWI with chorioamnionitis, or VLBWI with neonatal sepsis.

10. The method of claim 8 wherein the antibody or fragment comprises the variable heavy chain amino acid sequence set out in SEQ ID NO: 17 and the variable light chain amino acid sequence set out in SEQ ID NO: 18 or variants thereof having at least 90% amino acid sequence identity thereto, wherein said variants retain neuron binding and activity for treatment of white matter disease or injury or PVL in an infant.

11. The method of claim 8 further comprising administering an effective amount of a pharmaceutical composition comprising an isolated human IgM antibody or fragment thereof, wherein the antibody or fragment comprises:
- (a) the variable heavy chain amino acid CDR domain sequences CDR1 GGSVSLYY (SEQ ID NO:1), CDR2 GYIYSSGST (SEQ ID NO:2) and CDR3 ARSASIRGWFD (SEQ ID NO:3), and light chain CDR sequences CDR1 QSISSY (SEQ ID NO: 4), CDR2 AAS (SEQ ID NO:5) and CDR3 QQSYHTPW (SEQ ID NO:6); or
- (b) the variable heavy chain amino acid sequence set out in SEQ ID NO: 7 and the variable light chain amino acid sequence set out in SEQ ID NO: 8.

12. The method of claim 8 wherein the composition is administered within hours after birth.

13. The method of claim 8 wherein the composition is administered to a premature or low birth weight infant within 1 hour after birth.

14. The method of claim 8 wherein the composition is administered to a premature or low birth weight infant within the first 1, 2, 3, 4, 5, 6, 7, 8, 9 or 10 hours after birth.

15. The method of claim 8 wherein the composition is administered to a premature or low birth weight infant within 24 hours after birth.

\* \* \* \* \*

SEQUENCE LISTING

```
<160> NUMBER OF SEQ ID NOS: 56

<210> SEQ ID NO 1
<211> LENGTH: 8
<212> TYPE: PRT
<213> ORGANISM: Homo sapiens

<400> SEQUENCE: 1

Gly Gly Ser Val Ser Leu Tyr Tyr
1               5

<210> SEQ ID NO 2
<211> LENGTH: 9
<212> TYPE: PRT
<213> ORGANISM: Homo sapiens

<400> SEQUENCE: 2

Gly Tyr Ile Tyr Ser Ser Gly Ser Thr
1               5

<210> SEQ ID NO 3
<211> LENGTH: 11
<212> TYPE: PRT
<213> ORGANISM: Homo sapiens

<400> SEQUENCE: 3

Ala Arg Ser Ala Ser Ile Arg Gly Trp Phe Asp
1               5                   10

<210> SEQ ID NO 4
<211> LENGTH: 6
<212> TYPE: PRT
<213> ORGANISM: Homo sapiens

<400> SEQUENCE: 4

Gln Ser Ile Ser Ser Tyr
1               5

<210> SEQ ID NO 5
<211> LENGTH: 3
<212> TYPE: PRT
<213> ORGANISM: Homo sapiens
```

<400> SEQUENCE: 5

Ala Ala Ser
1

<210> SEQ ID NO 6
<211> LENGTH: 8
<212> TYPE: PRT
<213> ORGANISM: Homo sapiens

<400> SEQUENCE: 6

Gln Gln Ser Tyr His Thr Pro Trp
1               5

<210> SEQ ID NO 7
<211> LENGTH: 118
<212> TYPE: PRT
<213> ORGANISM: Homo sapiens

<400> SEQUENCE: 7

Gln Val Gln Leu Gln Glu Ser Gly Pro Gly Leu Leu Lys Pro Ser Glu
1               5                   10                  15

Thr Leu Ser Leu Thr Cys Thr Val Ser Gly Gly Ser Val Ser Leu Tyr
            20                  25                  30

Tyr Trp Ser Trp Ile Arg Gln Ser Pro Gly Lys Glu Pro Glu Trp Ile
        35                  40                  45

Gly Tyr Ile Tyr Ser Ser Gly Ser Thr Asp Tyr Asn Pro Ser Leu Arg
    50                  55                  60

Ser Arg Val Thr Ile Ser Leu Asp Thr Ser Asn Asn Arg Phe Ser Leu
65                  70                  75                  80

Asn Leu Arg Ser Val Thr Ala Ala Asp Thr Ala Val Tyr Trp Cys Ala
                85                  90                  95

Arg Ser Ala Ser Ile Arg Gly Trp Phe Asp Pro Trp Gly Gln Gly Thr
            100                 105                 110

Leu Val Thr Val Ser Ser
        115

<210> SEQ ID NO 8
<211> LENGTH: 105
<212> TYPE: PRT
<213> ORGANISM: Homo sapiens

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Val Leu Ile
        35                  40                  45

Tyr Ala Ala Ser Thr Leu Arg Ser Gly Val Pro Ser Arg Phe Ser Gly
    50                  55                  60

Ser Gly Ser Gly Thr Asp Phe Thr Leu Ser Val Ser Ser Leu Gln Pro
65                  70                  75                  80

Glu Asp Phe Ala Thr Tyr Tyr Cys Gln Gln Ser Tyr His Thr Pro Trp
                85                  90                  95

Thr Phe Gly Gln Gly Thr Lys Val Glu
            100                 105

```
<210> SEQ ID NO 9
<211> LENGTH: 354
<212> TYPE: DNA
<213> ORGANISM: Homo sapiens

<400> SEQUENCE: 9
caggtgcagc tgcaggagtc gggcccagga ctgctgaagc cttcggagac cctgtccctc      60
acatgcactg tctctggtgg ttccgtcagt ctttactact ggagctggat ccggcagtcc     120
ccagggaagg aaccggagtg gattggatat atctattcca gtggaagcac cgattacaac     180
ccttccctca ggagtcgagt caccatatca ctggacacgt caaacaaccg gttttcccta     240
aacctgaggt ctgtgaccgc cgcagataca gcggtctatt ggtgtgcgag aagtgcgtca     300
attaggggct ggttcgaccc ctggggccag ggaaccctgg tcaccgtctc ctca           354

<210> SEQ ID NO 10
<211> LENGTH: 315
<212> TYPE: DNA
<213> ORGANISM: Homo sapiens

<400> SEQUENCE: 10
gacatccaga tgacccagtc tccatcctcc ttgtctgcgt ctgtaggaga cagagtcacc      60
atcacttgcc gggcaagtca gagtattagt agttatctaa attggtatca gcagaaacca     120
gggaaagccc ctaaggtcct gatctatgct gcatccactt tgcgaagtgg ggtcccgtca     180
aggttcagtg gcagtggatc tgggacagat ttcactctca gcgtcagcag tctgcaacct     240
gaagattttg caacttacta ctgtcaacag agttaccata ccccgtggac gttcggtcag     300
gggaccaagg tggaa                                                      315

<210> SEQ ID NO 11
<211> LENGTH: 5
<212> TYPE: PRT
<213> ORGANISM: Homo sapiens

<400> SEQUENCE: 11

Ser Ser Gly Met His
1               5

<210> SEQ ID NO 12
<211> LENGTH: 17
<212> TYPE: PRT
<213> ORGANISM: Homo sapiens
<220> FEATURE:
<221> NAME/KEY: VARIANT
<222> LOCATION: (1)..(1)
<223> OTHER INFORMATION: X can be V or I

<400> SEQUENCE: 12

Xaa Ile Ser Tyr Asp Gly Ser Arg Lys Tyr Tyr Ala Asp Ser Val Lys
1               5                   10                  15
Gly

<210> SEQ ID NO 13
<211> LENGTH: 10
<212> TYPE: PRT
<213> ORGANISM: Homo sapiens

<400> SEQUENCE: 13

Gly Val Thr Gly Ser Pro Thr Leu Asp Tyr
1               5                   10
```

```
<210> SEQ ID NO 14
<211> LENGTH: 13
<212> TYPE: PRT
<213> ORGANISM: Homo sapiens

<400> SEQUENCE: 14

Ser Gly Ser Ser Ser Asn Ile Gly Asn Asn Phe Val Ser
1               5                   10

<210> SEQ ID NO 15
<211> LENGTH: 7
<212> TYPE: PRT
<213> ORGANISM: Homo sapiens

<400> SEQUENCE: 15

Asp Ile Thr Lys Arg Pro Ser
1               5

<210> SEQ ID NO 16
<211> LENGTH: 11
<212> TYPE: PRT
<213> ORGANISM: Homo sapiens
<220> FEATURE:
<221> NAME/KEY: VARIANT
<222> LOCATION: (1)..(1)
<223> OTHER INFORMATION: X can be G or E

<400> SEQUENCE: 16

Xaa Thr Trp Asp Ser Ser Leu Ser Ala Val Val
1               5                   10

<210> SEQ ID NO 17
<211> LENGTH: 119
<212> TYPE: PRT
<213> ORGANISM: Homo sapiens

<400> SEQUENCE: 17

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Ser
            20                  25                  30

Gly Met His Trp Val Arg Gln Ala Pro Gly Lys Gly Leu Glu Trp Val
        35                  40                  45

Ala Val Ile Ser Tyr Asp Gly Ser Arg Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Thr Ala Asp Thr Ala Val Tyr Tyr Cys
                85                  90                  95

Ala Lys Gly Val Thr Gly Ser Pro Thr Leu Asp Tyr Trp Gly Gln Gly
            100                 105                 110

Thr Leu Val Thr Val Ser Ser
        115

<210> SEQ ID NO 18
<211> LENGTH: 114
<212> TYPE: PRT
<213> ORGANISM: Homo sapiens
<220> FEATURE:
<221> NAME/KEY: VARIANT
<222> LOCATION: (46)..(46)
<223> OTHER INFORMATION: X can be R or K
<220> FEATURE:
<221> NAME/KEY: VARIANT
```

<222> LOCATION: (90)..(90)
<223> OTHER INFORMATION: X can be G or E

<400> SEQUENCE: 18

Gln Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Phe Val Ser Trp Tyr Gln Gln Leu Pro Gly Thr Ala Pro Xaa Leu Leu
        35                  40                  45

Ile Tyr Asp Ile Thr Lys Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Xaa Thr Trp Asp Ser Ser Leu
                85                  90                  95

Ser Ala Val Val Phe Gly Gly Gly Thr Lys Leu Thr Val Leu Gly Gln
            100                 105                 110

Pro Lys

<210> SEQ ID NO 19
<211> LENGTH: 714
<212> TYPE: DNA
<213> ORGANISM: Homo sapiens
<220> FEATURE:
<221> NAME/KEY: variation
<222> LOCATION: (148)..(148)
<223> OTHER INFORMATION: n is g or a
<220> FEATURE:
<221> NAME/KEY: misc_feature
<222> LOCATION: (148)..(148)
<223> OTHER INFORMATION: n is a, c, g, or t
<220> FEATURE:
<221> NAME/KEY: variation
<222> LOCATION: (150)..(150)
<223> OTHER INFORMATION: n is t or c
<220> FEATURE:
<221> NAME/KEY: misc_feature
<222> LOCATION: (150)..(150)
<223> OTHER INFORMATION: n is a, c, g, or t
<220> FEATURE:
<221> NAME/KEY: variation
<222> LOCATION: (267)..(267)
<223> OTHER INFORMATION: n is g or c
<220> FEATURE:
<221> NAME/KEY: misc_feature
<222> LOCATION: (267)..(267)
<223> OTHER INFORMATION: n is a, c, g, or t
<220> FEATURE:
<221> NAME/KEY: variation
<222> LOCATION: (505)..(505)
<223> OTHER INFORMATION: n is g or a
<220> FEATURE:
<221> NAME/KEY: misc_feature
<222> LOCATION: (505)..(505)
<223> OTHER INFORMATION: n is a, c, g, or t
<220> FEATURE:
<221> NAME/KEY: variation
<222> LOCATION: (507)..(507)
<223> OTHER INFORMATION: n is t or c
<220> FEATURE:
<221> NAME/KEY: misc_feature
<222> LOCATION: (507)..(507)
<223> OTHER INFORMATION: n is a, c, g, or t
<220> FEATURE:
<221> NAME/KEY: variation
<222> LOCATION: (624)..(624)
<223> OTHER INFORMATION: n is g or c
<220> FEATURE:
<221> NAME/KEY: misc_feature
<222> LOCATION: (624)..(624)
<223> OTHER INFORMATION: n is a, c, g, or t

<400> SEQUENCE: 19

```
caggtgcagc tggtggagtc tggggggggc gtggtccagc ctggaggtc cctgagactc      60
tcctgtgcag cctctggatt caccttcagt agctctggca tgcactgggt ccgccaagct    120
ccaggcaagg ggctggagtg ggtggcantn atttcatatg atggaagtag gaaatactat    180
gcagactccg tgaagggccg attcaccatc tccagagaca actccaagaa cactctctat    240
ctgcaaatga acagcctgac ggctgangac acggctgtgt attattgtgc gaaaggagtg    300
actggtagtc cgacgcttga ctactggggc cagggaaccc tggtcaccgt ctcctcgcag    360
gtgcagctgg tggagtctgg ggggggcgtg gtccagcctg ggaggtccct gagactctcc    420
tgtgcagcct ctggattcac cttcagtagc tctggcatgc actgggtccg ccaagctcca    480
ggcaagggc tggagtgggt ggcantnatt tcatatgatg gaagtaggaa atactatgca    540
gactccgtga agggccgatt caccatctcc agagacaact ccaagaacac tctctatctg    600
caaatgaaca gcctgacggc tgangacacg gctgtgtatt attgtgcgaa aggagtgact    660
ggtagtccga cgcttgacta ctggggccag ggaaccctgg tcaccgtctc ctcg          714
```

<210> SEQ ID NO 20
<211> LENGTH: 342
<212> TYPE: DNA
<213> ORGANISM: Homo sapiens
<220> FEATURE:
<221> NAME/KEY: variation
<222> LOCATION: (137)..(137)
<223> OTHER INFORMATION: n is a or g
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: variation
<222> LOCATION: (269)..(269)
<223> OTHER INFORMATION: n is g or a
<220> FEATURE:
<221> NAME/KEY: misc_feature
<222> LOCATION: (269)..(269)
<223> OTHER INFORMATION: n is a, c, g, or t

<400> SEQUENCE: 20

```
cagtctgtgt tgacggagcc gccttcagtg tctgctgccc caggacagaa ggtcaccatc     60
tcctgctctg gaagcagctc caacattggc aataattttg tatcctggta ccagcaactc    120
ccaggaacag cccccanact cctcatttat gacattacta gcgaccctc agggattcct    180
gaccgattct ctggctccaa gtctggcacg tcagccaccc tgggcatcac cggactccag    240
actgggacg aggccgatta ttactgcgna acatgggata gcagcctgag tgctgtggta    300
ttcggcgggg ggaccaagct gaccgtccta ggtcagccca ag                       342
```

<210> SEQ ID NO 21
<211> LENGTH: 8
<212> TYPE: PRT
<213> ORGANISM: Homo sapiens

<400> SEQUENCE: 21

Gly Phe Thr Phe Ser Thr Tyr Ala
1               5

<210> SEQ ID NO 22
<211> LENGTH: 8

```
<212> TYPE: PRT
<213> ORGANISM: Homo sapiens

<400> SEQUENCE: 22

Ile Asn Val Gly Gly Val Thr Thr
1               5

<210> SEQ ID NO 23
<211> LENGTH: 15
<212> TYPE: PRT
<213> ORGANISM: Homo sapiens

<400> SEQUENCE: 23

Val Arg Arg Ser Gly Pro Asp Arg Asn Ser Ser Pro Ala Asp Phe
1               5                   10                  15

<210> SEQ ID NO 24
<211> LENGTH: 4
<212> TYPE: PRT
<213> ORGANISM: Homo sapiens

<400> SEQUENCE: 24

Gln Gly Ile Gly
1

<210> SEQ ID NO 25
<211> LENGTH: 3
<212> TYPE: PRT
<213> ORGANISM: Homo sapiens

<400> SEQUENCE: 25

Thr Thr Ser
1

<210> SEQ ID NO 26
<211> LENGTH: 9
<212> TYPE: PRT
<213> ORGANISM: Homo sapiens

<400> SEQUENCE: 26

Gln Lys Tyr Asn Ser Ala Pro Arg Thr
1               5

<210> SEQ ID NO 27
<211> LENGTH: 134
<212> TYPE: PRT
<213> ORGANISM: Homo sapiens

<400> SEQUENCE: 27

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
                20                  25                  30

Ala Met Ser Trp Val Arg Gln Ala Pro Gly Glu Gly Leu Glu Trp Val
            35                  40                  45

Ser Asp Ile Asn Val Gly Gly Val Thr Thr Tyr Tyr Ala Asp Ser Val
        50                  55                  60

Lys Gly Arg Phe Thr Ile Ser Arg Asp Asn Lys Asn Thr Leu Tyr
65                  70                  75                  80

Leu Gln Met Asn Ser Leu Arg Val Glu Asp Thr Ala Met Tyr Tyr Cys
                85                  90                  95

Val Arg Arg Ser Gly Pro Asp Arg Asn Ser Ser Pro Ala Asp Phe Trp
```

```
              100                 105                 110
Gly Gln Gly Ser Leu Val Ile Val Ser Ser Gly Ser Ala Ser Ala Pro
        115                 120                 125

Thr Leu Phe Pro Leu Val
    130

<210> SEQ ID NO 28
<211> LENGTH: 105
<212> TYPE: PRT
<213> ORGANISM: Homo sapiens

<400> SEQUENCE: 28

Asp Ile Gln Met Thr Gln Ser Pro Ser Ser Leu Ser Ala Ser Val Gly
1               5                  10                  15

Asp Arg Val Thr Ile Thr Cys Arg Ala Ser Gln Gly Ile Gly Asn Tyr
            20                  25                  30

Leu Ala Trp Tyr Gln Gln Lys Pro Gly Lys Val Pro Lys Leu Leu Ile
        35                  40                  45

Tyr Thr Thr Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Lys Tyr Asn Ser Ala Pro Arg
                85                  90                  95

Thr Phe Gly Gln Gly Thr Arg Val Asp
            100                 105

<210> SEQ ID NO 29
<211> LENGTH: 402
<212> TYPE: DNA
<213> ORGANISM: Homo sapiens

<400> SEQUENCE: 29
gaggtgcagc tgttggagtc tgggggaggc ttggtacagc ctggggggtc cctgagactc      60
tcctgtgcag cctctggatt cacctttagc acctatgcca tgagctgggt ccgccaggct     120
ccaggggagg ggctggagtg ggtctcagat attaatgttg gtggtgttac cacatactac     180
gcagactccg tgaagggccg gttcaccatc tccagagaca attccaagaa cacgctgtat     240
ctacaaatga acagcctgag agtagaggac acggccatgt attactgtgt gaggcggtcc     300
gggcccgatc gcaactcgtc gcccgctgac ttctggggcc agggatccct ggtcatcgtc     360
tcctcaggga gtgcatccgc cccaacccct tccccctcg tc                         402

<210> SEQ ID NO 30
<211> LENGTH: 315
<212> TYPE: DNA
<213> ORGANISM: Homo sapiens

<400> SEQUENCE: 30
gacatccaga tgacccagtc tccatcctcc ctgtctgcat ctgtaggaga cagagtcacc      60
atcacttgcc gggcgagtca gggcattggc aattatttag cctggtatca gcagaaacca     120
gggaaagttc ctaaactcct gatctatact acatccattt tgcaatcagg ggtcccatct     180
cgattcagtg gcagtggatc tgggacagat ttcactctca ccatcagcag cctgcagcct     240
gaagattttg caacttatta ctgtcaaaaa tataacagtg ccccgcggac gttcggccaa     300
gggaccaggg tggac                                                      315
```

```
<210> SEQ ID NO 31
<211> LENGTH: 9
<212> TYPE: PRT
<213> ORGANISM: Homo sapiens

<400> SEQUENCE: 31

Ser Gly Phe Thr Phe Ser Ser Tyr Trp
1               5

<210> SEQ ID NO 32
<211> LENGTH: 8
<212> TYPE: PRT
<213> ORGANISM: Homo sapiens

<400> SEQUENCE: 32

Ile Lys Lys Asp Gly Ser Glu Lys
1               5

<210> SEQ ID NO 33
<211> LENGTH: 16
<212> TYPE: PRT
<213> ORGANISM: Homo sapiens

<400> SEQUENCE: 33

Ala Arg Pro Asn Cys Gly Gly Asp Cys Tyr Leu Pro Trp Tyr Phe Asp
1               5                   10                  15

<210> SEQ ID NO 34
<211> LENGTH: 12
<212> TYPE: PRT
<213> ORGANISM: Homo sapiens

<400> SEQUENCE: 34

Gln Ser Val Leu Tyr Ser Ser Asn Asn Lys Asn Tyr
1               5                   10

<210> SEQ ID NO 35
<211> LENGTH: 4
<212> TYPE: PRT
<213> ORGANISM: Homo sapiens

<400> SEQUENCE: 35

Tyr Trp Ala Ser
1

<210> SEQ ID NO 36
<211> LENGTH: 9
<212> TYPE: PRT
<213> ORGANISM: Homo sapiens

<400> SEQUENCE: 36

Gln Gln Tyr Tyr Asn Thr Pro Gln Ala
1               5

<210> SEQ ID NO 37
<211> LENGTH: 124
<212> TYPE: PRT
<213> ORGANISM: Homo sapiens

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

Trp Met Thr Trp Val Arg Gln Ala Pro Gly Lys Gly Leu Glu Met Val
        35                  40                  45

Ala Asn Ile Lys Lys Asp Gly Ser Glu Lys Ser Tyr Val Asp Ser Val
 50                  55                  60

Lys Gly Arg Phe Thr Thr Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Pro Asn Cys Gly Gly Asp Cys Tyr Leu Pro Trp Tyr Phe Asp
             100                 105                 110

Leu Trp Gly Arg Gly Thr Leu Val Thr Val Ser Ser
         115                 120

<210> SEQ ID NO 38
<211> LENGTH: 122
<212> TYPE: PRT
<213> ORGANISM: Homo sapiens

<400> SEQUENCE: 38

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
             20                  25                  30

Ser Asn Asn Lys Asn Tyr Leu Ala Trp Tyr Gln Gln Lys Pro Gly Gln
         35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Asn Thr Pro Gln Ala Phe Gly Gln Gly Thr Lys Val Glu Ile
             100                 105                 110

Lys Arg Thr Val Ala Ala Pro Ser Val Phe
         115                 120

<210> SEQ ID NO 39
<211> LENGTH: 372
<212> TYPE: DNA
<213> ORGANISM: Homo sapiens

<400> SEQUENCE: 39
gaggtgcagc tggtggagtc tgggggaggc ttggtccagc ctggggggtc cctgagactc      60
tcctgtgcag cctctggatt cacctttagt agctattgga tgacctgggt ccgccaggct    120
ccagggaagg ggctggagtg ggtggccaac ataaagaaag atggaagtga aaatcctat     180
gtggactctg tgaagggccg attcaccacc tccagacaca cgccaagaa ctcactgtat    240
ctgcaaatga acagcctgag agccgaggac acggctgtgt attactgtgc gagacccaat    300
tgtggtggtg actgctattt accatggtac ttcgatctct ggggccgtgg caccctggtc    360
actgtctcct ca                                                        372

<210> SEQ ID NO 40
<211> LENGTH: 366
<212> TYPE: DNA
<213> ORGANISM: Homo sapiens

<400> SEQUENCE: 40

```
gacatcgtga tgacccagtc tccagactcc ctggctgtgt ctctgggcga gagggccacc     60
atcaactgca agtccagcca gagtgtttta tacagctcca acaataagaa ctacttagct    120
tggtaccagc agaaaccagg acagcctcct aaactactca tttactgggc atctacccgg    180
gaatccgggg tccctgaccg attcagtggc agcgggtctg ggacagattt cactctcacc    240
atcagcagcc tgcaggctga agatgtggca gtttattact gtcagcaata ttataatact    300
cctcaggcgt tcggccaagg gaccaaggtg gaaatcaaac gaactgtggc tgcaccatct    360
gtcttc                                                               366
```

<210> SEQ ID NO 41
<211> LENGTH: 20
<212> TYPE: DNA
<213> ORGANISM: Artificial Sequence
<220> FEATURE:
<223> OTHER INFORMATION: forward primer

<400> SEQUENCE: 41

```
gctttccctg gcaaggtttg                                                 20
```

<210> SEQ ID NO 42
<211> LENGTH: 20
<212> TYPE: DNA
<213> ORGANISM: Artificial Sequence
<220> FEATURE:
<223> OTHER INFORMATION: reverse primer

<400> SEQUENCE: 42

```
agctcagaac ttggtgcctc                                                 20
```

<210> SEQ ID NO 43
<211> LENGTH: 20
<212> TYPE: DNA
<213> ORGANISM: Artificial sequence
<220> FEATURE:
<223> OTHER INFORMATION: forward primer

<400> SEQUENCE: 43

```
ggcaaggtac cctggctaaa                                                 20
```

<210> SEQ ID NO 44
<211> LENGTH: 20
<212> TYPE: DNA
<213> ORGANISM: Artificial sequence
<220> FEATURE:
<223> OTHER INFORMATION: Reverse primer

<400> SEQUENCE: 44

```
aaatctgctg agggacaggc                                                 20
```

<210> SEQ ID NO 45
<211> LENGTH: 20
<212> TYPE: DNA
<213> ORGANISM: Artificial sequence
<220> FEATURE:
<223> OTHER INFORMATION: Forward primer

<400> SEQUENCE: 45

```
atcgcacttg tgcctacgat                                                 20
```

<210> SEQ ID NO 46
<211> LENGTH: 20

```
<212> TYPE: DNA
<213> ORGANISM: Artificial sequence
<220> FEATURE:
<223> OTHER INFORMATION: Reverse primer

<400> SEQUENCE: 46
gctccaggaa gacacaacca                                               20

<210> SEQ ID NO 47
<211> LENGTH: 20
<212> TYPE: DNA
<213> ORGANISM: Artificial sequence
<220> FEATURE:
<223> OTHER INFORMATION: Forward primer

<400> SEQUENCE: 47
ccaccatgta cccaggcatt                                               20

<210> SEQ ID NO 48
<211> LENGTH: 20
<212> TYPE: DNA
<213> ORGANISM: Artificial sequence
<220> FEATURE:
<223> OTHER INFORMATION: Reverse primer

<400> SEQUENCE: 48
agggtgtaaa acgcagctca                                               20

<210> SEQ ID NO 49
<211> LENGTH: 20
<212> TYPE: DNA
<213> ORGANISM: Artificial sequence
<220> FEATURE:
<223> OTHER INFORMATION: Forward primer

<400> SEQUENCE: 49
aaaatgcggg ttttgagccc                                               20

<210> SEQ ID NO 50
<211> LENGTH: 20
<212> TYPE: DNA
<213> ORGANISM: Artificial sequence
<220> FEATURE:
<223> OTHER INFORMATION: Reverse primer

<400> SEQUENCE: 50
cgttggggtc gtcttcttca                                               20

<210> SEQ ID NO 51
<211> LENGTH: 20
<212> TYPE: DNA
<213> ORGANISM: Artificial sequence
<220> FEATURE:
<223> OTHER INFORMATION: Forward primer

<400> SEQUENCE: 51
gctccccaac agtgtctacc                                               20

<210> SEQ ID NO 52
<211> LENGTH: 20
<212> TYPE: DNA
<213> ORGANISM: Artificial sequence
<220> FEATURE:
<223> OTHER INFORMATION: Reverse primer

<400> SEQUENCE: 52
```

<210> SEQ ID NO 53
<211> LENGTH: 137
<212> TYPE: PRT
<213> ORGANISM: Mus musculus

<400> SEQUENCE: 53

Asp Asp Glu Ala Thr Ile Leu Ala Asp Asn Lys Cys Met Cys Thr Arg
1               5                   10                  15

Val Thr Ser Lys Ile Ile Pro Ser Thr Glu Asp Pro Asn Glu Asp Ile
            20                  25                  30

Val Glu Arg Asn Ile Arg Ile Val Val Pro Leu Asn Asn Arg Glu Asn
        35                  40                  45

Ile Ser Asp Pro Thr Ser Pro Leu Arg Arg Asn Phe Val Tyr His Leu
    50                  55                  60

Ser Asp Val Cys Lys Lys Cys Asp Pro Val Glu Val Glu Leu Glu Asp
65                  70                  75                  80

Gln Val Val Thr Ala Thr Gln Ser Asn Ile Cys Asn Glu Asp Asp Gly
                85                  90                  95

Val Pro Glu Thr Cys Tyr Met Tyr Asp Arg Asn Lys Cys Tyr Thr Thr
            100                 105                 110

Met Val Pro Leu Arg Tyr His Gly Glu Thr Lys Met Val Glu Ala Ala
        115                 120                 125

Leu Thr Pro Asp Ser Cys Tyr Pro Asp
    130                 135

<210> SEQ ID NO 54
<211> LENGTH: 137
<212> TYPE: PRT
<213> ORGANISM: Homo sapiens

<400> SEQUENCE: 54

Gln Glu Asp Glu Arg Ile Val Leu Val Asp Asn Lys Cys Lys Cys Ala
1               5                   10                  15

Arg Ile Thr Ser Arg Ile Ile Arg Ser Ser Glu Asp Pro Asn Glu Asp
            20                  25                  30

Ile Val Glu Arg Asn Ile Arg Ile Ile Val Pro Leu Asn Asn Arg Glu
        35                  40                  45

Asn Ile Ser Asp Pro Thr Ser Pro Leu Arg Thr Arg Phe Val Tyr His
    50                  55                  60

Leu Ser Asp Leu Cys Lys Lys Cys Asp Pro Thr Glu Val Glu Leu Asp
65                  70                  75                  80

Asn Gln Ile Val Thr Ala Thr Gln Ser Asn Ile Cys Asp Glu Asp Ser
                85                  90                  95

Ala Thr Glu Thr Cys Tyr Thr Tyr Asp Arg Asn Lys Cys Tyr Thr Ala
            100                 105                 110

Val Val Pro Leu Val Tyr Gly Gly Glu Thr Lys Met Val Glu Thr Ala
        115                 120                 125

Leu Thr Pro Asp Ala Cys Tyr Pro Asp
    130                 135

<210> SEQ ID NO 55
<211> LENGTH: 19
<212> TYPE: PRT
<213> ORGANISM: Homo sapiens

<400> SEQUENCE: 55

```
Val Ala Ile Ile Ser Tyr Asp Gly Ser Arg Lys Tyr Tyr Ala Asp Ser
1               5                   10                  15

Val Lys Gly

<210> SEQ ID NO 56
<211> LENGTH: 12
<212> TYPE: PRT
<213> ORGANISM: Homo sapiens

<400> SEQUENCE: 56

Cys Glu Thr Trp Asp Ser Ser Leu Ser Ala Val Val
1               5                   10
```